(12) United States Patent
Goble et al.

(10) Patent No.: US 12,262,882 B2
(45) Date of Patent: *Apr. 1, 2025

(54) SEALING DEVICE AND DELIVERY SYSTEM

(71) Applicant: W. L. Gore & Associates, Inc., Newark, DE (US)

(72) Inventors: Jacob A. Goble, Bellemont, AZ (US); Brandon A. Lurie, Flagstaff, AZ (US); Steven J. Masters, Flagstaff, AZ (US); Scot K. Mathena, Flagstaff, AZ (US); Richard L McClure, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/231,986

(22) Filed: Aug. 9, 2023

(65) Prior Publication Data
US 2023/0380821 A1 Nov. 30, 2023

Related U.S. Application Data

(63) Continuation of application No. 16/405,508, filed on May 7, 2019, now Pat. No. 11,771,408, which is a (Continued)

(51) Int. Cl.
*A61B 17/00* (2006.01)

(52) U.S. Cl.
CPC ...... *A61B 17/0057* (2013.01); *A61B 2017/00575* (2013.01); *A61B 2017/00592* (2013.01);
(Continued)

(58) Field of Classification Search
CPC ...... A61B 17/0057; A61B 2017/00575; A61B 2017/00592; A61B 2017/00597; A61B 2017/00606
See application file for complete search history.

(56) References Cited

U.S. PATENT DOCUMENTS

| 283,653 A | 8/1883 | Paxson. |
|---|---|---|
| 3,294,631 A | 12/1966 | Walter et al. |

(Continued)

FOREIGN PATENT DOCUMENTS

| CA | 2627408 A1 | 5/2007 |
|---|---|---|
| CN | 1218379 A | 6/1999 |

(Continued)

OTHER PUBLICATIONS

Athanasion, "Coronary artery bypass with the use of a magnetic distal anastomotic device: surgical technique and preliminary experience," Heart Surg Forum., 2004;7 (6):356-359.

(Continued)

*Primary Examiner* — Steven O Douglas

(57) ABSTRACT

A medical device for sealing a defect in a body includes a wire frame that includes a plurality of wires that form a first occluding member and a second occluding member, the wire frame including a defect-occupying portion disposed between the first occluding member and the second occluding member. The defect-occupying portion is adapted to fill a wide range of potential defect sizes, such that no more than five devices of a range of sizes are required to effectively seal a range of nominal defect sizes of approximately 8 to 35 mm.

15 Claims, 40 Drawing Sheets

Related U.S. Application Data continuation of application No. 13/838,166, filed on Mar. 15, 2013, now Pat. No. 10,828,019.

(60) Provisional application No. 61/754,504, filed on Jan. 18, 2013.

(52) U.S. Cl.
CPC ............. *A61B 2017/00597* (2013.01); *A61B 2017/00606* (2013.01)

(56) References Cited

U.S. PATENT DOCUMENTS

| | | |
|---|---|---|
| 3,324,518 A | 6/1967 | Louderback |
| 3,447,533 A | 6/1969 | Spicer |
| 3,739,770 A | 6/1973 | Mori |
| 3,784,388 A | 1/1974 | King et al. |
| 3,824,631 A | 7/1974 | Burstein et al. |
| 3,874,388 A | 4/1975 | King et al. |
| 3,875,648 A | 4/1975 | Bone |
| 3,907,675 A | 9/1975 | Chapurlat et al. |
| 3,924,631 A | 12/1975 | Mancusi, Jr. |
| 3,939,849 A | 2/1976 | Baxter et al. |
| 4,006,747 A | 2/1977 | Kronenthal et al. |
| 4,007,743 A | 2/1977 | Blake |
| 4,038,365 A | 7/1977 | Patil et al. |
| 4,113,912 A | 9/1978 | Okita |
| 4,149,327 A | 4/1979 | Hammer et al. |
| 4,193,138 A | 3/1980 | Okita |
| 4,425,908 A | 1/1984 | Simon |
| 4,525,374 A | 6/1985 | Vaillancourt |
| 4,610,674 A | 9/1986 | Suzuki et al. |
| 4,619,246 A | 10/1986 | Molgaard-Nielsen et al. |
| 4,626,245 A | 12/1986 | Weinstein |
| 4,665,918 A | 5/1987 | Garza et al. |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,766,898 A | 8/1988 | Hardy et al. |
| 4,796,612 A | 1/1989 | Reese |
| 4,832,055 A | 5/1989 | Palestrant |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,917,793 A | 4/1990 | Pitt et al. |
| 4,921,479 A | 5/1990 | Grayzel |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,041,225 A | 8/1991 | Norman |
| 5,049,131 A | 9/1991 | Deuss |
| 5,049,275 A | 9/1991 | Gillberg-LaForce et al. |
| 5,078,736 A | 1/1992 | Behl |
| 5,090,422 A | 2/1992 | Dahl et al. |
| 5,098,440 A | 3/1992 | Hillstead |
| 5,106,913 A | 4/1992 | Yamaguchi et al. |
| 5,108,420 A | 4/1992 | Marks |
| 5,124,109 A | 6/1992 | Drossbach |
| 5,149,327 A | 9/1992 | Oshiyama |
| 5,152,144 A | 10/1992 | Andrie |
| 5,163,131 A | 11/1992 | Row et al. |
| 5,167,363 A | 12/1992 | Adkinson et al. |
| 5,167,637 A | 12/1992 | Okada et al. |
| 5,171,259 A | 12/1992 | Inoue |
| 5,171,314 A | 12/1992 | Dulebohn |
| 5,176,659 A | 1/1993 | Mancini |
| 5,192,301 A | 3/1993 | Kamiya et al. |
| 5,222,974 A | 6/1993 | Kensey et al. |
| 5,226,879 A | 7/1993 | Ensminger et al. |
| 5,234,458 A | 8/1993 | Metais |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,269,809 A | 12/1993 | Hayhurst et al. |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,320,611 A | 6/1994 | Bonutti et al. |
| 5,334,217 A | 8/1994 | Das |
| 5,342,393 A | 8/1994 | Stack |
| 5,350,363 A | 9/1994 | Goode et al. |
| 5,350,399 A | 9/1994 | Erlebacher et al. |
| 5,354,308 A | 10/1994 | Simon et al. |
| 5,364,356 A | 11/1994 | Berthold |
| 5,397,331 A | 3/1995 | Himpens et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,437,288 A | 8/1995 | Schwartz et al. |
| 5,443,727 A | 8/1995 | Gagnon |
| 5,443,972 A | 8/1995 | Kohama et al. |
| 5,451,235 A | 9/1995 | Lock et al. |
| 5,453,099 A | 9/1995 | Lee et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,549,959 A | 8/1996 | Compton |
| 5,562,632 A | 10/1996 | Davila et al. |
| 5,562,728 A | 10/1996 | Lazarus et al. |
| 5,571,169 A | 11/1996 | Plaia et al. |
| 5,575,816 A | 11/1996 | Rudnick et al. |
| 5,577,299 A | 11/1996 | Thompson et al. |
| 5,578,045 A | 11/1996 | Das |
| 5,591,206 A | 1/1997 | Moufarrege |
| 5,601,571 A | 2/1997 | Moss |
| 5,603,703 A | 2/1997 | Elsberry et al. |
| 5,618,311 A | 4/1997 | Gryskiewicz |
| 5,620,461 A | 4/1997 | Muijs et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,662,701 A | 9/1997 | Plaia et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,713,864 A | 2/1998 | Verkaart |
| 5,713,948 A | 2/1998 | Uflacker |
| 5,717,259 A | 2/1998 | Schexnayder |
| 5,720,754 A | 2/1998 | Middleman et al. |
| 5,725,552 A | 3/1998 | Kotula et al. |
| 5,725,553 A | 3/1998 | Moenning |
| 5,733,294 A | 3/1998 | Forber et al. |
| 5,733,337 A | 3/1998 | Carr et al. |
| 5,741,297 A | 4/1998 | Simon |
| 5,749,880 A | 5/1998 | Banas et al. |
| 5,755,762 A | 5/1998 | Bush |
| 5,769,882 A | 6/1998 | Fogarty et al. |
| 5,772,641 A | 6/1998 | Wilson |
| 5,776,162 A | 7/1998 | Kleshinski |
| 5,776,183 A | 7/1998 | Kanesaka et al. |
| 5,782,847 A | 7/1998 | Plaia et al. |
| 5,782,860 A | 7/1998 | Epstein et al. |
| 5,797,960 A | 8/1998 | Stevens et al. |

(56) References Cited

U.S. PATENT DOCUMENTS

| | | |
|---|---|---|
| 5,799,384 A | 9/1998 | Schwartz et al. |
| 5,800,436 A | 9/1998 | Lerch |
| 5,800,516 A | 9/1998 | Fine et al. |
| 5,810,884 A | 9/1998 | Kim |
| 5,820,594 A | 10/1998 | Fontirroche et al. |
| 5,823,956 A | 10/1998 | Roth et al. |
| 5,829,447 A | 11/1998 | Stevens et al. |
| 5,835,422 A | 11/1998 | Merritt |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,865,844 A | 2/1999 | Plaia et al. |
| 5,873,905 A | 2/1999 | Plaia et al. |
| 5,879,366 A | 3/1999 | Shaw et al. |
| 5,893,856 A | 4/1999 | Jacob et al. |
| 5,895,411 A | 4/1999 | Irie |
| 5,897,955 A | 4/1999 | Drumheller |
| 5,902,287 A | 5/1999 | Martin |
| 5,902,319 A | 5/1999 | Daley |
| 5,902,745 A | 5/1999 | Butler et al. |
| 5,904,703 A | 5/1999 | Gilson |
| 5,906,639 A | 5/1999 | Rudnick et al. |
| 5,919,200 A | 7/1999 | Stambaugh et al. |
| 5,924,424 A | 7/1999 | Stevens et al. |
| 5,925,060 A | 7/1999 | Forber |
| 5,928,250 A | 7/1999 | Koike et al. |
| 5,944,691 A | 8/1999 | Querns et al. |
| 5,944,738 A | 8/1999 | Amplatz et al. |
| 5,955,110 A | 9/1999 | Patel et al. |
| 5,957,490 A | 9/1999 | Sinnhuber |
| 5,957,953 A | 9/1999 | Dipoto et al. |
| 5,967,490 A | 10/1999 | Pike |
| 5,976,174 A | 11/1999 | Ruiz |
| 5,980,505 A | 11/1999 | Wilson |
| 5,989,268 A | 11/1999 | Pugsley et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,016,846 A | 1/2000 | Knittel et al. |
| 6,019,753 A | 2/2000 | Pagan |
| 6,024,756 A | 2/2000 | Huebsch et al. |
| 6,027,519 A | 2/2000 | Stanford |
| 6,030,007 A | 2/2000 | Bassily et al. |
| 6,051,007 A | 4/2000 | Hogendijk et al. |
| 6,053,939 A | 4/2000 | Okuda et al. |
| 6,056,760 A | 5/2000 | Koike et al. |
| 6,071,998 A | 6/2000 | Muller et al. |
| 6,074,401 A | 6/2000 | Gardiner et al. |
| 6,077,281 A | 6/2000 | Das |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,080,183 A | 6/2000 | Tsugita et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,123,715 A | 9/2000 | Amplatz |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,168,588 B1 | 1/2001 | Wilson |
| 6,171,329 B1 | 1/2001 | Shaw et al. |
| 6,174,322 B1 | 1/2001 | Schneidt |
| 6,174,330 B1 | 1/2001 | Stinson |
| 6,183,443 B1 | 2/2001 | Kratoska et al. |
| 6,183,496 B1 | 2/2001 | Urbanski |
| 6,187,039 B1 | 2/2001 | Hiles et al. |
| 6,190,353 B1 | 2/2001 | Makower et al. |
| 6,190,357 B1 | 2/2001 | Ferrari et al. |
| 6,197,016 B1 | 3/2001 | Fourkas et al. |
| 6,199,262 B1 | 3/2001 | Martin |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,258,091 B1 | 7/2001 | Sevrain et al. |
| 6,261,309 B1 | 7/2001 | Urbanski |
| 6,265,333 B1 | 7/2001 | Dzenis et al. |
| 6,270,500 B1 | 8/2001 | Lerch |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,290,689 B1 | 9/2001 | Delaney et al. |
| 6,290,721 B1 | 9/2001 | Heath |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,427 B1 | 12/2001 | Watanabe et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,355,852 B1 | 3/2002 | Bricker et al. |
| 6,356,782 B1 | 3/2002 | Sirimanne et al. |
| 6,358,238 B1 | 3/2002 | Sherry |
| 6,364,853 B1 | 4/2002 | French et al. |
| 6,368,338 B1 | 4/2002 | Konya et al. |
| 6,371,904 B1 | 4/2002 | Sirimanne et al. |
| 6,375,625 B1 | 4/2002 | French et al. |
| 6,375,668 B1 | 4/2002 | Gifford et al. |
| 6,375,671 B1 | 4/2002 | Kobayashi et al. |
| 6,379,342 B1 | 4/2002 | Levinson |
| 6,379,363 B1 | 4/2002 | Herrington et al. |
| 6,379,368 B1 | 4/2002 | Corcoran et al. |
| 6,387,104 B1 | 5/2002 | Pugsley et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,443,972 B1 | 9/2002 | Bosma et al. |
| 6,450,987 B1 | 9/2002 | Kramer |
| 6,460,749 B1 | 10/2002 | Levinson et al. |
| 6,468,303 B1 | 10/2002 | Amplatz et al. |
| 6,478,773 B1 | 11/2002 | Gandhi et al. |
| 6,482,224 B1 | 11/2002 | Michler et al. |
| 6,488,706 B1 | 12/2002 | Solymar |
| 6,491,714 B1 | 12/2002 | Bennett |
| 6,494,846 B1 | 12/2002 | Margolis |
| 6,494,888 B1 | 12/2002 | Laufer et al. |
| 6,497,709 B1 | 12/2002 | Heath |
| 6,506,204 B2 | 1/2003 | Mazzocchi |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van et al. |

(56) References Cited

U.S. PATENT DOCUMENTS

| | | |
|---|---|---|
| 6,551,344 B2 | 4/2003 | Thill |
| 6,554,849 B1 | 4/2003 | Jones et al. |
| 6,585,719 B2 | 7/2003 | Wang |
| 6,585,755 B2 | 7/2003 | Jackson et al. |
| 6,589,251 B2 | 7/2003 | Yee et al. |
| 6,596,013 B2 | 7/2003 | Yang et al. |
| 6,599,448 B1 | 7/2003 | Ehrhard et al. |
| 6,610,764 B1 | 8/2003 | Martin et al. |
| 6,623,506 B2 | 9/2003 | McGuckin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,652,556 B1 | 11/2003 | Vantassel et al. |
| 6,666,861 B1 | 12/2003 | Grabek |
| 6,669,707 B1 | 12/2003 | Swanstrom et al. |
| 6,669,713 B2 | 12/2003 | Adams |
| 6,669,722 B2 | 12/2003 | Chen et al. |
| 6,685,707 B2 | 2/2004 | Roman et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,755,834 B2 | 6/2004 | Amis |
| 6,786,915 B2 | 9/2004 | Akerfeldt et al. |
| 6,828,357 B1 | 12/2004 | Martin et al. |
| 6,838,493 B2 | 1/2005 | Williams et al. |
| 6,855,126 B2 | 2/2005 | Flinchbaugh |
| 6,860,895 B1 | 3/2005 | Akerfeldt et al. |
| 6,866,669 B2 | 3/2005 | Buzzard et al. |
| 6,867,247 B2 | 3/2005 | Williams et al. |
| 6,867,248 B1 | 3/2005 | Martin et al. |
| 6,867,249 B2 | 3/2005 | Lee |
| 6,921,401 B2 | 7/2005 | Lerch et al. |
| 6,921,410 B2 | 7/2005 | Porter |
| 6,939,352 B2 | 9/2005 | Buzzard et al. |
| 6,949,116 B2 | 9/2005 | Solymar et al. |
| 6,994,092 B2 | 2/2006 | Van et al. |
| 7,044,134 B2 | 5/2006 | Khairkhahan et al. |
| 7,048,738 B1 | 5/2006 | Wellisz et al. |
| 7,097,653 B2 | 8/2006 | Freudenthal et al. |
| 7,128,073 B1 | 10/2006 | Van et al. |
| 7,149,587 B2 | 12/2006 | Wardle et al. |
| 7,152,605 B2 | 12/2006 | Khairkhahan et al. |
| 7,165,552 B2 | 1/2007 | Deem et al. |
| 7,198,631 B2 | 4/2007 | Kanner et al. |
| 7,207,402 B2 | 4/2007 | Fredrik |
| 7,223,271 B2 | 5/2007 | Muramatsu et al. |
| 7,238,188 B2 | 7/2007 | Nesper et al. |
| 7,335,426 B2 | 2/2008 | Marton et al. |
| 7,361,178 B2 | 4/2008 | Hearn et al. |
| 7,381,216 B2 | 6/2008 | Buzzard et al. |
| 7,431,729 B2 | 10/2008 | Chanduszko |
| 7,452,363 B2 | 11/2008 | Ortiz |
| 7,481,832 B1 | 1/2009 | Meridew et al. |
| 7,582,104 B2 | 9/2009 | Corcoran et al. |
| 7,597,704 B2 | 10/2009 | Frazier et al. |
| 7,658,748 B2 | 2/2010 | Marino et al. |
| 7,678,123 B2 | 3/2010 | Chanduszko |
| 7,704,268 B2 | 4/2010 | Chanduszko |
| 7,735,493 B2 | 6/2010 | Van et al. |
| 7,780,700 B2 | 8/2010 | Frazier et al. |
| 7,842,053 B2 | 11/2010 | Chanduszko et al. |
| 7,871,419 B2 | 1/2011 | Devellian et al. |
| 7,875,052 B2 | 1/2011 | Kawaura et al. |
| 7,887,562 B2 | 2/2011 | Young et al. |
| 7,905,901 B2 | 3/2011 | Corcoran et al. |
| 7,918,872 B2 | 4/2011 | Mitelberg et al. |
| 8,034,061 B2 | 10/2011 | Amplatz et al. |
| 8,062,325 B2 | 11/2011 | Mitelberg et al. |
| 8,118,833 B2 | 2/2012 | Seibold et al. |
| 8,252,019 B2 | 8/2012 | Fleming, III |
| 8,257,389 B2 | 9/2012 | Chanduszko et al. |
| 8,277,480 B2 | 10/2012 | Callaghan et al. |
| 8,308,760 B2 | 11/2012 | Chanduszko |
| 8,361,110 B2 | 1/2013 | Chanduszko |
| 8,480,706 B2 | 7/2013 | Chanduszko et al. |
| 8,551,135 B2 | 10/2013 | Kladakis et al. |
| 8,585,714 B2 | 11/2013 | Weisel et al. |
| 8,753,362 B2 | 6/2014 | Widomski et al. |
| 8,764,790 B2 | 7/2014 | Thommen et al. |
| 8,764,848 B2 | 7/2014 | Callaghan et al. |
| 8,814,947 B2 | 8/2014 | Callaghan |
| 8,821,528 B2 | 9/2014 | McGuckin et al. |
| 8,858,576 B2 | 10/2014 | Takahashi et al. |
| 8,956,389 B2 | 2/2015 | Van Orden |
| 9,005,242 B2 | 4/2015 | Cahill |
| 9,119,607 B2 | 9/2015 | Amin |
| 9,138,213 B2 | 9/2015 | Amin et al. |
| 9,149,263 B2 | 10/2015 | Chanduszko |
| 9,326,759 B2 | 5/2016 | Chanduszko et al. |
| 9,381,006 B2 | 7/2016 | Masters |
| 9,451,939 B2 | 9/2016 | Aurilia et al. |
| 9,468,430 B2 | 10/2016 | Van Orden |
| 9,474,517 B2 | 10/2016 | Amin et al. |
| 9,636,094 B2 | 5/2017 | Aurilia et al. |
| 9,808,230 B2 | 11/2017 | Brown et al. |
| 9,861,346 B2 | 1/2018 | Callaghan |
| 9,949,728 B2 | 4/2018 | Cahill |
| 10,368,853 B2 | 8/2019 | Brown et al. |
| 10,485,525 B2 | 11/2019 | Cahill |
| 10,792,025 B2 | 10/2020 | Masters |
| 10,806,437 B2 | 10/2020 | Masters et al. |
| 10,828,019 B2 | 11/2020 | Goble et al. |
| 11,375,988 B2 | 7/2022 | Callaghan |
| 11,589,853 B2 | 2/2023 | Masters |
| 11,596,391 B2 | 3/2023 | Aurilia et al. |
| 11,771,408 B2 | 10/2023 | Goble et al. |
| 12,059,140 B2 | 8/2024 | Cahill |
| 12,082,795 B2 | 9/2024 | Masters |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0037141 A1 | 11/2001 | Yee et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2001/0049551 A1 | 12/2001 | Tseng et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058980 A1 | 5/2002 | Sass |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0095183 A1 | 7/2002 | Casset et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0099437 A1 | 7/2002 | Anson et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |

(56) References Cited

U.S. PATENT DOCUMENTS

| | | |
|---|---|---|
| 2002/0143292 A1 | 10/2002 | Flinchbaugh |
| 2002/0156475 A1 | 10/2002 | Lerch et al. |
| 2002/0156499 A1 | 10/2002 | Konya et al. |
| 2002/0163434 A1 | 11/2002 | Burke |
| 2002/0164729 A1 | 11/2002 | Skraly et al. |
| 2002/0169377 A1 | 11/2002 | Khairkhahan et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Borillo et al. |
| 2003/0028213 A1 | 2/2003 | Thill et al. |
| 2003/0040771 A1 | 2/2003 | Hyodoh et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0113868 A1 | 6/2003 | Flor et al. |
| 2003/0120337 A1 | 6/2003 | Van et al. |
| 2003/0130683 A1 | 7/2003 | Andreas et al. |
| 2003/0139819 A1 | 7/2003 | Beer et al. |
| 2003/0149463 A1 | 8/2003 | Solymar et al. |
| 2003/0150821 A1 | 8/2003 | Bates et al. |
| 2003/0153901 A1 | 8/2003 | Herweck et al. |
| 2003/0171774 A1 | 9/2003 | Freudenthal et al. |
| 2003/0187390 A1 | 10/2003 | Bates et al. |
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0204203 A1 | 10/2003 | Khairkhahan et al. |
| 2003/0225421 A1 | 12/2003 | Peavey et al. |
| 2003/0225439 A1 | 12/2003 | Cook et al. |
| 2004/0006330 A1 | 1/2004 | Fangrow |
| 2004/0044361 A1 | 3/2004 | Frazier et al. |
| 2004/0044364 A1 | 3/2004 | Devries et al. |
| 2004/0073242 A1 | 4/2004 | Chanduszko |
| 2004/0093017 A1 | 5/2004 | Chanduszko |
| 2004/0098042 A1 | 5/2004 | Devellian et al. |
| 2004/0116959 A1 | 6/2004 | Mcguckin et al. |
| 2004/0127919 A1 | 7/2004 | Trout et al. |
| 2004/0133230 A1 | 7/2004 | Carpenter et al. |
| 2004/0133236 A1 | 7/2004 | Chanduszko |
| 2004/0143294 A1 | 7/2004 | Corcoran et al. |
| 2004/0167566 A1 | 8/2004 | Beulke et al. |
| 2004/0176799 A1 | 9/2004 | Chanduszko et al. |
| 2004/0186510 A1 | 9/2004 | Weaver |
| 2004/0193206 A1 | 9/2004 | Gerberding et al. |
| 2004/0210301 A1 | 10/2004 | Obermiller |
| 2004/0220596 A1 | 11/2004 | Frazier et al. |
| 2004/0220610 A1 | 11/2004 | Kreidler et al. |
| 2004/0230222 A1 | 11/2004 | Van et al. |
| 2004/0234567 A1 | 11/2004 | Dawson |
| 2004/0254594 A1 | 12/2004 | Alfaro |
| 2005/0025809 A1 | 2/2005 | Hasirci et al. |
| 2005/0038470 A1 | 2/2005 | Van et al. |
| 2005/0043759 A1 | 2/2005 | Chanduszko |
| 2005/0055039 A1 | 3/2005 | Burnett et al. |
| 2005/0065548 A1 | 3/2005 | Marino et al. |
| 2005/0067523 A1 | 3/2005 | Zach et al. |
| 2005/0070935 A1 | 3/2005 | Ortiz |
| 2005/0080476 A1 | 4/2005 | Gunderson et al. |
| 2005/0085843 A1 | 4/2005 | Opolski et al. |
| 2005/0113868 A1 | 5/2005 | Devellian et al. |
| 2005/0119690 A1 | 6/2005 | Mazzocchi et al. |
| 2005/0137692 A1 | 6/2005 | Haug et al. |
| 2005/0137699 A1 | 6/2005 | Salahieh et al. |
| 2005/0161264 A1 | 7/2005 | Bjork |
| 2005/0182426 A1 | 8/2005 | Adams et al. |
| 2005/0187564 A1 | 8/2005 | Jayaraman |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0267523 A1 | 12/2005 | Devellian et al. |
| 2005/0267525 A1 | 12/2005 | Chanduszko |
| 2005/0267572 A1 | 12/2005 | Schoon et al. |
| 2005/0273135 A1 | 12/2005 | Chanduszko et al. |
| 2005/0288706 A1 | 12/2005 | Widomski et al. |
| 2005/0288786 A1 | 12/2005 | Chanduszko |
| 2006/0020332 A1 | 1/2006 | Lashinski et al. |
| 2006/0025790 A1 | 2/2006 | De et al. |
| 2006/0030884 A1 | 2/2006 | Yeung et al. |
| 2006/0052821 A1 | 3/2006 | Abbott et al. |
| 2006/0106447 A1 | 5/2006 | Opolski |
| 2006/0109073 A1 | 5/2006 | Allison et al. |
| 2006/0116710 A1 | 6/2006 | Corcoran et al. |
| 2006/0122646 A1 | 6/2006 | Corcoran et al. |
| 2006/0122647 A1 | 6/2006 | Callaghan et al. |
| 2006/0167494 A1 | 7/2006 | Suddaby |
| 2006/0206148 A1 | 9/2006 | Khairkhahan et al. |
| 2006/0217764 A1 | 9/2006 | Abbott et al. |
| 2006/0224183 A1 | 10/2006 | Freudenthal |
| 2006/0235463 A1 | 10/2006 | Freudenthal et al. |
| 2006/0241690 A1 | 10/2006 | Amplatz et al. |
| 2006/0265004 A1 | 11/2006 | Callaghan et al. |
| 2006/0271089 A1 | 11/2006 | Alejandro et al. |
| 2006/0276839 A1 | 12/2006 | McGuckin, Jr. |
| 2007/0010851 A1 | 1/2007 | Chanduszko et al. |
| 2007/0021758 A1 | 1/2007 | Ortiz |
| 2007/0066994 A1 | 3/2007 | Blaeser et al. |
| 2007/0088388 A1 | 4/2007 | Opolski et al. |
| 2007/0096048 A1 | 5/2007 | Clerc |
| 2007/0112381 A1 | 5/2007 | Figulla et al. |
| 2007/0118176 A1 | 5/2007 | Opolski et al. |
| 2007/0129755 A1 | 6/2007 | Abbott et al. |
| 2007/0156225 A1 | 7/2007 | George et al. |
| 2007/0167980 A1 | 7/2007 | Figulla et al. |
| 2007/0167981 A1 | 7/2007 | Opolski et al. |
| 2007/0179474 A1 | 8/2007 | Cahill et al. |
| 2007/0185529 A1 | 8/2007 | Coleman et al. |
| 2007/0191884 A1 | 8/2007 | Eskridge et al. |
| 2007/0208350 A1 | 9/2007 | Gunderson |
| 2007/0225760 A1 | 9/2007 | Moszner et al. |
| 2007/0233186 A1 | 10/2007 | Meng |
| 2007/0244517 A1 | 10/2007 | Callaghan |
| 2007/0244518 A1 | 10/2007 | Callaghan |
| 2007/0250081 A1 | 10/2007 | Cahill et al. |
| 2007/0250115 A1 | 10/2007 | Opolski et al. |
| 2007/0265656 A1 | 11/2007 | Amplatz et al. |
| 2007/0276415 A1 | 11/2007 | Kladakis et al. |
| 2007/0282430 A1 | 12/2007 | Thommen et al. |
| 2008/0015633 A1 | 1/2008 | Abbott et al. |
| 2008/0027528 A1 | 1/2008 | Jagger et al. |
| 2008/0033475 A1 | 2/2008 | Meng |
| 2008/0058800 A1 | 3/2008 | Collins et al. |
| 2008/0065149 A1 | 3/2008 | Thielen et al. |
| 2008/0077180 A1 | 3/2008 | Kladakis et al. |
| 2008/0086168 A1 | 4/2008 | Cahill |
| 2008/0091234 A1 | 4/2008 | Kladakis |
| 2008/0109073 A1 | 5/2008 | Lashinski et al. |
| 2008/0119886 A1 | 5/2008 | Greenhalgh et al. |
| 2008/0119891 A1 | 5/2008 | Miles et al. |
| 2008/0147111 A1 | 6/2008 | Johnson et al. |
| 2008/0208214 A1 | 8/2008 | Sato et al. |
| 2008/0208226 A1 | 8/2008 | Seibold et al. |
| 2008/0213463 A1 | 9/2008 | Cook et al. |
| 2008/0228218 A1 | 9/2008 | Chanduszko |
| 2008/0249562 A1 | 10/2008 | Cahill |
| 2008/0262518 A1 | 10/2008 | Freudenthal |
| 2008/0312666 A1 | 12/2008 | Ellingwood et al. |
| 2009/0012559 A1 | 1/2009 | Chanduszko |
| 2009/0054912 A1 | 2/2009 | Heanue et al. |
| 2009/0062841 A1 | 3/2009 | Amplatz et al. |
| 2009/0062844 A1 | 3/2009 | Tekulve et al. |
| 2009/0069885 A1 | 3/2009 | Rahdert et al. |
| 2009/0076541 A1 | 3/2009 | Chin et al. |
| 2009/0088795 A1 | 4/2009 | Cahill |
| 2009/0099647 A1 | 4/2009 | Glimsdale et al. |
| 2009/0118745 A1 | 5/2009 | Paul, Jr. |
| 2009/0204133 A1 | 8/2009 | Melzer et al. |

(56) References Cited

U.S. PATENT DOCUMENTS

| | | |
|---|---|---|
| 2009/0228038 A1 | 9/2009 | Amin |
| 2009/0292310 A1 | 11/2009 | Chin et al. |
| 2009/0306706 A1 | 12/2009 | Osypka |
| 2010/0004679 A1 | 1/2010 | Osypka |
| 2010/0121370 A1 | 5/2010 | Kariniemi |
| 2010/0145382 A1 | 6/2010 | Chanduszko |
| 2010/0145385 A1 | 6/2010 | Surti et al. |
| 2010/0160944 A1 | 6/2010 | Teoh et al. |
| 2010/0211046 A1 | 8/2010 | Adams et al. |
| 2010/0234878 A1 | 9/2010 | Hruska et al. |
| 2010/0234884 A1 | 9/2010 | LaFontaine et al. |
| 2010/0234885 A1 | 9/2010 | Frazier et al. |
| 2010/0324538 A1 | 12/2010 | Van Orden |
| 2010/0324585 A1 | 12/2010 | Miles et al. |
| 2010/0324652 A1 | 12/2010 | Aurilia et al. |
| 2011/0040324 A1 | 2/2011 | McCarthy et al. |
| 2011/0054519 A1 | 3/2011 | Neuss |
| 2011/0087146 A1 | 4/2011 | Ryan et al. |
| 2011/0184439 A1 | 7/2011 | Anderson et al. |
| 2011/0184456 A1 | 7/2011 | Grandfield et al. |
| 2011/0218479 A1 | 9/2011 | Rottenberg et al. |
| 2011/0295298 A1 | 12/2011 | Moszner |
| 2011/0301630 A1 | 12/2011 | Hendriksen et al. |
| 2012/0029556 A1 | 2/2012 | Masters |
| 2012/0071918 A1 | 3/2012 | Amin et al. |
| 2012/0116528 A1 | 5/2012 | Nguyen |
| 2012/0143242 A1 | 6/2012 | Masters |
| 2012/0150218 A1 | 6/2012 | Sandgren et al. |
| 2012/0197292 A1 | 8/2012 | Chin-Chen et al. |
| 2012/0245623 A1 | 9/2012 | Kariniemi et al. |
| 2012/0316597 A1 | 12/2012 | Fitz et al. |
| 2013/0041404 A1 | 2/2013 | Amin et al. |
| 2013/0218202 A1 | 8/2013 | Masters |
| 2013/0231684 A1 | 9/2013 | Aurilia et al. |
| 2013/0245666 A1 | 9/2013 | Larsen et al. |
| 2013/0282054 A1 | 10/2013 | Osypka |
| 2013/0296925 A1 | 11/2013 | Chanduszko et al. |
| 2014/0039543 A1 | 2/2014 | Willems et al. |
| 2014/0142610 A1 | 5/2014 | Larsen et al. |
| 2014/0194921 A1 | 7/2014 | Akpinar |
| 2014/0207185 A1 | 7/2014 | Goble et al. |
| 2014/0309684 A1 | 10/2014 | Al-Qbandi et al. |
| 2014/0343602 A1 | 11/2014 | Cox et al. |
| 2015/0005809 A1 | 1/2015 | Ayres et al. |
| 2015/0034452 A1 | 2/2015 | Boon et al. |
| 2015/0039023 A1 | 2/2015 | De et al. |
| 2015/0066077 A1 | 3/2015 | Akpinar |
| 2015/0148731 A1 | 5/2015 | McNamara et al. |
| 2015/0196288 A1 | 7/2015 | Van Orden |
| 2015/0296288 A1 | 10/2015 | Anastas |
| 2016/0249899 A1 | 9/2016 | Cahill |
| 2017/0007221 A1 | 1/2017 | Aurilia et al. |
| 2017/0007222 A1 | 1/2017 | Van Orden |
| 2017/0035435 A1 | 2/2017 | Amin et al. |
| 2017/0105711 A1 | 4/2017 | Masters |
| 2017/0156843 A1 | 6/2017 | Clerc |
| 2017/0215852 A1 | 8/2017 | Aurilia et al. |
| 2018/0092634 A1 | 4/2018 | Callaghan |
| 2019/0261966 A1 | 8/2019 | Goble et al. |
| 2020/0121307 A1 | 4/2020 | Brown et al. |
| 2020/0163659 A1 | 5/2020 | Cahill |
| 2021/0007725 A1 | 1/2021 | Masters |
| 2022/0151599 A1 | 5/2022 | Brown et al. |
| 2023/0041529 A1 | 2/2023 | Masters |
| 2023/0165577 A1 | 6/2023 | Van Orden |
| 2023/0172599 A1 | 6/2023 | Aurilia et al. |

FOREIGN PATENT DOCUMENTS

| | | |
|---|---|---|
| CN | 1247460 A | 3/2000 |
| CN | 1358482 A | 7/2002 |
| CN | 2524710 Y | 12/2002 |
| CN | 200963203 Y | 10/2007 |
| CN | 200980690 Y | 11/2007 |
| CN | 201082203 Y | 7/2008 |
| CN | 101460102 A | 6/2009 |
| CN | 101773418 A | 7/2010 |
| CN | 101815472 A | 8/2010 |
| CN | 102046094 A | 5/2011 |
| CN | 201905941 U | 7/2011 |
| CN | 102802539 A | 11/2012 |
| CN | 103533897 A | 1/2014 |
| DE | 9413645 U1 | 10/1994 |
| DE | 9413649 U1 | 10/1994 |
| DE | 102006036649 A1 | 10/2007 |
| EP | 0362113 A | 4/1990 |
| EP | 0474887 A1 | 3/1992 |
| EP | 0839549 A1 | 5/1998 |
| EP | 0861632 A1 | 9/1998 |
| EP | 1013227 A2 | 6/2000 |
| EP | 1046375 A1 | 10/2000 |
| EP | 1222897 A2 | 7/2002 |
| EP | 1331885 B1 | 3/2009 |
| EP | 2340770 A1 | 7/2011 |
| EP | 2240125 B1 | 6/2012 |
| EP | 2524653 A1 | 11/2012 |
| EP | 3292825 A1 | 3/2018 |
| JP | 06-013686 Y2 | 4/1994 |
| JP | 10-244611 A | 9/1998 |
| JP | 2000-505668 A | 5/2000 |
| JP | 2000-300571 A | 10/2000 |
| JP | 2002-513308 A | 5/2002 |
| JP | 2004-512153 A | 4/2004 |
| JP | 2004-534390 A | 11/2004 |
| JP | 2005-521447 A | 7/2005 |
| JP | 2005-521818 A | 7/2005 |
| JP | 2005-261597 A | 9/2005 |
| JP | 2006-230800 A | 9/2006 |
| JP | 2007-526087 A | 9/2007 |
| JP | 2007-535986 A | 12/2007 |
| JP | 2009-000497 A | 1/2009 |
| JP | 2009-512521 A | 3/2009 |
| JP | 2009-514624 A | 4/2009 |
| JP | 2009-160402 A | 7/2009 |
| JP | 2010-525896 A | 7/2010 |
| JP | 2012-519572 A | 8/2012 |
| KR | 2001-0040637 A | 5/2001 |
| RU | 2208400 C2 | 7/2003 |
| RU | 84711 U1 | 7/2009 |
| SU | 1377052 A1 | 2/1988 |
| WO | 93/19803 A1 | 10/1993 |
| WO | 96/01591 A1 | 1/1996 |
| WO | 96/25179 A1 | 8/1996 |
| WO | 96/31157 A1 | 10/1996 |
| WO | 96/40305 A1 | 12/1996 |
| WO | 97/42878 A1 | 11/1997 |
| WO | 98/07375 A1 | 2/1998 |
| WO | 98/08462 A2 | 3/1998 |
| WO | 98/16174 A1 | 4/1998 |
| WO | 98/18864 A1 | 5/1998 |
| WO | 98/29026 A2 | 7/1998 |
| WO | 98/51812 A2 | 11/1998 |
| WO | 99/05977 A1 | 2/1999 |
| WO | 99/18862 A1 | 4/1999 |
| WO | 99/18864 A1 | 4/1999 |
| WO | 99/18870 A1 | 4/1999 |
| WO | 99/18871 A1 | 4/1999 |
| WO | 99/30640 A1 | 6/1999 |
| WO | 99/39646 A1 | 8/1999 |
| WO | 99/66846 A1 | 12/1999 |
| WO | 00/12012 A1 | 3/2000 |
| WO | 00/17435 A1 | 3/2000 |
| WO | 00/27292 A1 | 5/2000 |
| WO | 00/44428 A1 | 8/2000 |
| WO | 00/51500 A1 | 9/2000 |
| WO | 01/03783 A1 | 1/2001 |
| WO | 01/08600 A2 | 2/2001 |
| WO | 01/17435 A1 | 3/2001 |
| WO | 01/19256 A1 | 3/2001 |
| WO | 01/21247 A1 | 3/2001 |
| WO | 01/28432 A1 | 4/2001 |
| WO | 01/30268 A1 | 5/2001 |
| WO | 01/49185 A1 | 7/2001 |
| WO | 01/72367 A1 | 10/2001 |

(56) References Cited

FOREIGN PATENT DOCUMENTS

| | | |
|---|---|---|
| WO | 01/78596 A1 | 10/2001 |
| WO | 01/93783 A2 | 12/2001 |
| WO | 02/17809 A1 | 3/2002 |
| WO | 02/24106 A2 | 3/2002 |
| WO | 02/38051 A2 | 5/2002 |
| WO | 03/01893 A2 | 1/2003 |
| WO | 03/05152 A2 | 1/2003 |
| WO | 03/24337 A1 | 3/2003 |
| WO | 03/53493 A2 | 7/2003 |
| WO | 03/59152 A2 | 7/2003 |
| WO | 03/61481 A1 | 7/2003 |
| WO | 03/63732 A2 | 8/2003 |
| WO | 03/77733 A2 | 9/2003 |
| WO | 03/82076 A2 | 10/2003 |
| WO | 2003/103476 A2 | 12/2003 |
| WO | 2004/012603 A2 | 2/2004 |
| WO | 2004/032993 A2 | 4/2004 |
| WO | 2004/037333 A1 | 5/2004 |
| WO | 2004/043266 A2 | 5/2004 |
| WO | 2004/043508 A1 | 5/2004 |
| WO | 2004/047649 A1 | 6/2004 |
| WO | 2004/052213 A1 | 6/2004 |
| WO | 2004/067092 A2 | 8/2004 |
| WO | 2004/101019 A2 | 11/2004 |
| WO | 2005/006990 A2 | 1/2005 |
| WO | 2005/018728 A2 | 3/2005 |
| WO | 2005/027752 A1 | 3/2005 |
| WO | 2005/032335 A2 | 4/2005 |
| WO | 2005/034724 A2 | 4/2005 |
| WO | 2005/074813 A1 | 8/2005 |
| WO | 2005/092203 A1 | 10/2005 |
| WO | 2005/110240 A1 | 11/2005 |
| WO | 2005/112779 A1 | 12/2005 |
| WO | 2006/036837 A2 | 4/2006 |
| WO | 2006/041612 A2 | 4/2006 |
| WO | 2006/062711 A2 | 6/2006 |
| WO | 2006/102213 A1 | 9/2006 |
| WO | 2007/124862 A2 | 11/2007 |
| WO | 2007/140797 A1 | 12/2007 |
| WO | 2008/002983 A1 | 1/2008 |
| WO | 2008/125689 A1 | 10/2008 |
| WO | 2008/137603 A2 | 11/2008 |
| WO | 2008/153872 A2 | 12/2008 |
| WO | 2008/156464 A1 | 12/2008 |
| WO | 2010/142051 A1 | 12/2010 |
| WO | 2011/044486 A1 | 4/2011 |
| WO | 2011/153548 A1 | 12/2011 |
| WO | 2012/003317 A1 | 1/2012 |

OTHER PUBLICATIONS

Bachthaler, "Corrosion of tungsten coils after peripheral vascular embolization therapy: influence on outcome and tungsten load," Catheter Cardiovasc Interv., Jul. 2004;62(3):380-384.
Chinese Search Report in Application No. 200980158768.9, dated Jun. 16, 2013, 4 pages.
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1) pp. 185-192, 2004.
International Preliminary Report on Patentability received for PCT Patent Application No. PCT/US2014/011980, mailed on Jul. 30, 2015, 22 pages.
International Search Report and Written Opinion for PCT/US2014/011980, dated Sep. 9, 2014, 32 pages.
Isotalo, T. et al., "Biocompatibility Testing of a New Bioabsorbable X-Ray Positive SR-PLA 96/4 Urethral Stent", The Journal of Uroloav. vol. 163, pp. 1764-1767, Nov. 1999.
Isotalo, T. et al., "Biocompatibility Testing of a New Bioabsorbable X-Ray Positive SR-PLA 96/4 Urethral Stent", The Journal of Urology, vol. 163, pp. 1764-1767, Nov. 1999.
Isotalo, T. et al., "Biocompatibility Testing of a New Bioabsorbable X-Ray Positive SR-PLA 96/4 Urethral Stent", The Journal of Urology. vol. 162, pp. 1764-1767, Nov. 1999.
Kilma, "Magnetic Vascular Port in minimally invasive direct coronary artery bypass grafting," Circulation, Sep. 14, 2004;110(11 Suppl 1):1155-60.
Kimura, A., et al., "Effects of Neutron Irradiation on the Transformation Behavior in Ti—Ni Alloys," Abstract, Proceedings of the Int'l Conf. on Mariensitic Transformations (1992) pp. 935-940.
Meier, MD, Bernhard et al., "Contemporary Management of Patent Formen Ovale."
Meier, MD, Bernhard, et al., "Contemporary Management of Patent Foramen Ovale," American Heart Association, Inc., Circulation, 2003, vol. 107, pp. 5-9.
Nat'l Aeronautics and Space Administration, "55-Nitinol—The Alloy with a Memory: Its Physical Metallurgy, Properties and Applications," NASA Report, pp. 24-25.
Parviainen, M. et al., "A New Biodegradable Stent for the Pancreaticojejunal Anastomosis After Pancreaticoduodenal Resection: In Vitro Examination and Pilot Experiences in Humans", Pancreas, vol. 21, No. 1, pp. 14-21, 2000.
Ramanathan, G., et al., "Experimental and Computational Methods for Shape Memory Alloys," 15.sup.th ASCE Engineering Mechanics Conf., Jun. 2-5, 2003.
Ruddy and McNally, "Rheological, Mechanical and Thermal Behaviour of Radiopaque Filled Polymers," ANTEC Papers: 2005, Polymer Processing Research Centre, School of Chemical Engineering, Queen's University of Belfast, Belfast UK, pp. 167-171, 2005.
Ruiz, et al., "The puncture technique: A new method for transcatheter closure of patent foramen ovale," Catheterization and Cardiovascular Interventions, 2001, vol. 53, pp. 369-372.
Schaffer and Gordon, "Engineering Characteristics of Drawn Filled Nitinol Tube" SMST-2003: Proceedings of the International Conference on Shape Memory and Superelastic Technologies (ASM International), pp. 109-118, 2004.
Shabalovskaya, "Surface, corrosion and biocompatibility aspects of Nitinol as an implant material," Biomed Mater Eng., 2002;12(1):69-109.
Smst-2000, "Proceedings of the International Conference on Shape Memory and Superelastic Technologies," 30 April to May 4, 2000, Asilomar Conference Proceedings, 2001, pp. 531-541.
Stein, "Telemanipulatory Application of a Magnetic Vascular Coupler on the Beating Heart with the da Vinci.TM. surgical system," Biomedizinische Technik, 2003, vol. 48(9), pp. 230-234, Eng. Abst included.
Stein, H., "Telemanipulator-gestutzte Applikation eines magnetischen Gefa.beta .- Kopplers am schlagenden Herzen mit dem da Vinci. TM.—Surgical-System," [Telemanipulatory Application of a Magnetic Vascular Coupler on the Beating Heart with the da Vinci TM surgical system.] Biomedizinische Technik, 2003, vol. 48(9), pp. 230-234. [English abstract].
Stockel, "Nitinol Medical Devices and Implants," Min Invas Ther & Allied Technol 9(2), Cordis Corporation—Nitino/Devices and Components, Fremont, CA, USA, 2000pp. 81-88.
Stockel, "Nitinol Medical Devices and Implants," SMST-2000 Conference Proceedings, 2001, pp. 531-541.
Uchil, J. "Shape Memory Alloys—Characterization Techniques," Pramana—Journal of Physics, (2002) vol. 58, Nos. 5 & 6, pp. 1131-1139.
Vaajanen et al., "Expansion and fixation properties of a new braided biodegradable urethral stent: an experimental study in the rabbit," The Journal of Urology, J Ural., Mar. 2003; 169(3):1171-1174.
European Search Report for EP Patent Application No. 24159097.5, Issued on Jun. 24, 2024, 10 pages.

Load the Device

| | Clinician movement | Component movement |
|---|---|---|
| Step 1 | Flush the delivery system with saline | Attach a saline filled syringe to the flushing port and push in saline until it comes out the distal end of the delivery system |
| Step 2 | Move the first linear actuator to the right edge of the slot | The first linear actuator moves in slot to the right pressing on the spring<br>The mandrel control lever rotates on slider rod to the right<br>A first linear actuator is free of the distal notch in the sizing insert<br>The second tube is prevented from moving |
| Step 3 | Move the first linear actuator proximally | The first tube moves proximally<br>The device proximal end moves proximally elongating the device |
| Step 4 | Move the first linear actuator proximally until device is loaded in delivery catheter | The spring pushes the first linear actuator and mandrel control lever to the left into the proximal notch in the sizing insert<br>The second tube is now free to move proximally with the device and the first tube<br>The second tube, device and first tube slide into delivery catheter |
| Step 5 | Flush the delivery system with saline | Attach a saline filled syringe to the flushing port and push in saline until it comes out the distal end of the delivery system |

FIG. 9A

Deploy Device

| | Clinician movement | Component movement |
|---|---|---|
| Step 1 | Move the first linear actuator distally until it stops | The first tube and second tube move distally in the third tube |
| Step 2 | Move the first linear actuator to the right | The first linear actuator moves in the slot to the right, pressing on the spring<br>The mandrel control lever rotates on the slider rod to the right<br>The first linear actuator is free of the proximal notch in the sizing insert |
| Step 3 | Move the first linear actuator distally | The first tube moves distally<br>The proximal eyelet of the device moves distally<br>The distal end of device is stopped in place<br>The first tube guides the device out of the third tube to deploy |
| Step 4 | Move the first linear actuator to the distal most point in slot | The device is free of the third tube<br>The first linear actuator is at a distal most point in slot<br>The mandrel control lever is pushed to the left of the slot by the spring<br>The first linear actuator is in the forward notch in the sizing insert |

FIG. 9B

Lock the device

| | Clinician movement | Component movement |
|---|---|---|
| Step 1 | Flip up the retrieval cord lock in the first linear actuator | The retrieval cord lock flips up |
| Step 2 | Grasp the second linear actuator and press it | The second linear actuator becomes free of the corrugations in slot<br>The third tube is attached to the second linear actuator |
| Step 3 | Move the second linear actuator proximally | The third tube moves proximally<br>The mandrel control lever moves proximally<br>The sizing insert moves proximally<br>The second tube moves proximally from between the eyelets of the device |
| Step 4 | Twist the retrieval cord lock then pull on the retrieval cord lock until the retrieval cord comes out of the handle | The retrieval cord is attached to the retrieval cord lock at one end<br><br>Pulling removes the cord from the device through a lumen of the first tube<br>The device is permanently deployed |

FIG. 9C

Device Retrieval

| | Clinician movement | Component movement |
|---|---|---|
| Step 1 | Flip the retrieval lock lever down | The retrieval cord is locked |
| Step 3 | Unscrew the retrieval luer | The delivery catheter is separated from the handle |
| Step 4 | Hold the delivery catheter and pull the entire handle assembly proximally | The handle, first tube and second tube move proximally<br>The device proximal end moves proximally elongating the device<br><br>The device is withdrawn proximally into the delivery catheter |

FIG. 9D

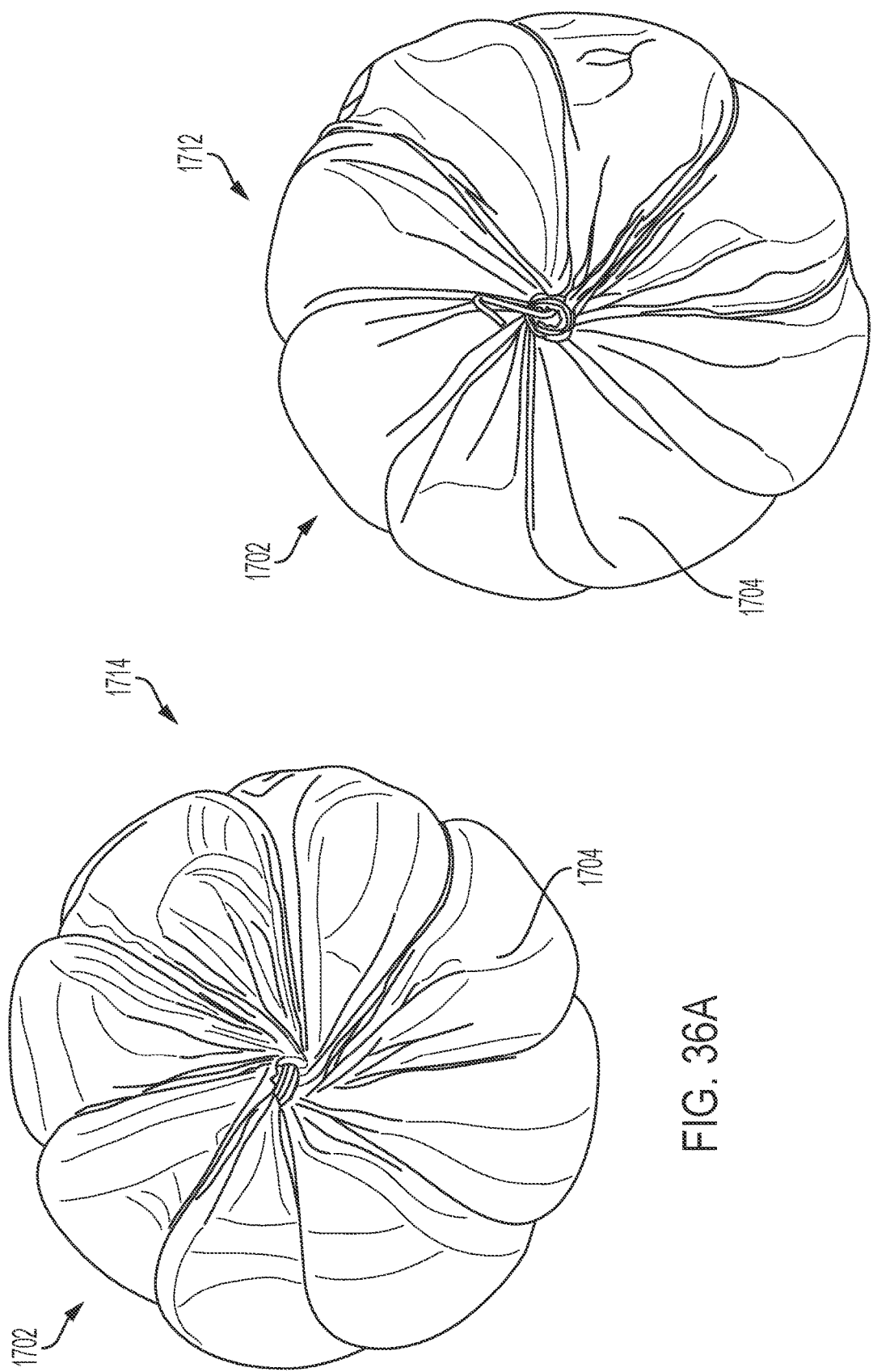

SEALING DEVICE AND DELIVERY SYSTEM

CROSS-REFERENCE TO RELATED APPLICATION

This application is a continuation of U.S. patent application Ser. No. 16/405,508, filed May 7, 2019, which is a continuation of U.S. patent application Ser. No. 13/838,166, filed Mar. 15, 2013, which claims the benefit of U.S. Provisional Application 61/754,504, filed Jan. 18, 2013, all of which are incorporated herein by reference in their entireties for all purposes.

FIELD OF THE INVENTION

This disclosure relates to sealing devices for repair of a cardiac or vascular defect or tissue opening, and to delivery systems for delivering and deploying the sealing devices.

BACKGROUND OF THE INVENTION

Occluding device implantation by open-heart surgery has historically been used to treat cardiac defects or tissue openings. More recently, to avoid the trauma and complications associated with open-heart surgery, a variety of trans-catheter closure techniques have been developed. In such techniques, an occluding device is delivered through a catheter to the site of the opening or defect, where it is deployed.

A variety of trans-catheter-delivered devices are known, including devices that require assembly at the site of the tissue opening or require threading or "buttoning" of discrete device elements. Other devices include self-expanding devices. An example of a self-expanding device includes an occlusion bag, a tube, a guide catheter, a super elastic wire, a release mechanism, and a delivery sheath. The super elastic wire is attached to the release mechanism and the wire, and the release mechanism, occlusion bag, guide catheter and tube are inserted into the delivery sheath for transport to an aperture. After delivery, the occlusion bag is placed within the aperture and the wire is deployed within the bag. The bag and wire are repositioned, if necessary, and the release mechanism is activated to release the wire.

Another example of a self-expanding device includes a shape-set tubular metal fabric device and, optionally, an occluding fiber included in the hollow portions of the device. The metal fabric defines a medical device shaped like a bell, which can be collapsed for passage through a catheter for deployment in a channel of a patient's body.

Most trans-catheter delivery devices are deployed using one of two basic techniques: pulling back an outer catheter to release the device, or pushing the device free of the catheter with a push rod. Each of these systems utilizes a handle to actuate the mechanism used to deploy the device. An example of such a system includes a flexible urging member for urging the sealing device through the catheter and a remotely located control means for advancing the urging member. In this example, the control means includes a threaded, tubular shaft connected to the urging member and a manually rotatable threaded rotor mounted on the shaft. The threads on the rotor mate with the threads on the shaft so that the rotation of the rotor through a known angle will advance the shaft and the urging member a known distance.

An example of a system that utilizes a pull back outer shaft or catheter includes a handle that may selectively hold the delivery system components at any configuration during deployment and positioning of the device. The outer catheter of such a system is pulled back to release the device by actuating a sliding lever and a rotating finger ring on the delivery system handle.

SUMMARY OF THE INVENTION

In a first general aspect, a medical device for sealing a defect in a body includes a wire frame that includes six wires that each extend from a proximal end of the wire frame to a distal end of the wire frame. The wires form a first eyelet near the proximal end of the wire frame and a second eyelet near the distal end of the wire frame, where the first eyelet is formed from first end portions of each wire of the six wires, and the second eyelet is formed from second end portions of each wire of the six wires. The wires also form a first occluding member that includes, for each wire of the six wires, a first generally linear segment and a first generally curved segment that together define a petal of the first occluding member, where the first occluding member is disposed adjacent the first eyelet. The wires further form a second occluding member that includes, for each wire of the six wires, a second generally linear segment and a second generally curved segment that together define a petal of the second occluding member, where the second occluding member is disposed adjacent the second eyelet. The wires further form a defect-occupying portion disposed between the first occluding member and the second occluding member, where each wire of the six wires includes, in the defect-occupying portion, a third generally linear segment, a fourth generally linear segment, and a third curved segment disposed between the third generally linear segment and the fourth generally linear segment. The defect-occupying portion is adapted to substantially fill a range of potential defect sizes from a largest defect size to a smallest defect size that is approximately 60% of the largest defect size, and the defect-occupying portion deflects to an outer diameter that is less than about 60% of its nominal outer diameter when a radial pressure of about 0.04 N/mm$^2$ is applied to the defect occupying portion. The device also includes a sealing member in contact with the frame, and a non-metal attachment member adapted to couple with one or more components of a delivery system.

In various implementations, the first occluding member may be adapted to conform to a geometry of a first tissue surface and the second occluding member may be adapted to conform to a geometry of a second tissue surface. The petal of the first occluding member may be adapted to bear a load associated with the first tissue surface without imparting a substantial force to the other wires of the six wires, and the petal of the second occluding member may be adapted to bear a load associated with the second tissue surface without imparting a substantial force to the other wires of the six wires. The sealing member may be attached to an exterior of the frame, or to an interior of the frame. The sealing member may substantially encapsulate the frame or may partially encapsulate the frame.

In a second general aspect, a medical device for sealing a defect or structure in a heart includes a wire frame that includes eight wires that each extend from a proximal end of the wire frame to a distal end of the wire frame. The wires form a first eyelet near the proximal end of the wire frame and a second eyelet near the distal end of the wire frame, where the first eyelet is formed from first end portions of each wire of the eight wires, and the second eyelet is formed from second end portions of each wire of the eight wires. The wires also form a first occluding member that includes, for each wire of the eight wires, a first generally linear segment and a first generally curved segment that together define a petal of the first occluding member, where the first occluding member is disposed adjacent the first eyelet. The wires further form a second occluding member that includes, for each wire of the eight wires, a second generally linear segment and a second generally curved segment that together define a petal of the second occluding member, where the second occluding member is disposed adjacent the second eyelet. The wires further form a defect-occupying portion disposed between the first occluding member and the second occluding member, where each wire of the eight wires includes, in the defect-occupying portion, a third generally linear segment, a fourth generally linear segment, and a third curved segment disposed between the third generally linear segment and the fourth generally linear segment. The defect-occupying portion is adapted to substantially fill a range of potential defect sizes from a largest defect size to a smallest defect size that is approximately 60% of the largest defect size, and the defect-occupying portion deflects to an outer diameter that is less than about 60% of its nominal outer diameter when a radial pressure of about 0.04 N/mm$^2$ is applied to the defect occupying portion. The device also includes a sealing member in contact with the frame, and a non-metal attachment member adapted to couple with one or more components of a delivery system.

In a third general aspect, a medical device for sealing a defect or structure in a heart includes a wire frame that includes a plurality of wires that each extend from a proximal end of the wire frame to a distal end of the wire frame. The wires form a first wire aggregation element near the proximal end of the wire frame and a second wire aggregation element near the distal end of the wire frame, where the first wire aggregation element is formed from first end portions of each wire of the plurality of wires, and the second wire aggregation element is formed from second end portions of each wire of the plurality of wires. The wires also form a first occluding member that includes, for each wire of the plurality of wires, a first generally linear segment and a first generally curved segment that together define a petal of the first occluding member, where the first occluding member is disposed adjacent the first wire aggregation element. The wires further form a second occluding member that includes, for each wire of the plurality of wires, a second generally linear segment and a second generally curved segment that together define a petal of the second occluding member, where the second occluding member is disposed adjacent the second wire aggregation element. The wires further form a defect-occupying portion disposed between the first occluding member and the second occluding member, where each wire of the plurality of wires includes, in the defect-occupying portion, a third generally linear segment, a fourth generally linear segment, and a third curved segment disposed between the third generally linear segment and the fourth generally linear segment. The defect-occupying portion is adapted to substantially fill a range of potential defect sizes from a largest defect size to a smallest defect size that is approximately 60% of the largest defect size, and the defect-occupying portion deflects to an outer diameter that is less than about 60% of its nominal outer diameter when a radial pressure of about 0.04 N/mm$^2$ is applied to the defect occupying portion. The device also includes a sealing member in contact with the frame.

In a fourth general aspect, a medical device for sealing a defect or structure in a heart includes a wire frame that includes a plurality of wires that each extend from a proximal end of the wire frame to a distal end of the wire frame. The wires form a first wire aggregation element near the proximal end of the wire frame and a second wire aggregation element near the distal end of the wire frame, where the first wire aggregation element is formed from first end portions of each wire of the plurality of wires, and the second wire aggregation element is formed from second end portions of each wire of the plurality of wires. The wires also form a first occluding member that includes, for each wire of the plurality of wires, a first generally linear segment and a first generally curved segment that together define a petal of the first occluding member, where the first occluding member is disposed adjacent the first wire aggregation element. The wires also form a second occluding member that includes, for each wire of the plurality of wires, a second generally linear segment and a second generally curved segment that together define a petal of the second occluding member, where the second occluding member is disposed adjacent the second wire aggregation element. The wires further form a defect-occupying portion disposed between the first occluding member and the second occluding member, wherein each wire of the plurality of wires includes, in the defect-occupying portion, a third generally linear segment, a fourth generally linear segment, and a third curved segment disposed between the third generally linear segment and the fourth generally linear segment. The defect-occupying portion is adapted to substantially fill a range of potential defect sizes from a largest defect size to a smallest defect size, the range being at least about 7 mm. The device also includes a sealing member in contact with the frame.

In a fifth general aspect, a medical device for sealing a defect or structure in a heart includes a wire frame that includes a plurality of wires that each extend from a proximal end of the wire frame to a distal end of the wire frame. The wires form a first wire aggregation element near the proximal end of the wire frame and a second wire aggregation element near the distal end of the wire frame, where the first wire aggregation element is formed from first end portions of each wire of the plurality of wires, and the second wire aggregation element is formed from second end portions of each wire of the plurality of wires. The wires also form a first occluding member that includes, for each wire of the plurality of wires, a first generally linear segment and a first generally curved segment that together define a petal of the first occluding member, where the first occluding member is disposed adjacent the first wire aggregation element. The wires also form a second occluding member that includes, for each wire of the plurality of wires, a second generally linear segment and a second generally curved segment that together define a petal of the second occluding member, where the second occluding member is disposed adjacent the second wire aggregation element. The wires further form a defect-occupying portion disposed between the first occluding member and the second occluding member, wherein each wire of the plurality of wires includes, in the defect-occupying portion, a third generally linear segment, a fourth generally linear segment, and a third curved segment disposed between the third generally linear segment and the fourth generally linear segment. The defect-occupying portion is adapted to not provide substantial apposition force against the defect. The device also includes a sealing member in contact with the frame.

In a sixth general aspect, a medical device for sealing a defect or structure in a heart includes a wire frame that includes a plurality of wires that each extend from a proximal end of the wire frame to a distal end of the wire frame. The wires form a first wire aggregation element near the proximal end of the wire frame and a second wire aggregation element near the distal end of the wire frame, where the first wire aggregation element is formed from first end portions of each wire of the plurality of wires, and the second wire aggregation element is formed from second end portions of each wire of the plurality of wires. The wires also form a first occluding member disposed adjacent the first wire aggregation element, and a second occluding member disposed adjacent the second wire aggregation element. The wires further form a defect-occupying portion disposed between the first occluding member and the second occluding member, wherein each wire of the plurality of wires includes, in the defect-occupying portion, a first generally linear segment, a second generally linear segment, and a curved segment disposed between the first generally linear segment and the second generally linear segment. The defect-occupying portion is adapted to not provide substantial apposition force against the defect. The device also includes a sealing member in contact with the frame.

In a seventh general aspect, an implantable medical device for sealing an aperture in tissue includes a frame that includes: a) a first occluding member that is adapted to conform to a geometry of a first tissue surface and to provide an apposition force against the first tissue surface, b) a second occluding member that is adapted to conform to a geometry of a second tissue surface and to provide an apposition force against the second tissue surface, and c) a defect-occupying member disposed between the first occluding member and the second occluding member and adapted to not provide substantial apposition force against tissue around the aperture. The frame is defined by a plurality of elongate members, each of which includes: a first portion that defines a petal of the first occluding member, a second portion that defines a petal of the second occluding member, and a third portion, disposed between the first portion and the second portion, wherein the third portion includes a first generally linear segment, a second generally linear segment, and a curved segment disposed between the first generally linear segment and the second generally linear segment. The device also includes a sealing member in contact with the frame, and a non-metal attachment member adapted to couple with one or more components of a delivery system.

In an eighth general aspect, an implantable medical device for sealing a defect that extends between a first tissue surface and a second tissue surface includes a frame that includes: a) a first occluding member that is adapted to conform to a geometry of the first tissue surface and to provide an apposition force against the first tissue surface, b) a second occluding member that is adapted to conform to a geometry of the second tissue surface and to provide an apposition force against the second tissue surface, and c) a defect-occupying member disposed between the first occluding member and the second occluding member and adapted to not provide substantial apposition force against the defect. The frame is defined by a plurality of elongate members, each of which includes: a first portion that defines a petal of the first occluding member, a second portion that defines a petal of the second occluding member, and a third portion, disposed between the first portion and the second portion, wherein the third portion includes a first generally linear segment, a second generally linear segment, and a curved segment disposed between the first generally linear segment and the second generally linear segment. The device also includes a sealing member in contact with the frame, and a non-metal attachment member adapted to couple with one or more components of a delivery system.

In a ninth general aspect, an implantable medical device for sealing a defect that extends between a first tissue surface and a second tissue surface includes a frame that includes a first occluding member, a second occluding member, and a defect-occupying member between the first occluding member and the second occluding member. The frame is defined by a plurality of elongate members, and each elongate member of the plurality of elongate members includes: a first portion that defines a petal of the first occluding member, a second portion that defines a petal of the second occluding member, and a third portion, disposed between the first portion and the second portion, wherein the third portion defines an inflection region of the defect-occupying member. The device also includes a sealing member that substantially covers the frame, and an attachment member adapted to couple with one or more components of a delivery system.

In a tenth general aspect, a medical device for sealing a defect or structure in a heart includes a wire frame that includes a plurality of wires that form a first occluding member and a second occluding member. The wire frame includes a defect-occupying portion disposed between the first occluding member and the second occluding member, wherein the defect-occupying portion is adapted to not significantly deform the defect; and wherein the defect-occupying portion is adapted to fill a range of potential defect sizes from a largest defect size to a smallest defect size, the range being at least about 7 mm.

In an eleventh general aspect, a medical device for sealing a defect or structure in a heart includes a wire frame that includes a plurality of wires that form a first occluding member and a second occluding member. The wire frame includes a defect-occupying portion disposed between the first occluding member and the second occluding member. The defect-occupying portion is adapted to fill a wide range of potential defect sizes such that no more than five devices of a range of sizes are required to effectively seal a range of nominal defect sizes of approximately 8 to 35 mm.

In a twelfth general aspect, a medical device for sealing a defect or structure in a heart includes a wire frame that includes a plurality of wires that form a first occluding member and a second occluding member. The wire frame includes a defect-occupying portion disposed between the first occluding member and the second occluding member. The defect-occupying portion is adapted to not significantly deform the defect, and is adapted to fill a range of potential defect sizes from 8 to 15 mm.

In a thirteenth general aspect, a medical device for sealing a defect or structure in a heart includes a wire frame that includes a plurality of wires that form a first occluding member and a second occluding member. The wire frame includes a defect-occupying portion disposed between the first occluding member and the second occluding member. The defect-occupying portion is adapted to not significantly deform the defect, and is adapted to fill a range of potential defect sizes from 13 to 20 mm.

In a fourteenth general aspect, a medical device for sealing a defect or structure in a heart includes a wire frame that includes a plurality of wires that form a first occluding member and a second occluding member. The wire frame includes a defect-occupying portion disposed between the first occluding member and the second occluding member. The defect-occupying portion is adapted to not significantly deform the defect, and is adapted to fill a range of potential defect sizes from 18 to 25 mm.

In a fifteenth general aspect, a medical device for sealing a defect or structure in a heart includes a wire frame that includes a plurality of wires that form a first occluding member and a second occluding member. The wire frame includes a defect-occupying portion disposed between the first occluding member and the second occluding member. The defect-occupying portion is adapted to not significantly deform the defect, and is adapted to fill a range of potential defect sizes from 23 to 30 mm.

In a sixteenth general aspect, a medical device for sealing a defect or structure in a heart includes a wire frame that includes a plurality of wires that form a first occluding member and a second occluding member. The wire frame includes a defect-occupying portion disposed between the first occluding member and the second occluding member. The defect-occupying portion is adapted to not significantly deform the defect, and is adapted to fill a range of potential defect sizes from 28 to 35 mm.

In a seventeenth general aspect, a method of sealing a defect or structure in a heart includes providing a medical device that includes a wire frame that includes a plurality of wires that each extend from a proximal end of the wire frame to a distal end of the wire frame. The wires form a first wire aggregation element near the proximal end of the wire frame and a second wire aggregation element near the distal end of the wire frame, where the first wire aggregation element is formed from first end portions of each wire of the plurality of wires, and the second wire aggregation element is formed from second end portions of each wire of the plurality of wires. The wires also form a first occluding member that includes, for each wire of the plurality of wires, a first generally linear segment and a first generally curved segment that together define a petal of the first occluding member, where the first occluding member is disposed adjacent the first wire aggregation element. The wires also form a second occluding member that includes, for each wire of the plurality of wires, a second generally linear segment and a second generally curved segment that together define a petal of the second occluding member, where the second occluding member is disposed adjacent the second wire aggregation element. The wires further form a defect-occupying portion disposed between the first occluding member and the second occluding member, wherein each wire of the plurality of wires includes, in the defect-occupying portion, a third generally linear segment, a fourth generally linear segment, and a third curved segment disposed between the third generally linear segment and the fourth generally linear segment. The defect-occupying portion is adapted to substantially fill a range of potential defect sizes from a largest defect size to a smallest defect size that is approximately 60% of the largest defect size, and wherein the defect-occupying portion deflects to an outer diameter that is less than about 60% of its nominal outer diameter when a radial pressure of about 0.04 N/mm² is applied to the defect occupying portion. The device also includes a sealing member in contact with the frame. The method also includes advancing a delivery apparatus, to which the medical device is attached, to a location of the defect or structure in the heart, and deploying the medical device at the location of the defect or structure to seal the defect or structure.

In an eighteenth general aspect, a method of sealing a defect or structure in a heart includes providing a medical device that includes a wire frame that includes a plurality of wires that each extend from a proximal end of the wire frame to a distal end of the wire frame. The wires form a first wire aggregation element near the proximal end of the wire frame and a second wire aggregation element near the distal end of the wire frame, where the first wire aggregation element is formed from first end portions of each wire of the plurality of wires, and the second wire aggregation element is formed from second end portions of each wire of the plurality of wires. The wires also form a first occluding member that includes, for each wire of the plurality of wires, a first generally linear segment and a first generally curved segment that together define a petal of the first occluding member, where the first occluding member is disposed adjacent the first wire aggregation element. The wires also form a second occluding member that includes, for each wire of the plurality of wires, a second generally linear segment and a second generally curved segment that together define a petal of the second occluding member, where the second occluding member is disposed adjacent the second wire aggregation element. The wires further form a defect-occupying portion disposed between the first occluding member and the second occluding member, wherein each wire of the plurality of wires includes, in the defect-occupying portion, a third generally linear segment, a fourth generally linear segment, and a third curved segment disposed between the third generally linear segment and the fourth generally linear segment. The defect-occupying portion is adapted to substantially fill a range of potential defect sizes from a largest defect size to a smallest defect size, the range being at least about 7 mm. The device also includes a sealing member in contact with the frame. The method also includes advancing a delivery apparatus, to which the medical device is attached, to a location of the defect or structure in the heart, and deploying the medical device at the location of the defect or structure to seal the defect or structure.

In a nineteenth general aspect, a method of sealing a defect or structure in a heart includes providing a medical device that includes a wire frame that includes a plurality of wires that form a first occluding member and a second occluding member. The wire frame includes a defect-occupying portion disposed between the first occluding member and the second occluding member, wherein the defect-occupying portion is adapted to not significantly deform the defect; and wherein the defect-occupying portion is adapted to fill a range of potential defect sizes from a largest defect size to a smallest defect size, the range being at least about 7 mm. The method also includes advancing a delivery apparatus, to which the medical device is attached, to a location of the defect or structure in the heart, and deploying the medical device at the location of the defect or structure to seal the defect or structure.

Other aspects, features, and advantages will be apparent from the description, the drawings, and the claims.

BRIEF DESCRIPTION OF THE DRAWINGS

FIG. 9A-D are flow charts describing the operation of the delivery system.

FIGS. 36A and 36B are end view of the example sealing device of FIG. 35.

DETAILED DESCRIPTION OF THE ILLUSTRATED EMBODIMENTS

A first embodiment provides a sealing device having an expandable frame formed from a plurality of wires extending from a proximal end to a distal end of the frame with the wires forming a proximal and distal eyelet with a sealing member at least partially encapsulating the expandable wire frame.

Figure 1:
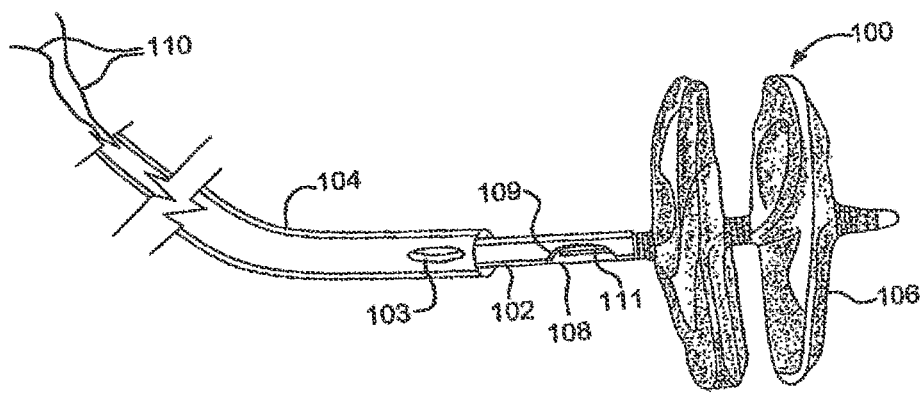
FIG. 1 is a perspective view of a deployed sealing device attached to the distal end of a delivery system.

FIG. 1 shows one embodiment of sealing device 100. Sealing device 100 will be discussed in detail in a later section. Sealing device 100 may housed within third tube 104. Third tube 104 contains sealing device 100, first tube 102, second tube 108, retrieval cord 110 and locking loop 111. Third tube 104 may be manufactured of Pebax® or any other material with suitable biocompatible and mechanical properties. A material choice with radiopacity may also be an option. The third tube 104 may be manufactured with or without a reinforcing braid to provide appropriate kink resistance and strength for the chosen application. Third tube 104 may also be designed with or without a radiopaque marker band. The design and materials of third tube 104 may be chosen for other properties such as torquability, steerability and vascular trauma reduction. One skilled in the art will appreciate that there are a wide variety of potential materials that may be used to facilitate the present invention. The third tube 104 may be of any size but is preferably 10fr. with an inner diameter of about 0.048 mm and an outer diameter of about 0.33 mm. Third tube 104 may be used with or without a guidewire and may include a rapid exchange port 103. The tip of first tube 104 is preferably curved to aid in navigation and delivery of sealing device 100 from the access site to the defect with or without a guidewire.

Also shown in FIG. 1 is first tube 102. As previously stated, first tube 102 may be housed within third tube 104. The first tube 102 may be of any outer diameter size but is preferably sized to fit within the lumen of the third tube 104. First tube 102 may be manufactured of Pebax® or any other material with suitable biocompatible and mechanical properties. First tube 102 is preferably a triple lumen catheter. The lumens may be of any geometric shape but are preferably round or oval or a combination of both. First tube 102 may be used to position and aid in the deployment of sealing device 100. First tube 102 may be utilized in conjunction with second tube 108 to cause sealing device 100 to protrude from the distal tip of third tube 104 once sealing device 100 has reached the defect site. The first tube 102 may also have the function of retaining sealing device 100 onto the delivery system until final device deployment. First tube 102 has an opening 109 in the distal most end to allow the locking loop 111 to protrude during device deployment. The opening 109 and protruding locking loop 111 provide attachment to the device delivery system. Locking loop 111 is shown in its extended position prior to retaining its pre-set shape. The first tube 102 may be surface treated or coated to enhance the material's biocompatibility or alter or enhance the surface friction.

First tube 102 may house the second tube 108. The second tube 108 is essentially tubular with an oval cross section and can have an outer diameter suitable to fit inside first tube 102. A preferred outer diameter range would be from about 1.27×0.68 mm and would be flared at the distal end. The second tube 108 may be fabricated from any suitable biocompatible material including polymers or metals. A preferable material would be PEEK (polyetheretherketone). Second tube 108 can be used to aid in the delivery and deployment of sealing device 100 to a defect site. Second tube 108 is threaded through the eyelets of sealing device 100 to hold sealing device 100 on the delivery system and to provide stability while deploying the sealing device 100. Sealing device eyelets will be discussed further.

Retrieval cord 110 is looped through two of the smaller lumens of the first tube 102 and through the proximal eyelet of the sealing device 100 to provide attachment to the delivery system and a method of retrieval once the sealing device has been deployed. Retrieval cord 110 extends through the length of first tube 102 with the ends terminating at the handle used for deploying sealing device 100. Retrieval cord 110 may be manufactured of any biocompatible material of sufficient strength and size. A preferable material is ePTFE (expanded polytetrafluoroethylene).

Figure 2A:
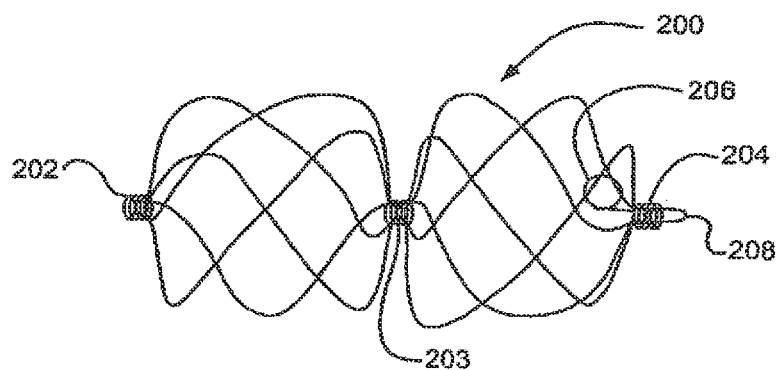
FIG. 2A is a view of an expanded frame of a sealing device.

As shown in FIG. 2A sealing device 100 is formed of a wire frame 200. When situated for delivery, wire frame 200 is at an extended position on second tube 108 and within third tube 104. Wire frame 200 may be of any size appropriate for an application but is preferably sized with finished outer diameters of 15, 20, 25, or 30 mm. The wire frame 200 is formed of continuous wires. Any number of wires may be used to construct the wire frame 200. A preferable number of wires is five. The wire frame 200 can be constructed of wires that have elastic properties that allow for wire frame 200 to be collapsed for catheter based delivery or thoracoscopic delivery, and self-expand to a "memory" induced configuration once positioned in a defect. The elastic wire may be a spring wire, or a shape memory NiTi (nitinol) alloy wire or a super-elastic NiTi alloy wire. The elastic wire may also be of a drawn-filled type of NiTi containing a different metal at the core. Preferably, wire frame 200 would be constructed of a drawn-filled type of NiTi wire containing a radiopaque metal at the center. Upon deployment, the wire structure resumes its deployed shape without permanent deformation.

Figure 2B:
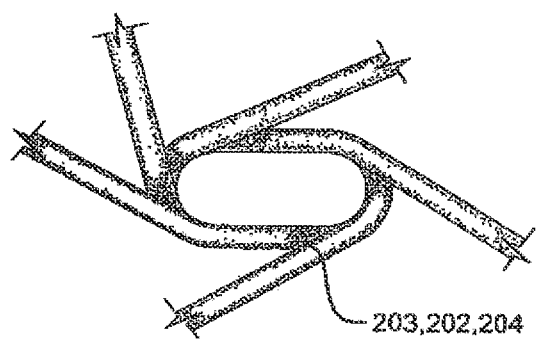
FIG. 2B is an end on view of an eyelet of a sealing device.

Wire frame 200 and other wire frames shown are formed from elastic wire materials that have outer diameters between 0.12 and 0.4 mm. In a preferable embodiment, wire outer diameter size would be about 0.3 mm. When formed, wire frame 200 comprises a distal bumper 208, distal eyelet 204, locking loop 206, an optional center eyelet 203, and proximal eyelet 202. FIG. 2B shows the position of elastic wires during the formation of eyelets 202, 203 and 204 of wire frame 200.

Figure 2C:
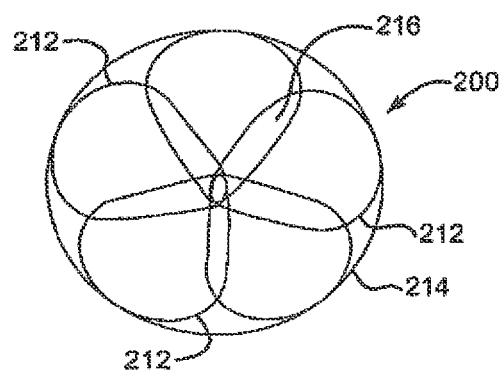
FIG. 2C is an end on view of a frame of a sealing device.

FIG. 2C shows a disk formed when wire frame 200 is deployed. The elastic wires that form wire frame 200 form petals 212 during deployment. The pre-set elastic wire configuration of wire frame 200 allows the frame to twist during deployment. This twist forms petals 212. Deployed petals 212 form the outer diameter 214 of the wire frame 200. Deployed petals 212, when covered with sealing member 106, form proximal and distal disks, to be discussed further. Petals 212 are optimally formed to have overlapping zones 216 to improve sealing qualities. The radius of petals 212 may be maximized to minimize sharp bend angles in the elastic wire and to minimize unsupported sections of petals 212 that improve sealing qualities of the device, reduce bending fatigue in the wire and aid in reducing device loading forces. Deployed petals 212 form a disk on either side of the center eyelet 203. The deployed configuration will be discussed further.

Figure 3A:
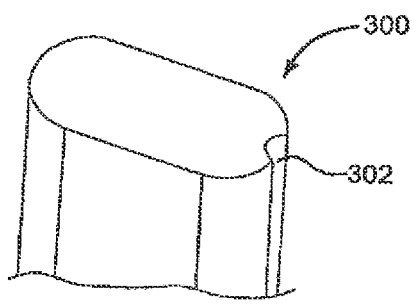
FIGS. 3A-C are views of components of a winding jig.
Figure 3B:
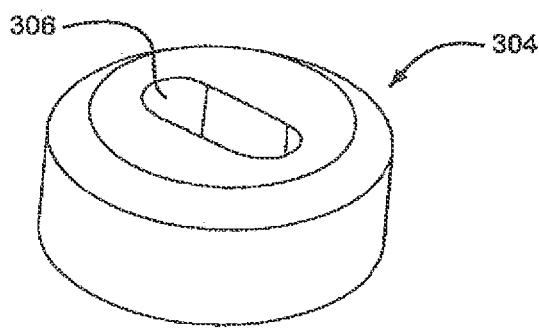
Figure 3C:
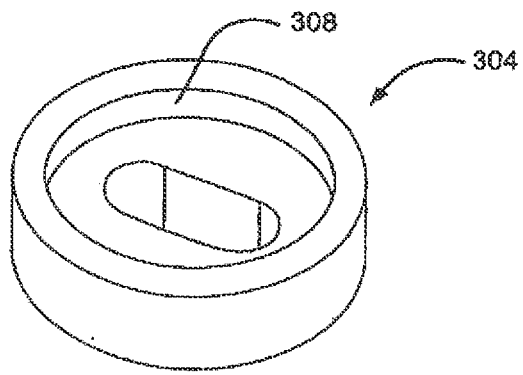

Construction of wire frame 200 may be accomplished by a variety of means including machine winding with automatic wire tensioning or by hand winding with weights suspended from each wire during construction. Shown in FIGS. 3A-C are keyed center pin 300 and button 304, which may be used to aid in the construction of wire frame 200. One commonly skilled in the art would recognize that there are many materials suitable for use as a manufacturing aid or tooling. A preferable material for use in forming a center pin 300 would be cobalt high strength steel. A preferable material for use in forming a button 304 and winding jig would be corrosion resistant tool steel. The winding jig will be discussed further. Shown in detail in FIG. 3A, keyed center pin 300 may have groove 302, which can be used to secure an elastic wire during device construction. Keyed center pin 300 can be used to guide an elastic wire through opening 306 in button 304, the features of which are illustrated in FIGS. 3B-C. Button 304 is preferably formed with an indention 308 in the bottom to fit securely in a winding jig. An elastic wire held in groove 302 and inserted through opening 306 in button 304 can form a bumper 208 and locking loop 206. Keyed center pin 300 is also used in the formation of eyelets 202, 203 and 204. During device construction, after the formation of bumper 208, elastic wires can be wound around keyed center pin 300 to form a distal eyelet 202. Other eyelets, 203 and 204 can be formed in a similar manner. Once keyed center pin 300 is inserted in button 304 an elastic wire may be inserted into grooves in a winding jig.

Figure 4A:
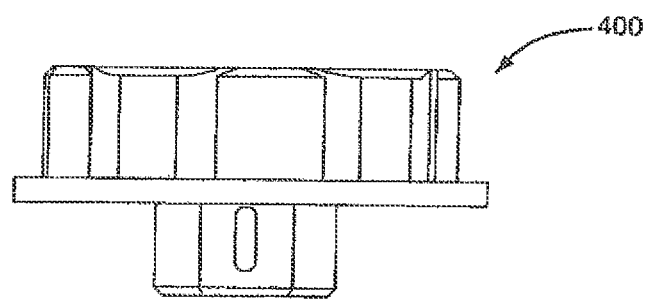
FIG. 4A is a side view of a winding jig.
Figure 4B:
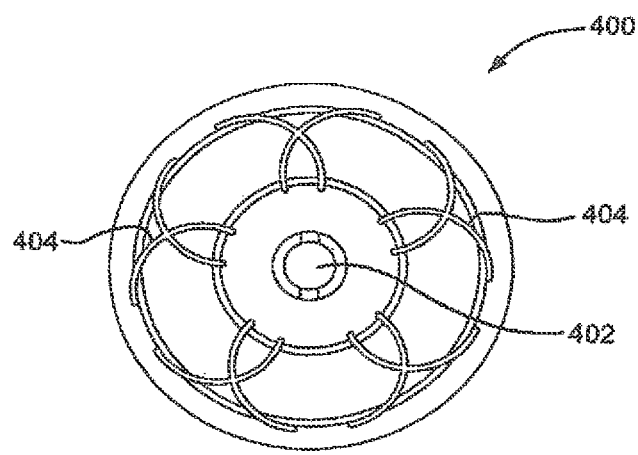
FIG. 4B is a top view of a winding jig.

A winding jig may be used to secure and form the elastic wires during construction and processing of the sealing device 100. A typical winding jig may be constructed as commonly known in the arts. Materials used for construction of such a winding jig have been discussed previously. A preferable winding jig is shown in FIGS. 4A and 4B. FIG. 4A illustrates a side view of the winding jig 400. FIG. 4B shows a view of the top of a preferable winding jig 400. Winding jig 400 contains an aperture 402 that may be shaped and sized to hold keyed center pin 300 and button 304 during device construction. Grooves 404 in the jig surface are used to secure and form the elastic wires into petals 212. Grooves 404 may be of any diameter but are preferably sized to accommodate an outer diameter of elastic wire. In one embodiment shown in FIG. 5A, the winding jig assembly may be used to form a center eyelet 203, a petal assembly and proximal eyelet 204. The shaped wire may be constrained in the winding jig assembly, heated and processed to shape set as commonly known in the arts.

Figure 5A:
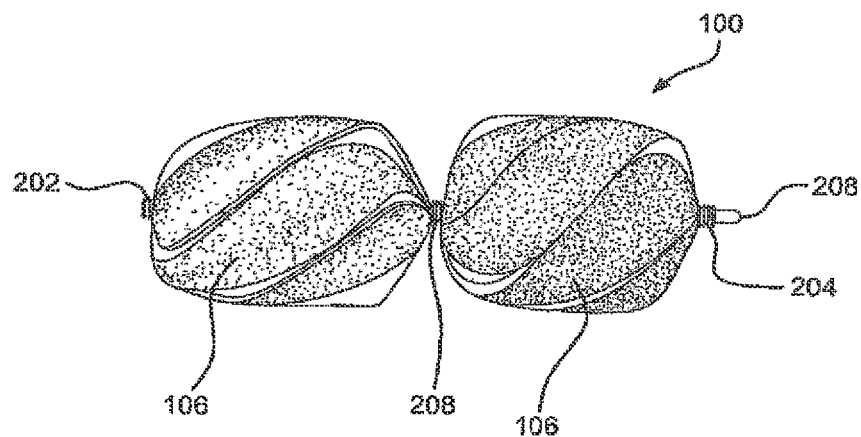
FIG. 5A is a side view of an expanded covered sealing device.

FIG. 5A shows an embodiment of sealing device 100 which is a composite assembly of wire frame 200 and sealing member 106. Sealing member 106 may be attached to wire frame 200 by a bonding agent. Wire frame 200 may be coated with a bonding agent, for example fluorinated ethylene propylene (FEP) or other suitable adhesive. The adhesive may be applied through contact coating, powder coating, dip coating, spray coating, or any other appropriate means. In a preferred embodiment, the FEP adhesive is applied by electrostatic powder coating. Sealing member 106 may be constructed of a variety of materials, such as DACRON®, polyester, polyethylene, polypropylene, fluoropolymers, polyurethane, foamed films, silicone, nylon, silk, thin sheets of super-elastic materials, woven materials, polyethylene terephthalate (PET), collagen, pericardium tissue or any other biocompatible material. In one embodiment, sealing member 106 can be formed of a thin porous ePTFE (expanded polytetrafluoroethylene) substrate. Sealing member 106 is designed to enhance the defect closure characteristics of sealing device 100 by providing defect blockage and a medium for cellular ingrowth.

Also shown in FIG. 5A are proximal, distal and center eyelets (202, 203 and 204), respectively covered with sealing member 106 and wrapped with a film. The eyelets 202, 203 and 204 may be wrapped with a film to encourage adhesion of sealing member 106 to the device. The film used to wrap eyelets 202, 203, and 204 may be any biocompatible thin material but is a material preferably comprised of multiple layers of thin porous ePTFE that may be laminated with one or more layers of non-porous FEP.

Figure 5B:
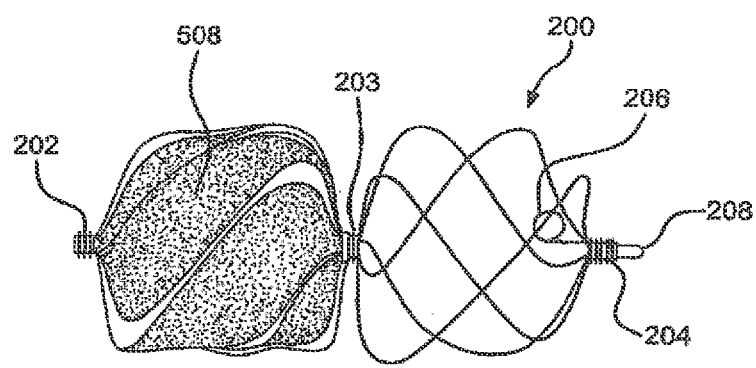
FIG. 5B is a side view of an expanded partially covered sealing device.

FIG. 5B illustrates an embodiment of sealing device 100 that includes a sealing member 508 that partially covers wire frame 200. A partially covered device may have either the distal or proximal bulb covered in part or in entirely with a sealing member 508.

Another embodiment of the device is a self centering device 600. Shown in FIG. 6, self centering device 600 comprises a wire frame 602 similar to that of wire frame 200. Self centering device 600 is a composite assembly of wire frame 602 and sealing member 604. Wire frame 602 may be constructed with the same techniques and a material as wire frame 200 but has no center eyelet. Wire frame 602 comprises distal bumper 606, covered distal eyelet 608, covered proximal eyelet 610, and locking loop 612. The pre-set elastic wire configuration of wire frame 602 allows the frame to twist upon deployment and create a centering region 614 of the device 600 during deployment. During deployment, region 614 may center itself in the defect forming a disk comprised of petals on either side of region 614 and the defect.

Figure 7:
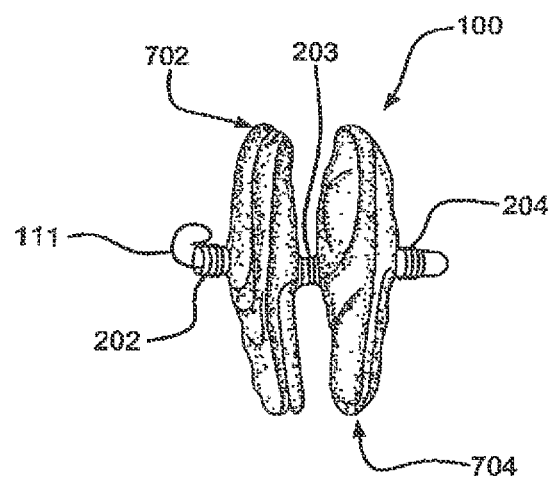
FIG. 7 is a side view of a deployed sealing device.

FIG. 7 shows a sealing device 100 fully deployed. During deployment, the constraint of the third tube 104 is removed from device 100 and the device returns to its pre-set shape. During deployment and locking, lock loop 111 is released from the constraint of first tube 102 and returns to its pre-set shape, curling from the proximal eyelet 202. In this manner, the device is locked in a deployed state. FIG. 7 also illustrates the position of the proximal and distal disks, elements 702 and 704, in relation to the proximal, center, and distal eyelets 202, 203, and 204, respectively.

Figure 19:
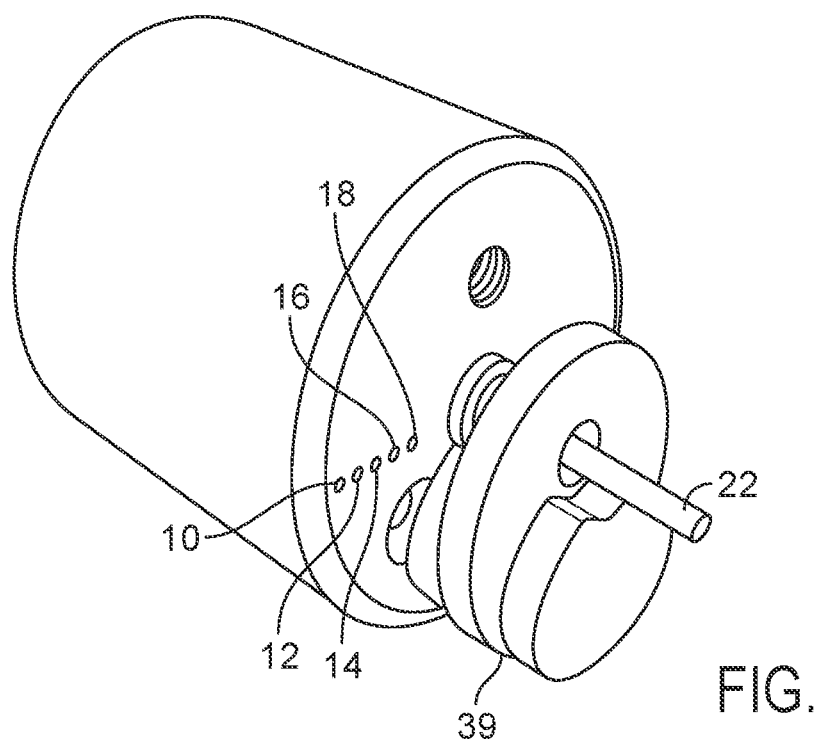
FIG. 19 is a perspective view of a base jig with a self centering petal jig attached.
Figure 20A:
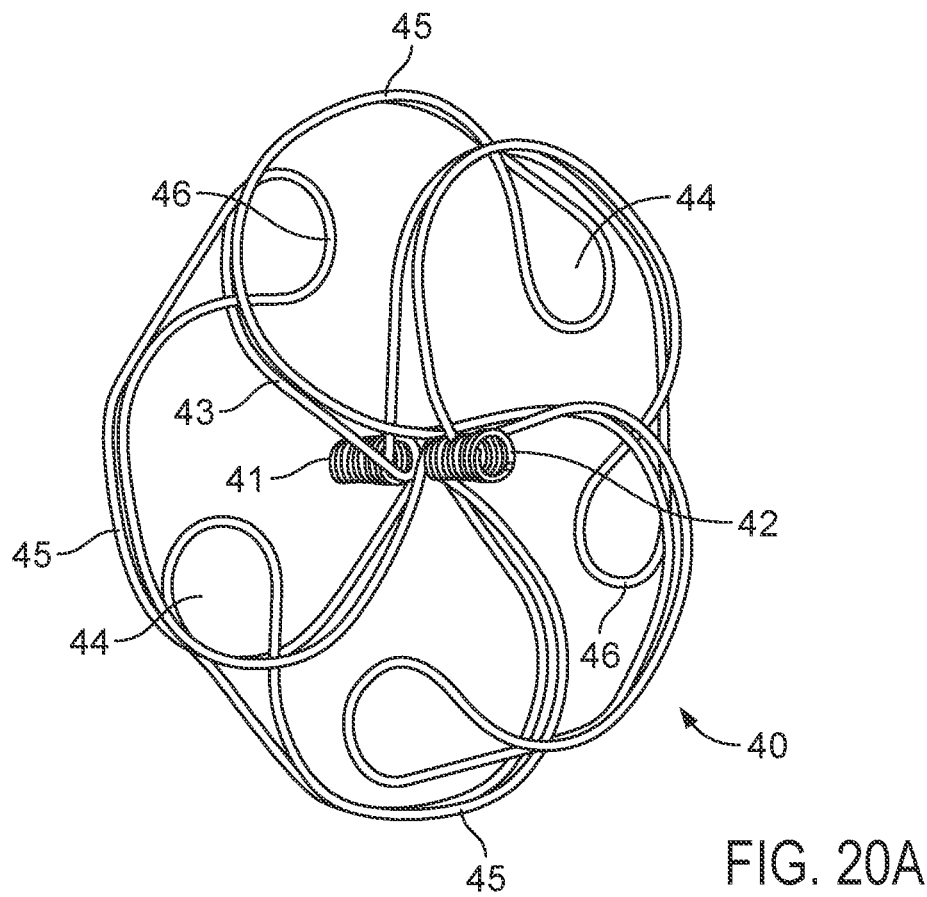
FIG. 20A is a perspective view of a wire frame of a sealing device in a deployed configuration.
Figure 20B:
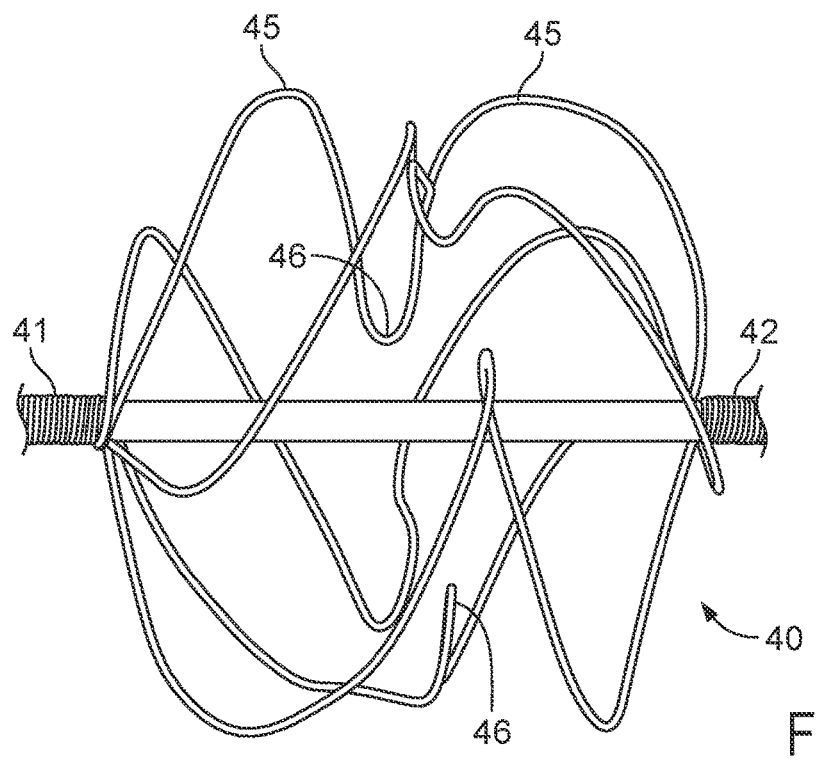
FIG. 20B is a side view of a wire frame of a sealing device shown elongated along a mandrel.

FIG. 19 shows a base jig and other manufacturing aids used to manufacture an embodiment shown in FIGS. 20A and 20B and described in Example 4. As shown in FIGS. 20A and 20B, sealing device 40 is formed of wires 43. Wire frame 40 may be of any size appropriate for an application but is may be sized with outer peripheral edge diameters of 15, 20, 25, or 30 mm. The wire frame is formed of continuous wires. Any number of wires may be used to construct the wire frame 40. FIGS. 20A and 20B show a device formed from 5 continuous wires. FIG. 20A shows a device in a deployed configuration while 20B shows a device in an extended configuration. The wire frame 40 may be constructed of wires that have elastic properties that allow for wire frame 40 to be collapsed for catheter based delivery or thoracoscopic delivery, and self-expand to a "memory" induced configuration once positioned in a defect. The elastic wire may be a spring wire, or a shape memory NiTi (nitinol) alloy wire or a super-elastic NiTi alloy wire. The elastic wire may also be of a drawn-filled type of NiTi containing a different metal at the core. Wire frame 40 may be constructed of a drawn-filled type of NiTi wire containing a radiopaque metal at the center. Upon deployment, the wire structure resumes its deployed shape without permanent deformation.

Wire frame 40 and other wire frames shown are formed from elastic wire materials that have outer diameters between 0.12 and 0.4 mm. When formed, wire frame 40 comprises a first eyelet 41, a second eyelet 42, a plurality of wires 43, a closed teardrop shape with an internal area 44 and inner peripheral edge 46 and an outer peripheral edge 45. In an end view of a deployed device, the outer peripheral edge 45 is shown as the outermost edge of the wire frame 40. The inner peripheral edge 46 of wire frame 40 is illustrated by the inner most edge of the internal area 44 of the closed teardrop shape. In the deployed configuration a wire and closed teardrop shape will nest or interleaf itself between the wire form of the next wire of the device. In a deployed configuration, the inner peripheral edge 46 will at least in part center itself within a cardiac defect or other tissue gap.

The wire frame 40 may be covered with a sealing member as previously described.

Figure 21:
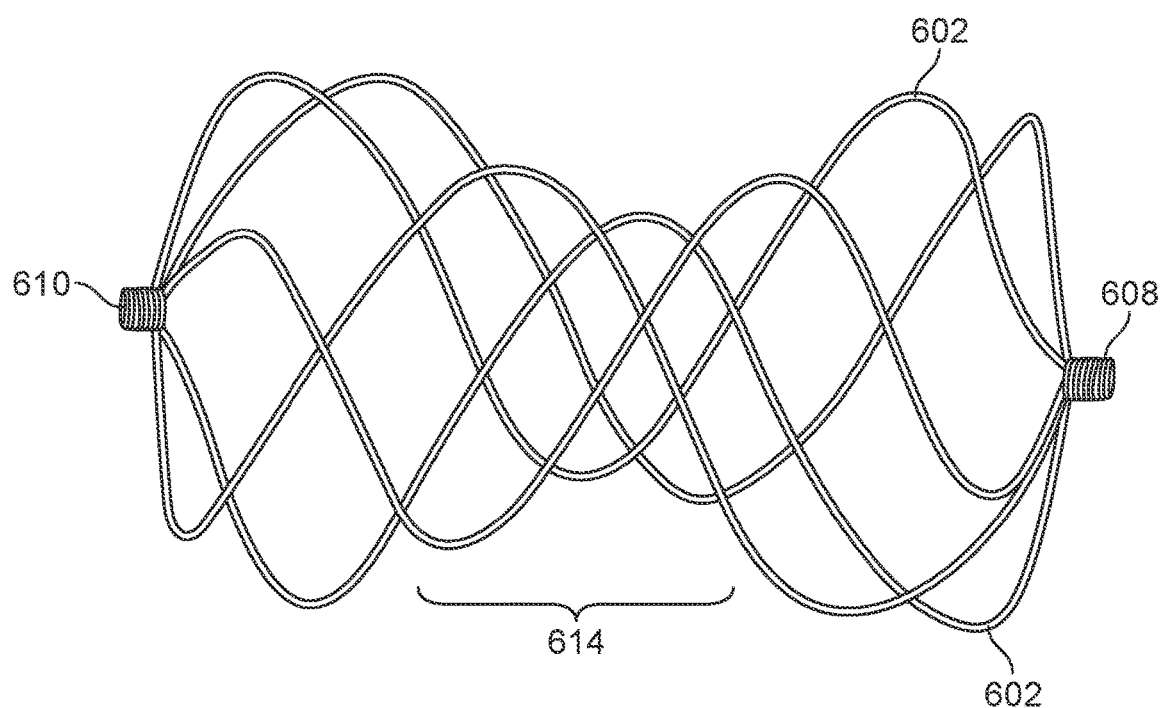
FIG. 21 is a view of a wire frame of a sealing device.

FIG. 21 illustrates an embodiment of the wire frame described in example 5. The embodiment comprises a proximal 610 and distal eyelet 608 with at least five wires 602, and a self centering waist portion 614 similar to that describe previously in relation to FIG. 6. Such an embodiment may be manufactured of similar materials and methods as described previously.

An alternate embodiment of a sealing device may be made by procuring two sealing device frames and seating one inside the other. Then covering the resulting frame as previously described. Such a device is described in example 6. An embodiment such as this may be manufactured with similar materials and methods as described previously and subsequently described. This technique may be used with any of the wire frames described herein.

Figure 22A:
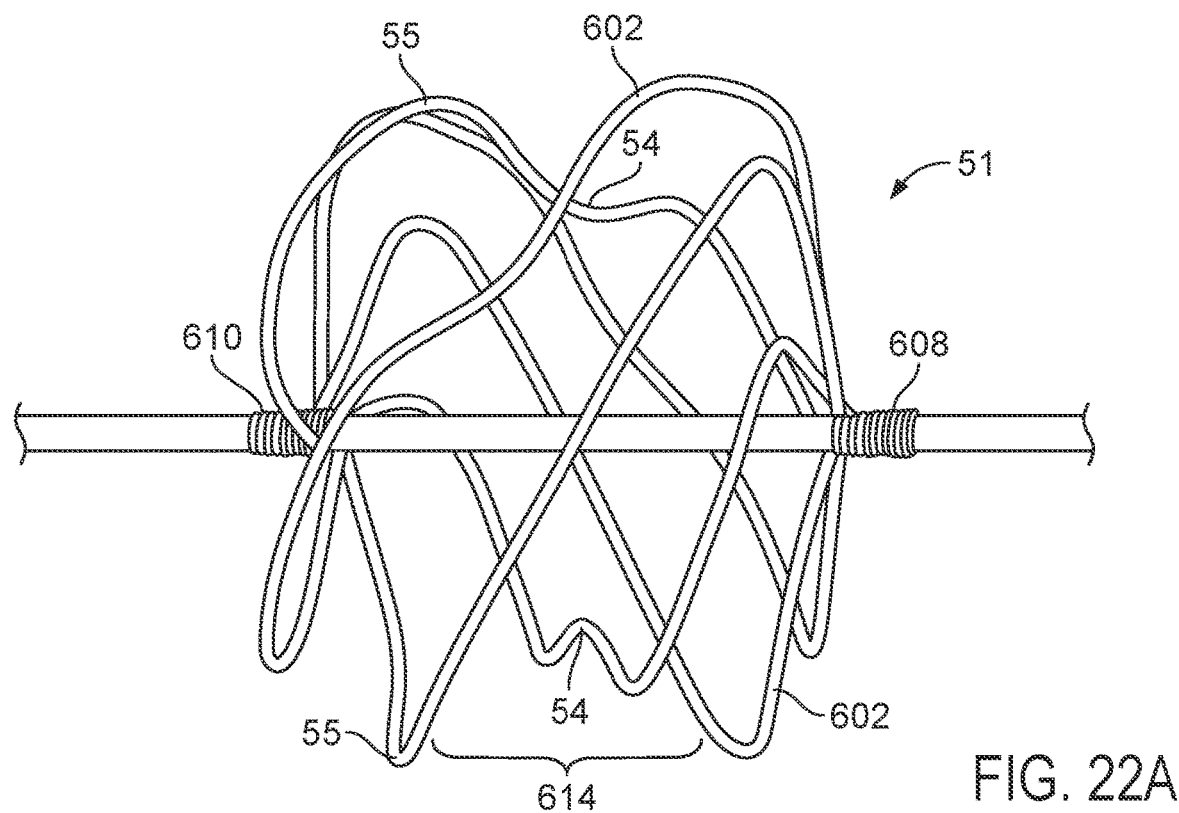
FIG. 22A is a side view of a wire frame of a sealing device shown elongated along a mandrel.

An embodiment is illustrated in FIG. 22A and described in example 7. FIG. 22A illustrates a wire frame 51 of a sealing device. The embodiment of FIG. 22A comprises a proximal 608 and distal eyelet 610, a plurality of wires 602, wires forming a wire frame 51, a self centering waist portion 614, an reniform shape with an open internal area (not shown) with an inner peripheral edge 54 and an outer peripheral edge 55. The self centering waist portion 614 of this embodiment forms a reniform with an open internal area when in the deployed configuration. In an end view of a deployed device, the outer peripheral edge 55 is shown as the outermost edge of the wire frame 51. The inner peripheral edge 54 of wire frame 51 is illustrated by the inner most edge of the open internal area of the reniform shape. In a deployed configuration, the inner peripheral edge 54 will at least in part center itself within a cardiac defect or other tissue gap.

The wire frame 51, as illustrated in FIG. 22A, has a relatively short extended length prior to deployment. A delivery configuration length to deployed radius ratio is about 2.5. Such a device may be formed of similar materials as described previously and may be covered with a sealing member also described previously.

Figure 18B:
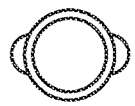
FIGS. 18A, 18B and 18C are schematics of a manufacturing mandrel and an embodiment of a lock loop.
Figure 18A:
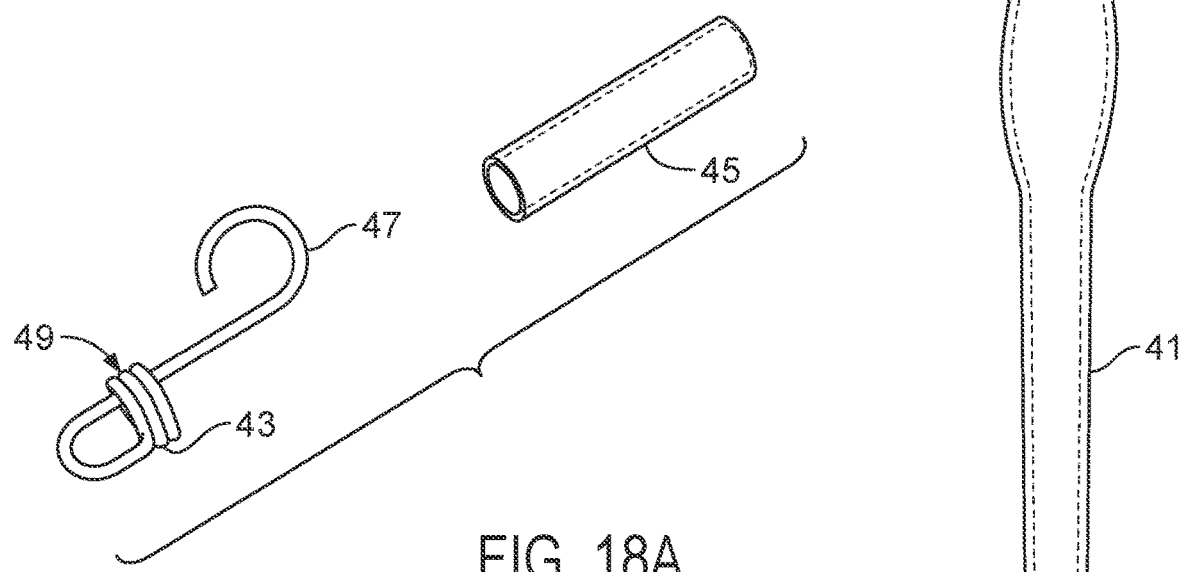

A lock loop 43 (illustrated in FIG. 18A) may be manufactured separately from the wire frame of the sealing device. The lock loop 43 may be formed of any material suitable for forming a sealing device wire frame. The lock loop 43 may be made of a different material or have a different wire diameter than that of the sealing device wire frame. Lock loop component 43 is manufactured with an eyelet 49 similar to the eyelets of the sealing devices described herein. Lock loop 43 may be attached to any sealing device wire frame prior to or post sealing member attachment. Any suitable method of attaching the separate lock loop component to the sealing device may be used. A method of manufacture of a lock loop component is described further in example 9.

Figure 23A:
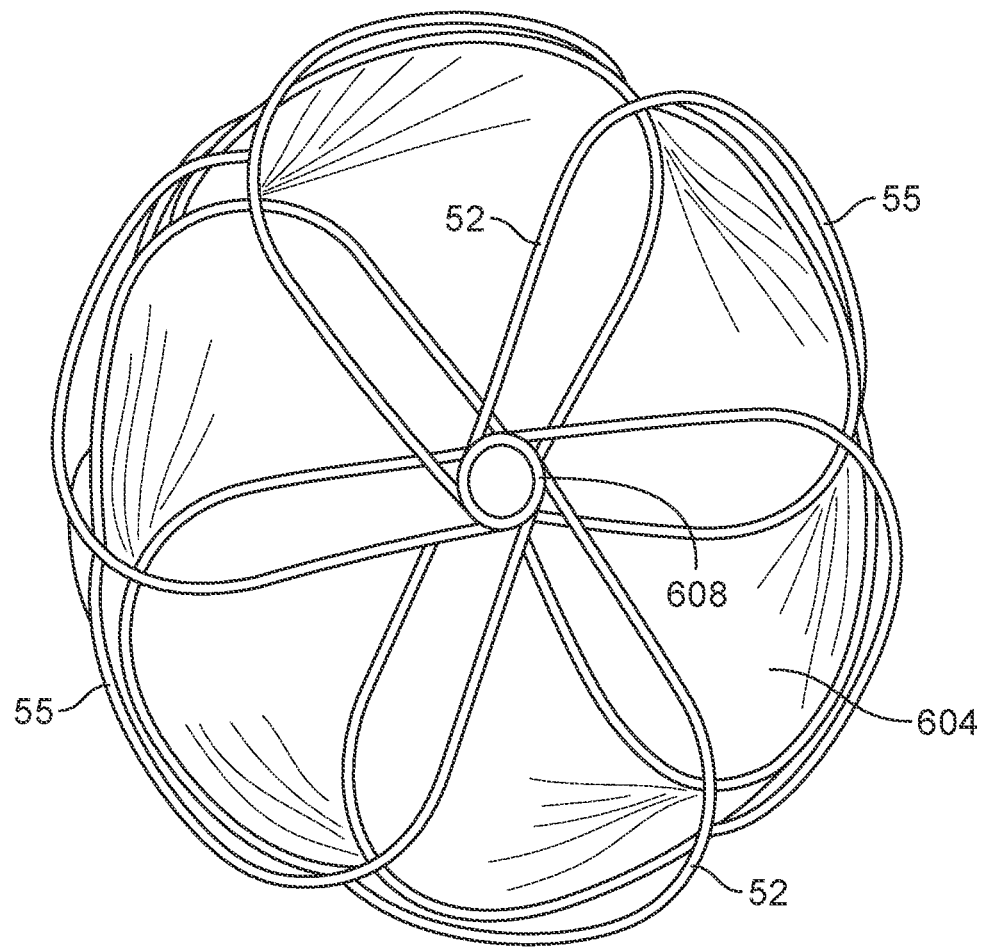
FIG. 23A is an end on view of a sealing device.

FIGS. 23A and B illustrates an embodiment comprising a proximal 608 and distal eyelet 610, a plurality of wires 52, wires forming a wire frame 61, a self centering waist portion 614, an reniform shape with an open internal area (not shown) with an inner peripheral edge 54 and an outer peripheral edge 55 and a sealing member 604. The self centering waist portion 614 of this embodiment forms a reniform with an open internal area when in the deployed configuration. In an end view of a deployed device, the outer peripheral edge 55 is shown as the outermost edge of the wire frame 61. The inner peripheral edge 54 of wire frame 61 is illustrated by the inner most edge of the open internal area of the reniform shape. In a deployed configuration, the inner peripheral edge 54 will at least in part center itself within a cardiac defect or other tissue gap. This embodiment may be constructed with two frames previously described. This embodiment may be constructed of two frames wound in opposite directions or with two frames wound in the same direction. This and the other described wire frames may be constructed with the eyelets configured either as shown or with the eyelets turning toward the center area of the frame along the inner diameter of the device. Materials suitable for use as a sealing member 604 have been discussed previously. Sealing member may be attached to the frame in this and other described embodiments as discussed previously. Sealing member in this and other embodiments may be attached to the interior or inner surface of the wire frame and alternately to the exterior of the frame. The sealing member may be attached at only portions of the wire frame leaving certain portions of the wire frame more degrees of freedom of movement. Sealing member might also be attached to cover one side, portions or the entire wire frame.

Figure 25A:
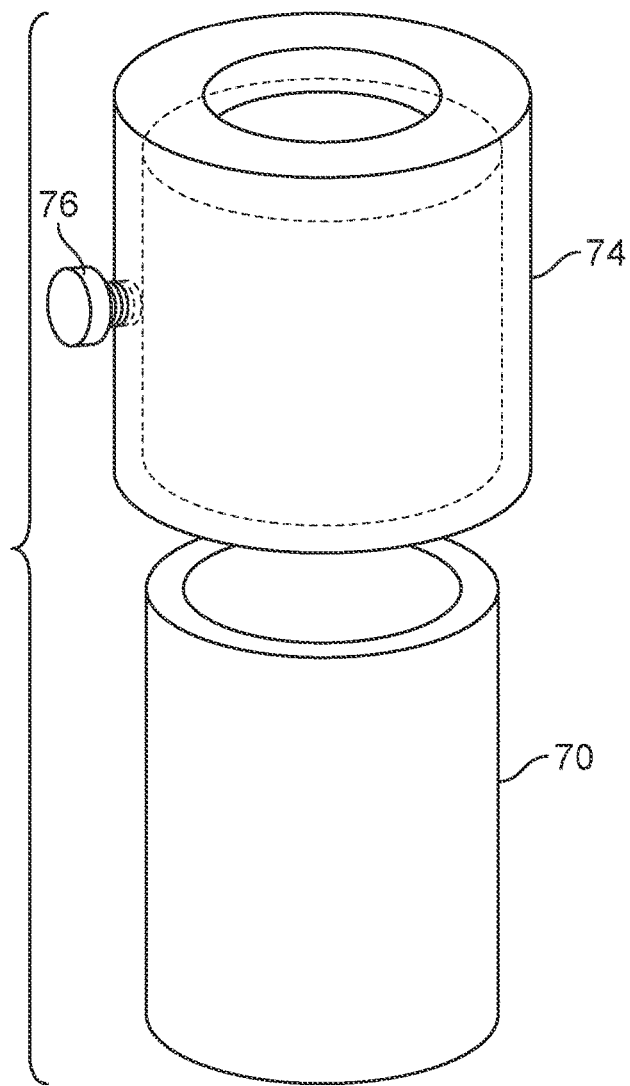
FIGS. 25A and 25B show elements of a wire-frame-forming device and a wire frame of a sealing device.
Figure 25B:
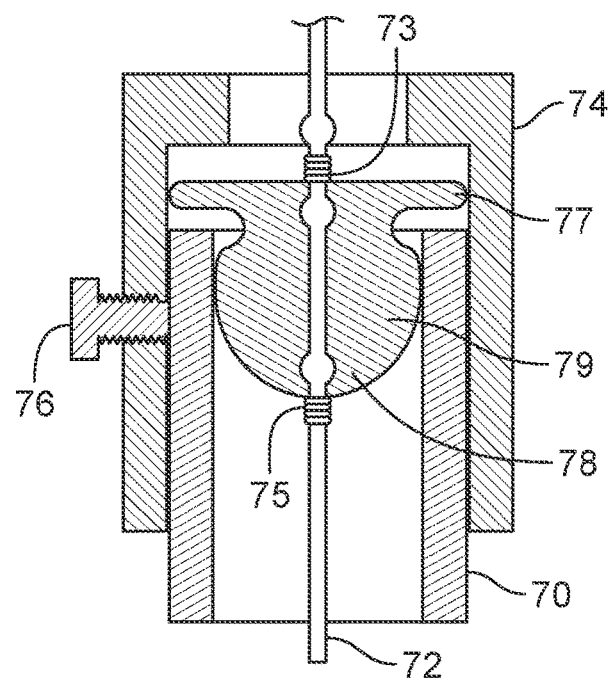

Another embodiment is shown in FIG. 25B. This embodiment may be constructed with similar materials as those described previously. The embodiment comprises a wire frame 78, first and second eyelets (73 and 75, respectively), a sealing disc 77, a plug region 79 and optionally a sealing member 604 (not shown). The embodiment may be constructed of any of the previously described wire frames. The sealing disc portion 77 of the embodiment is adapted to cover a wide range of opening sizes while the plug region 79 is adapted to conform to the anatomy into which it is inserted over its entire length. Sealing disc portion 77 has minimal deformation under radial pressure changes or radial pressure exerted upon the plug region 79. Sealing disc 77 and plug region 79 have substantial directional independence due to the flexibility of waist portion 614: that is, the longitudinal axis of the first eyelet 73 may be at significant offset with respect to the longitudinal axis of the second eyelet 75.

Figure 33:
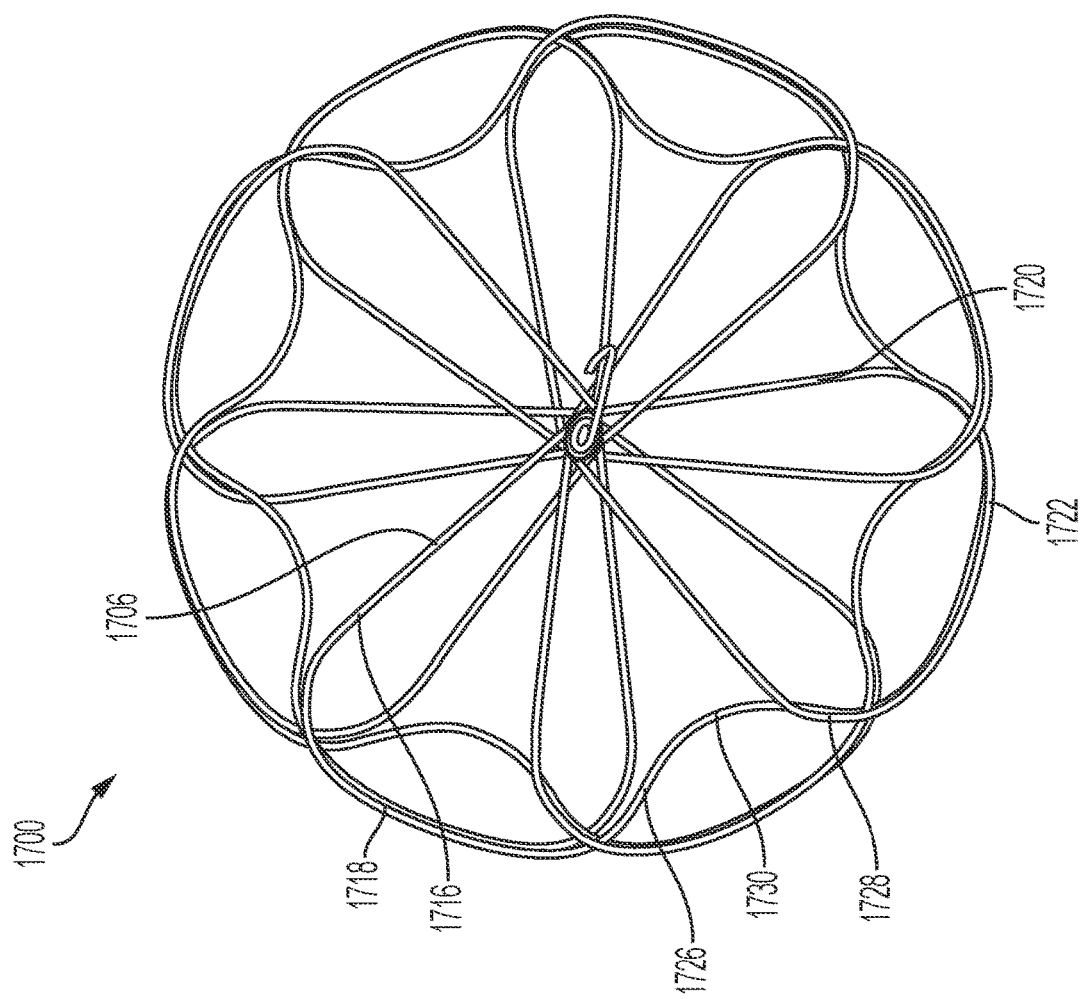
FIG. 33 is an end view of an example frame of an example sealing device.

FIG. 33 is an end view of an example frame 1700 of an example sealing device 1702. FIGS. 36A and 36B are end views of device 1702, where the device 1702 includes the frame 1700 and a sealing member 1704 attached to the frame 1700. FIG. 36A depicts a distal occluding member 1714 of the device, while FIG. 36B depicts a proximal occluding member 1712 of the device, where the distal and proximal occluding members have a generally disc shape (in a deployed configuration).

Device 1702 may be used to seal a defect or tissue opening in a body of a patient, and in particular may be used to seal a defect or structure in a heart, such as a septal defect, or to seal other defects or tissue openings discussed herein. In general, the devices discussed herein may aid in substantially sealing such defects or structures. Device 1702 may be delivered to, and deployed at, a defect or tissue opening using the delivery apparatuses or systems described herein, for example. So that the wires 1706 of the frame 1702 may be more clearly shown, sealing member 1704 is not shown in FIG. 33.

As with other devices described herein, device 1702, and in particular frame 1700, includes a delivery configuration and a deployed configuration, where the frame 1700 may be elongated, extended, or collapsed for passage through a delivery apparatus in the delivery configuration. FIG. 33, and the aforementioned FIGS. 36A and 36B, each depict the frame 1700 or device 1702 in the deployed configuration.

Figure 34:
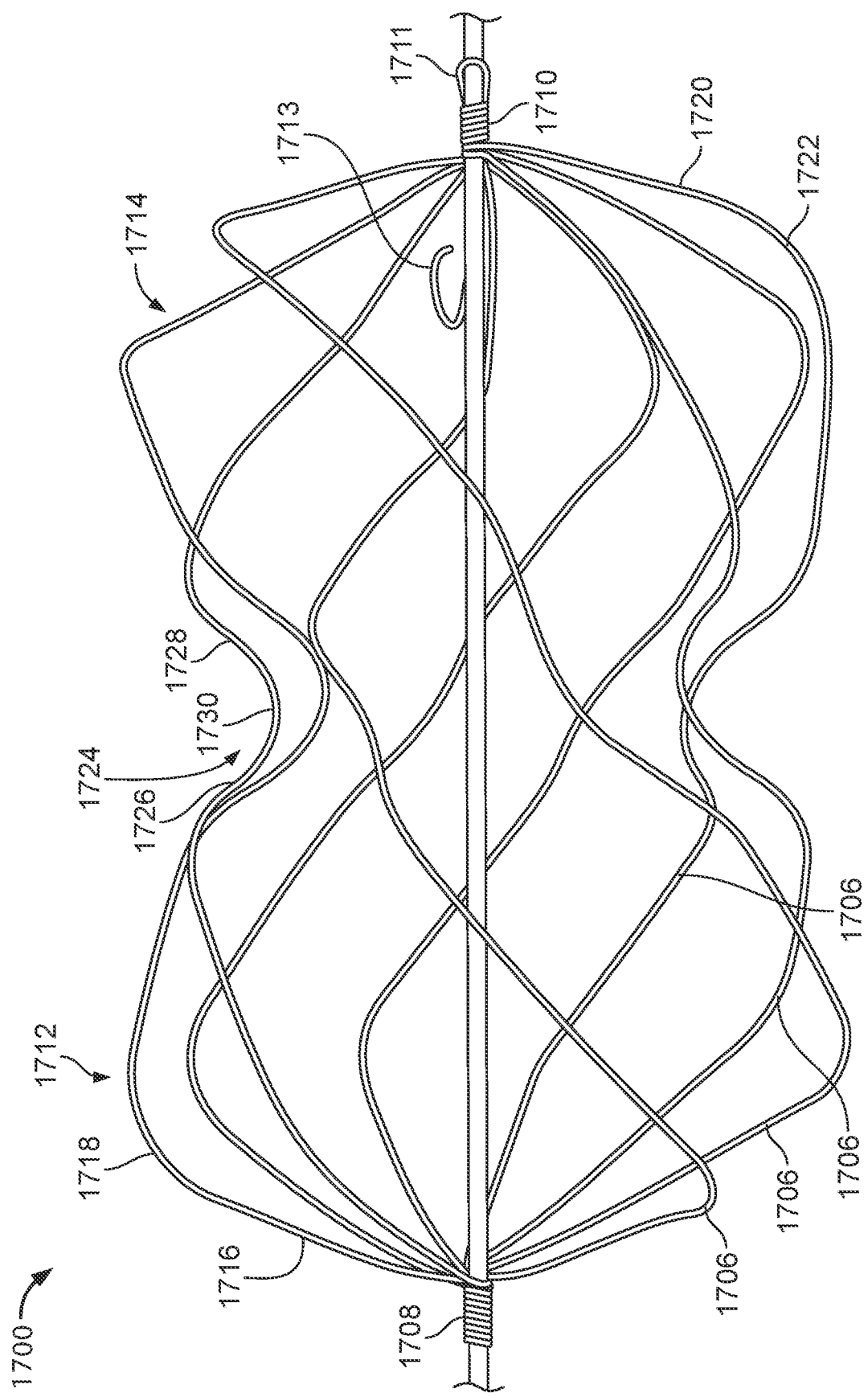
FIG. 34 is a side view of the example frame of FIG. 33, where the frame is shown in a partially elongated state disposed on a mandrel.

FIG. 34 is a side view of the example frame 1700 of FIG. 33, where the frame 1700 is shown in a partially elongated state disposed on a mandrel in FIG. 34. The embodiment of frame 1700 depicted in FIGS. 33 and 34 includes eight wires 1706, four of which are labeled in FIG. 34. Some embodiments of the frame 1700 include six wires, and embodiments that include any desired number of wires (e.g., four, five, seven, nine, ten, eleven, twelve, or more) are envisioned. The wires 1706 of the frame 1700 each extend generally helically from a proximal end of the frame to a distal end of the frame. In general, the wires 1706 may be constructed of any of the materials described herein as pertaining to other wire and frame example embodiments.

Referring again to FIG. 34, the wires 1706 of the frame 1700 form various features of the frame 1700. For example, the frame 1700 includes a first eyelet 1708 near the proximal end of the frame, and a second eyelet 1710 near the distal end of the frame. The first eyelet 1708 can be formed from first end portions of the wires 1706, and the second eyelet 1710 can be formed from second end portions of the wires 1706, in some embodiments. In some examples, one or more of the second end portions of the wires may also form a lock loop, as by extending from the eyelet and forming the lock loop. Eyelets 1708 and 1710 are examples of wire aggregation elements. Other examples of wire aggregation elements can include hub-like elements that receive and terminate ends of each of the wires 1706. In various implementations, frame 1700 includes two wire aggregation elements, generally disposed at or near the proximal and distal ends of the frame, respectively.

The frame 1700 includes a first occluding member 1712 generally adjacent the first eyelet 1708, and a second occluding member 1714 generally adjacent the second eyelet 1710. In some embodiments, the first and second occluding members 1712 and 1714 are discs in the deployed configuration, where the discs are generally formed by portions of the wires 1706. For each wire 1706 of the frame 1700, the first occluding member 1712 includes a first generally linear segment 1716, which may be referred to as a spoke (e.g., a spoke of the first occluding member 1712), and a first generally curved segment 1718, which may be referred to as a rim and a spoke-to-rim transition region, where the first generally linear segment 1716 and the first generally curved segment 1718 together define a petal of the first occluding member 1712. Similarly, for each wire 1706 of the frame 1700, the second occluding member 1714 includes a second generally linear segment 1720, which may also be referred to as a spoke (e.g., a spoke of the second occluding member 1714), and a second generally curved segment 1722, which may be referred to as a rim and a spoke-to-rim transition region, where the second generally linear segment 1720 and the second generally curved segment 1722 together define a petal of the second occluding member 1714.

The frame 1700 also includes a defect-occupying portion 1724 disposed between the first occluding member 1712 and the second occluding member 1714. For each wire 1706 of the frame 1700, the wire 1706 includes, in the defect-occupying portion 1724, a third generally linear segment 1726, a fourth generally linear segment 1728, and a third generally curved segment 1730 disposed between the third generally linear segment 1726 and the fourth generally linear segment 1728. In general, the curved segment 1730 provides an inflection region for engaging the defect, as will be discussed in more detail below. In some implementations, the curved segment 1730 may be substantially in full contact with the defect or structure when deployed. In some implementations, only a portion of the curved segment 1730 may be in contact with the defect or structure when deployed. In some embodiments, the curved segment of the inflection region of the defect-occupying portion can have a radius of about 0.094" to about 0.305". For example, the curved segment of the inflection region of the defect-occupying portion can have a radius of about 0.094" for a device designed to seal defects of size 8-15 mm; can have a radius of about 0.197" for a device designed to seal defects of size 13-20 mm; can have a radius of about 0.305" for a device designed to seal defects of size 18-25 mm; can have a radius of about 0.300" for a device designed to seal defects of size 23-30 mm; and can have a radius of about 0.302" for a device designed to seal defects of size 28-35 mm.

Defect sizes can be determined in a number of ways, as is known to those skilled in the art. One way of determining defect size is to use a sizing balloon, where a balloon catheter is placed across a defect, the balloon is inflated, and an indentation into the balloon is measured to determine a diameter of the defect. See "Sizing of Atrial Septal Defects in Adults," by Hrodmar Helgason et al., Cardiology 2005; 104:1-5, the entire contents of which is hereby incorporated by reference in its entirety for all purposes. Echocardiography can be used to measure septal length, and a septal defect can be measured using fluoroscopy or echocardiography. For example, a contrast-filled, compliant balloon may be placed across the defect and inflated until shunting through the defect has stopped, and the defect size can then be measured using either echocardiography or calibrated fluoroscopy, as will be known to one of skill in the art.

FIG. 33 shows the various wire regions 1716, 1718, 1726, 1730, 1728, 1722, and 1720 labeled for a single wire 1706, while FIG. 34 shows some of the wire portions labeled on one wire and others of the wire portions labeled on a different wire.

FIG. 34 also shows a lock loop 1713 and a bumper 1711. The lock loop 1713 includes a straight portion of the lock loop and a "pigtail" of the lock loop. The lock loop 1713 in not locked in FIG. 34.

Figure 35:
FIG. 35 is a side view of an example sealing device in a partially elongated state.

FIG. 35 is a side view of the device 1702 in a partially elongated state on a mandrel, where the device 1702 includes the frame 1700 and sealing member 1704. Sealing member 1704 may be the same or similar to sealing members discussed elsewhere herein. For example, sealing member 1704 may be an ePTFE layer of material, and may be bonded to the frame by an adhesive, such as FEP. In some examples, the one or more portions of the sealing member 1704 may be coated with a hydrophilic material to facilitate imaging of the device and surrounding tissue during implantation.

Implementations of frame 1700, and generally of device 1702, can be used to seal a wide variety of defect shapes and sizes. In general, defects of relatively widely varying defect sizes may be effectively sealed using device 1702. For example, some implementations of device 1702 may effectively seal defects having a size range, from largest size to smallest size, where the size range from largest size to smallest size is up to about 7 mm. For example, depending on device 1702 size, a single device 1702 may be used to seal defects of size 8-15 mm; a single device 1702 may be used to seal defects of size 13-20 mm; a single device 1702 may be used to seal defects of size 18-25 mm; a single device 1702 may be used to seal defects of size 23-30 mm; or a single device 1702 may be used to seal defects of size 28-35 mm.

In some embodiments, the defect occupying portion 1724 is adapted to substantially fill a range of potential defect sizes from a largest defect size to a smallest defect size that is approximately 60% of the largest defect size, and wherein the defect-occupying portion deflects to an outer diameter that is less than about 60% of its nominal outer diameter when a radial pressure of about 0.04 N/mm $2$ is applied to the defect occupying portion. In some embodiments, the device may be configured such that the defect-occupying portion conforms to the shape of the defect, and the occluding members still maintain a generally flat profile (e.g., minimize substantial deviation from the contours of the tissue) on the tissue surface.

The defect-occupying portion 1724 of the device may be very compliant. For example, when the device 1702 is placed in a defect, the defect-occupying portion 1724 of the device may not substantially deform the defect by pushing against the edge of the defect. Yet, the defect-occupying portion 1724 may still substantially fill the defect for a wide variety of defect sizes and defect shapes. For example, the defect-occupying portion 1724 may deflect based on a radial pressure applied to the defect-occupying portion 1724 by an edge of the defect. Moreover, such deflection of the defect-occupying portion 1724 may not induce "mushrooming" or lifting effects on the occluding member discs of the device, so that the occluding member discs may continue to maintain a generally flat profile and conform to the tissue variances of the respective tissue surfaces that the discs appose.

Radial stiffness testing, wherein a radial pressure is applied to the defect-occupying portion 1724 of the device and a deflection of the defect-occupying portion is measured, has demonstrated the compliance of the defect-occupying portion. For example, the defect-occupying portion 1724 of the device deflects to an outer diameter that is less than about 60% of its nominal outer diameter when a radial pressure of about 0.04 N/mm $2$ is applied to the defect-occupying portion. Measurement of the defect-occupying portion deflection includes measuring a nominal outer diameter of the defect-occupying portion when the device is in a deployed configuration and when substantially zero radial pressure is applied to the defect-occupying portion, applying the radial pressure, and measuring the outer diameter again.

The outer diameter of the defect-occupying portion can be measured at an inflection region of the defect-occupying portion, and such a diameter may be referred to as an inflection diameter of the device. For example, for a defect-occupying portion 1724 that includes, for each wire of the device, first and second linear sections and a curved section between the linear sections, the nominal outer diameter can be measured across the defect-occupying portion at the curved sections of opposing wires. The radial pressure may be applied by a flexible loop of a tensile testing machine, where an adjustable load balance of the testing machine can determine the amount of radial pressure applied by the flexible loop. With 0.04 N/mm² of radial pressure applied to the defect-occupying portion 1724, the inflection diameter of the device is reduced to less than about 60% of the nominal inflection diameter, for example, because the defect-occupying portion 1724 is conformable.

In some embodiments, a first device that has a maximal nominal outer diameter of its occluding members of 27 mm, and a maximum nominal diameter of its defect-occupying portion of 17 mm can be used to seal defects of size 8-15 mm. In some embodiments, a second device that has a maximal nominal outer diameter of its occluding members of 32 mm, and a maximum nominal diameter of its defect-occupying portion of 22 mm can be used to seal defects of size 13-20 mm. In some embodiments, a third device that has a maximal nominal outer diameter of its occluding members of 37 mm, and a maximum nominal diameter of its defect-occupying portion of 27 mm can be used to seal defects of size 18-25 mm. In some embodiments, a fourth device that has a maximal nominal outer diameter of its occluding members of 44 mm, and a maximum nominal diameter of its defect-occupying portion of 32 mm can be used to seal defects of size 23-30 mm. In some embodiments, a fifth device that has a maximal nominal outer diameter of its occluding members of 48 mm, and a maximum nominal diameter of its defect-occupying portion of 36 mm can be used to seal defects of size 28-35 mm.

Figure 37B:
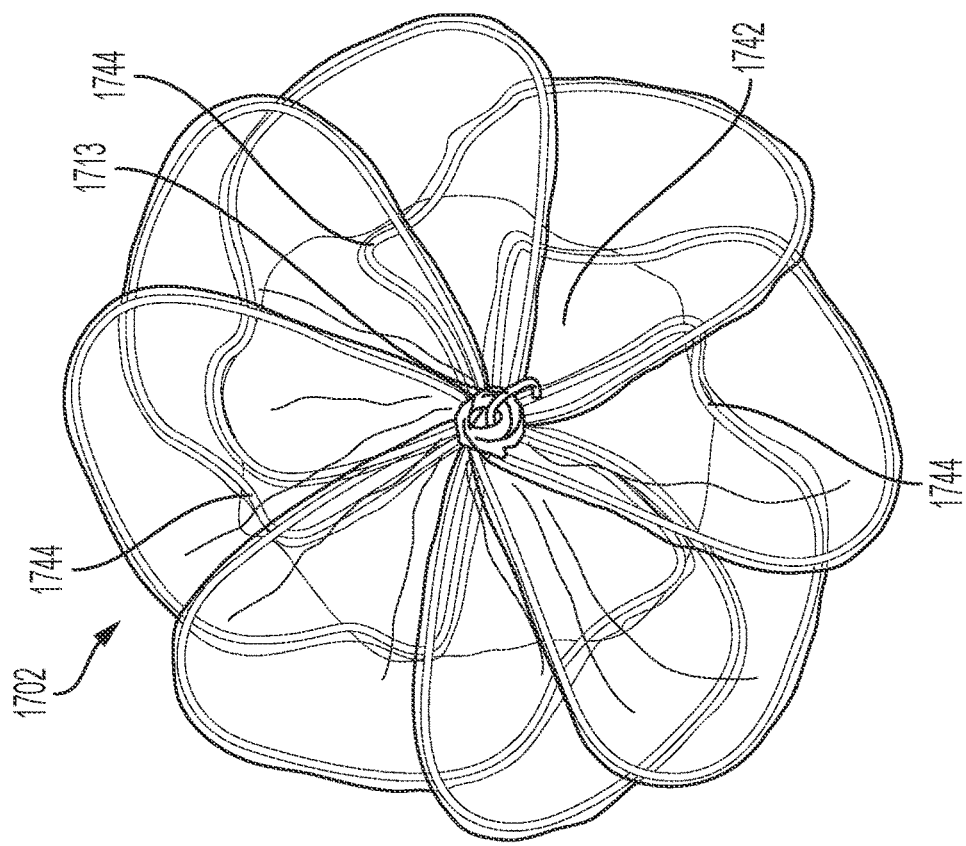
FIGS. 37A and 37B are views of the device of FIG. 35 deployed in example defects that have generally circular shapes.
Figure 37A:
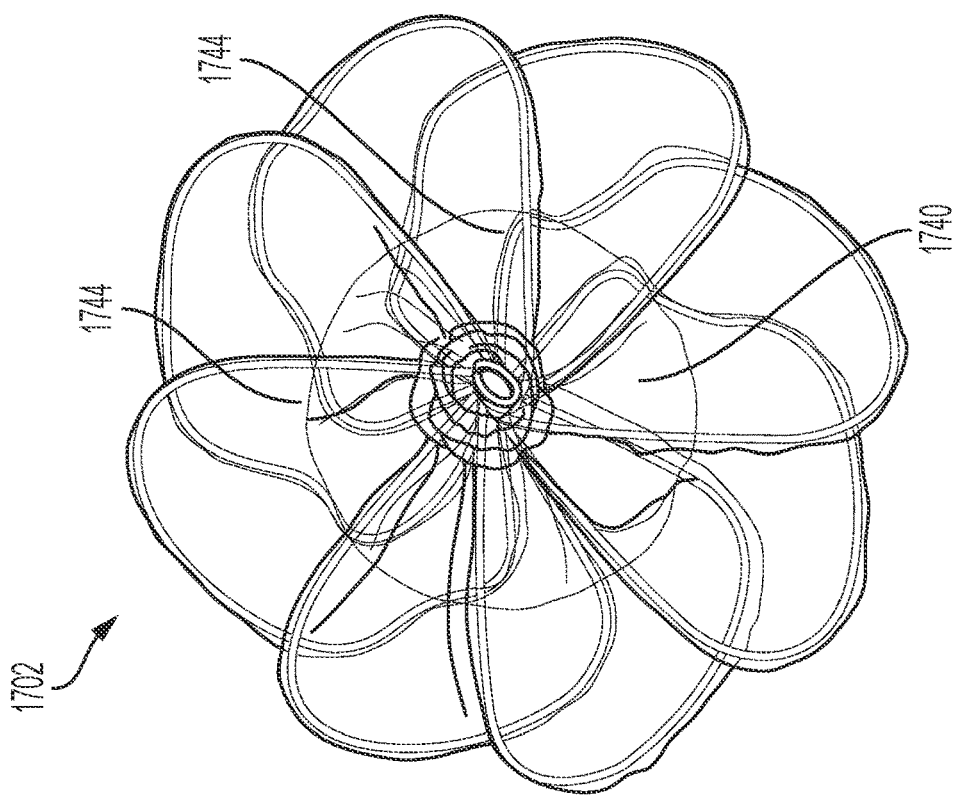

FIGS. 37A and 37B show the device 1702 deployed in example defects 1740 and 1742, respectively. A first defect 1740, having a dark shade in FIG. 37A in contrast to the surrounding lighter shade tissue surface, has a generally circular shape and a relatively smaller defect diameter. For example, the diameter of defect 1742 is 28 mm. A second defect 1742, having a dark shade in FIG. 37B in contrast to the surrounding lighter shade tissue surface, also has a generally circular shape, but has a relatively larger defect diameter. For example, the diameter of defect 1740 is 35 mm. In some examples, device 1702 includes one or more radiopaque markers 1744 in the defect-occupying portion 1724 of the device. In this example, the device 1702 includes four radiopaque markers 1744, one for every other (alternating) wire of the device 1702. The radiopaque markers 1744 may be gold bands, in some implementations. In some examples, the radiopaque markers may be crimped on to the wires 1706 in the inflection region of the defect-occupying portion 1724 for ease of device placement verification. Three markers 1744 are visible in FIG. 37B, and two markers 1744 are visible in FIG. 37A (the non-visible markers are obscured by the example tissue in each figure). As can be seen in FIGS. 37A and 37B, the markers 1744 are resting against the edges of the defects 1740 and 1742, both for the smaller diameter defect 1740 and for the larger diameter defect 1742. This demonstrates the device's efficacy in sealing defects of disparate size, in that the defect occupying region 1724 is adapted to substantially fully occupy the defect 1740 or 1742, without applying undesired outward radial pressure against the wall of the defect. In some embodiments, device 1702 can treat a range of defect sizes without the rims or peripheral edges of the occluding members being substantially raised from the septal tissue. That is, even the rims of the devices may be in contact with tissue surrounding the defect for defects sizes within a treatment range of the device. FIG. 37B shows a lock loop 1713 that is locked or in a lock-loop-deployed configuration.

Figure 38:
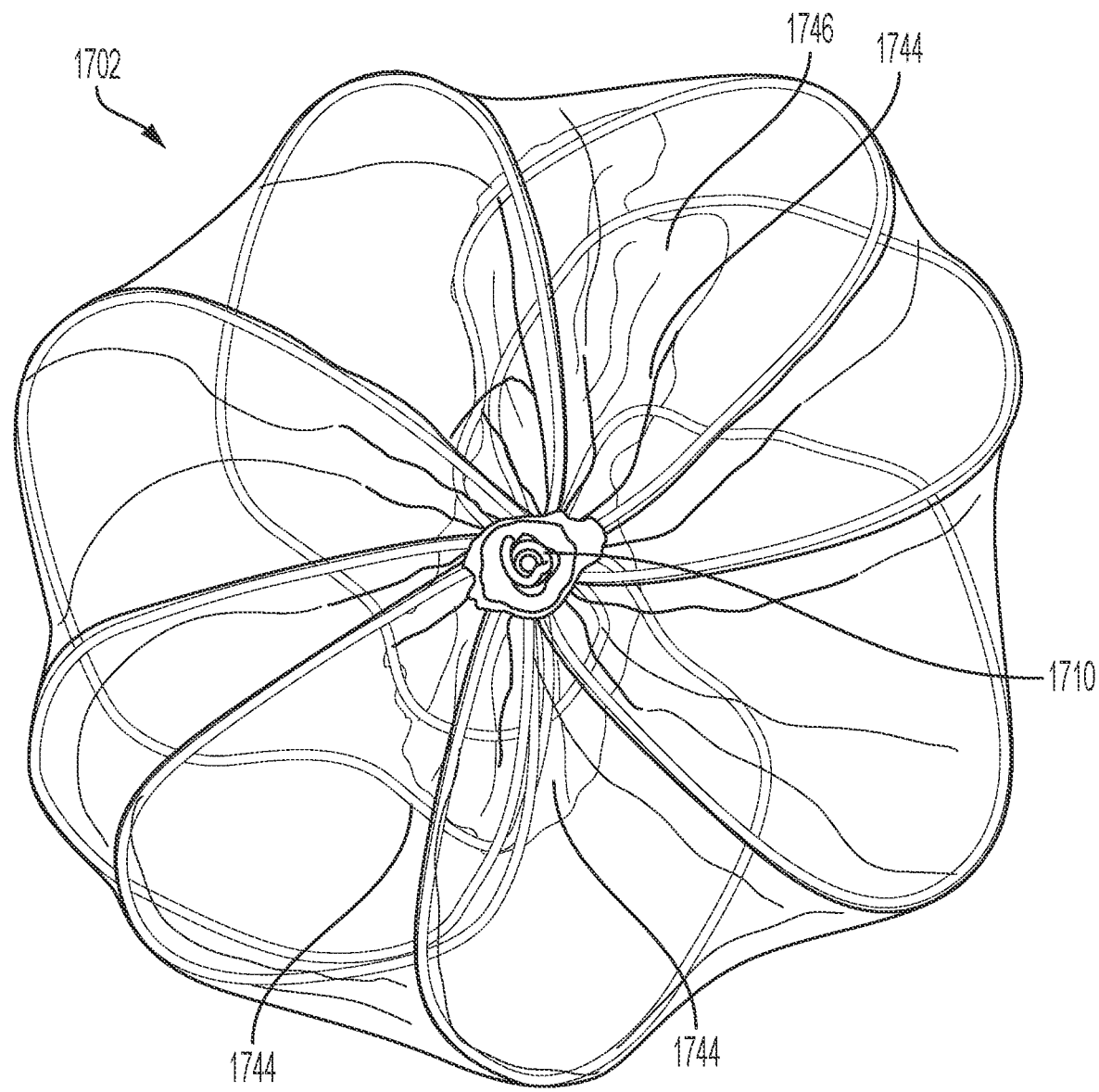
FIG. 38 is a view of the device of FIG. 35 deployed in an example defect that has a non-circular shape.

Additionally, defects having uniform shapes, as well as defects having non-uniform or irregular shapes, may be effectively sealed using device 1702. FIG. 38 shows the device 1702 deployed in an example defect 1746 having a generally elliptical shape, the defect 1746 having a dark shade in FIG. 38 in contrast to the surrounding lighter shade tissue surface. Three markers 1744 are visible in FIG. 38 (the non-visible marker being obscured by the example tissue), and as can be seen the markers 1744 are generally resting against the edge of the defect 1746. This demonstrates the device's efficacy in sealing defects of irregular (e.g., generally non-circular) shape, in that the defect occupying region 1724 is adapted to substantially fully occupy the defect 1746, without applying undue outward radial pressure against the wall of the defect 1746. In general, the device 1702 may be used to seal a defect having a generally round shape, a generally elliptical shape, a generally pear shape, a generally triangular shape, a generally square or rectangular shape, a generally polygon shape, a generally semi-circular shape, or generally amorphous shapes.

FIG. 38 also shows that an occluding member need not be centered at the geometric center of a defect, as the eyelet 1710 is generally in the lower half of the defect 1746 along the long axis of the defect, as shown. For example, the device may be non-self-centering.

Additionally, the occluding members 1712 and 1714 of device 1702 may effectively conform to tissue regions on either side of the defect (e.g., the septal wall on either side of the defect), whether the geometry of such tissue regions is generally flat, or includes a non-flat topography, such as including one or more convex regions, one or more concave regions, or combinations of the foregoing (e.g., ridges or valleys in the tissue surface). Stated another way, the occluding members or discs of the device may effectively conform to one or more curvatures of the septum in the area around the defect. In general, the occluding member's or members' tendency to conform to the geometry of the surrounding surface, in concert with the defect-occupying portion's compliance and minimal outward radial force application, permits the device to adapt to the defect, including by enabling offset of one or both of the occluding members from a center of the defect (e.g., as shown in FIG. 38). For a wide variety of defect sizes and shapes, the defect-occupying portion 1724 of the device 1702 may substantially fully occupy the defect and may conform to the size and shape of the defect without imparting a force that is sufficient to cause buckling, lifting, or mushrooming of the occluding members 1712 and 1714 of the device, so that the occluding members 1712 and 1714 may remain in contact with, and provide apposition force against, the respective tissue surfaces (e.g., septal wall surfaces) on each side of the defect.

Figure 39:
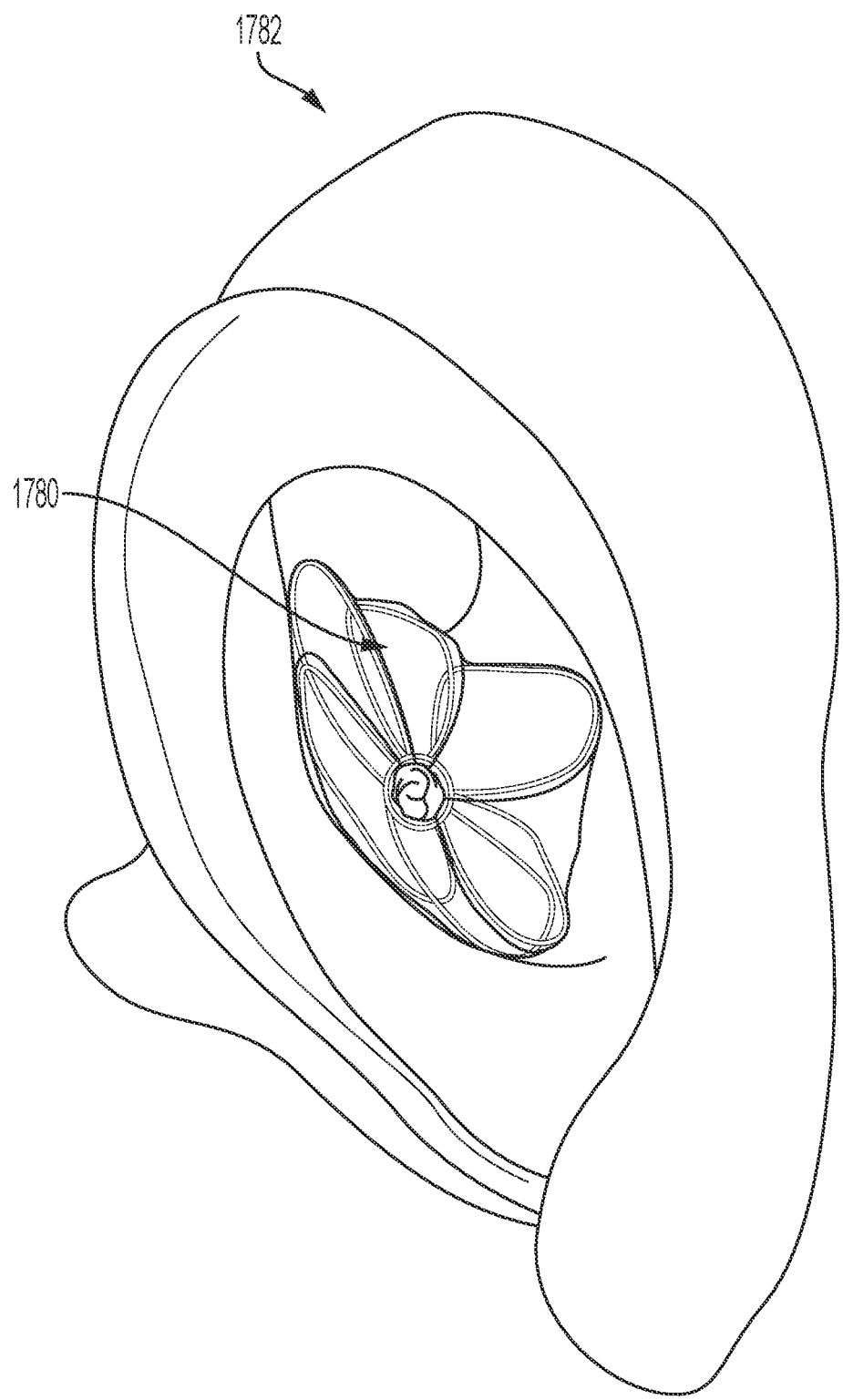
FIG. 39 is a view of an example sealing device deployed in a defect in an example heart model.

FIG. 39 is a three-dimensional view of an example sealing device 1780 deployed in a model 1782 of a portion of a human heart that includes a septum with a tissue surface that includes a curved topography. In this example, the frame of device 1780 includes six wires. The device 1780 is deployed in an atrial septal defect, and the occluding member can be seen conforming to the septum on the right atrium side of the heart, when viewed through the inferior vena cava. As can be seen in FIG. 39, the occluding member of the sealing device 1780 conforms to the concave curvature of the septal tissue surrounding the defect. In general, the occluding members of the device provide an apposition force against the corresponding septal wall and generally assume the topography of the wall surface to substantially seal flat against the wall surface.

Referring again to device 1702, the wires 1706 of frame 1700 are generally arranged such that they can move independently of one another between the eyelets 1708 and 1710. As one wire 1706 or a portion of the wire encounters a geometry of a tissue, for example, the wire or portion of the wire is able to conform to the geometry of the tissue without substantially deflecting or affecting other wires 1706 of the device, in some embodiments. Stated another way, a wire portion or a petal of the first occluding member is adapted to bear a load associated with a first tissue surface without imparting a substantial force to the other wires of the device. Similarly, a wire portion or a petal of the second occluding member is adapted to bear a load associated with a second tissue surface without imparting a substantial force to the other wires of the device. For example, a first petal (e.g., of the first occluding member) that bears a load associated with a first tissue surface may not impart a substantial force to other petals (e.g., other petals of the first occluding member). Similarly, a second petal (e.g., of the second occluding member) that bears a load associated with a second tissue surface may not impart a substantial force to other petals (e.g., other petals of the second occluding member). Also, a given wire 1706 forms a petal of the first occluding member and also forms a petal of the second occluding member, and in general the petal of the first occluding member may move substantially independently from the petal of the second occluding member, and the petal of the second occluding member may move substantially independently from the petal of the first occluding member. The petals may move generally independently from one another, and even for petals formed from the same wire (e.g., where one petal forms a portion of the proximal disc and the other petal forms a portion of the distal disc), the petals may generally move or conform to the tissue substantially independently from one another. In some embodiments, a movement of one wire may not directly translate to a movement of one or more other wires of the device. Stated another way, a given wire is able to bear a load generally without substantially affecting other wires of the device.

After deployment, the final position of the device may be primarily driven by the occluding member 1712 and 1714 interactions with the tissue surfaces around the defect, and only minimally or substantially not driven by the defect-occupying portion's 1724 interface with the interior wall of the defect. The defect-occupying portion 1724 or a portion thereof (e.g., the curved segment or only a portion of the curved segment) may maintain contact with the wall of the defect, but may be adapted to not provide substantial apposition force against the defect, or against an interior wall of the defect. This can minimize or prevent "mushrooming" or bulging of the occluding members 1712 or 1714 or portions thereof, and can minimize or prevent substantial deviation from a substantially flat tissue profile (e.g., minimize or prevent substantial deviation from the contours of the tissue), so that a seal that is less susceptible to a passage or leakage of fluid through the defect may be achieved, in some implementations. In some embodiments, the device may be configured such that the defect-occupying portion conforms to the shape of the defect and the occluding members still maintain a generally flat profile (e.g., minimize substantial deviation from the contours of the tissue) on the tissue surface. By maintaining a generally flat profile against the tissue surface, for example, the occluding members may occupy a smaller volume within the atrium as compared to other sealing devices where mushrooming of the discs can be a problem for some defects. Maintaining a flat profile also may facilitate better incorporation of the device into native tissue via a tissue ingrowth process, for example.

In general, the devices shown in FIGS. 33-39 and described above are able to substantially seal a defect or structure in a heart of a patient, and to substantially occupy the defect or structure, based on a combination and interrelation of device properties that cooperate in a synergistic manner. For example, a structure and orientation of the elongate elements including, e.g., the structure and orientation of the various portions or regions of the elongate elements, work together to provide for a stable placement of the device, while maintaining a profile that approximates the respective tissue surfaces on either side of the defect or structure.

Figure 40:
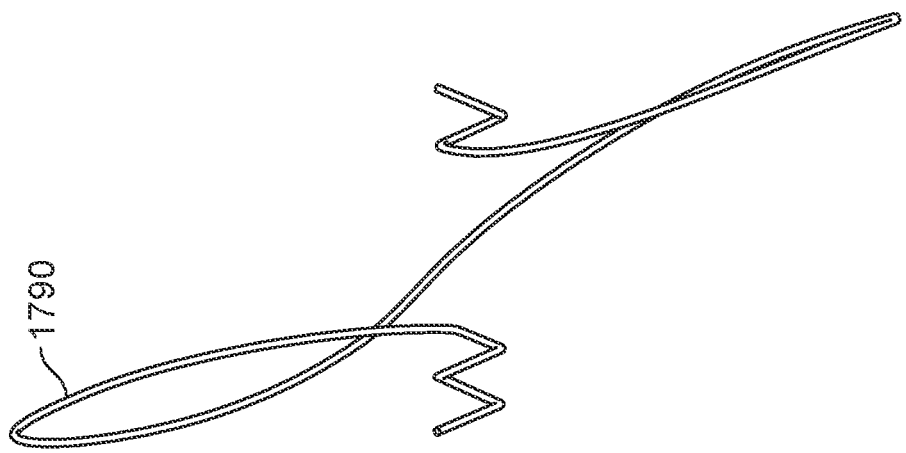
FIG. 40 is a lateral view of a single wire of an example sealing device in a deployed configuration.

FIG. 40 is a lateral view of a single wire 1790 of a six-wire device, such as device 1780 of FIG. 39, in a deployed configuration.

Figure 41B:
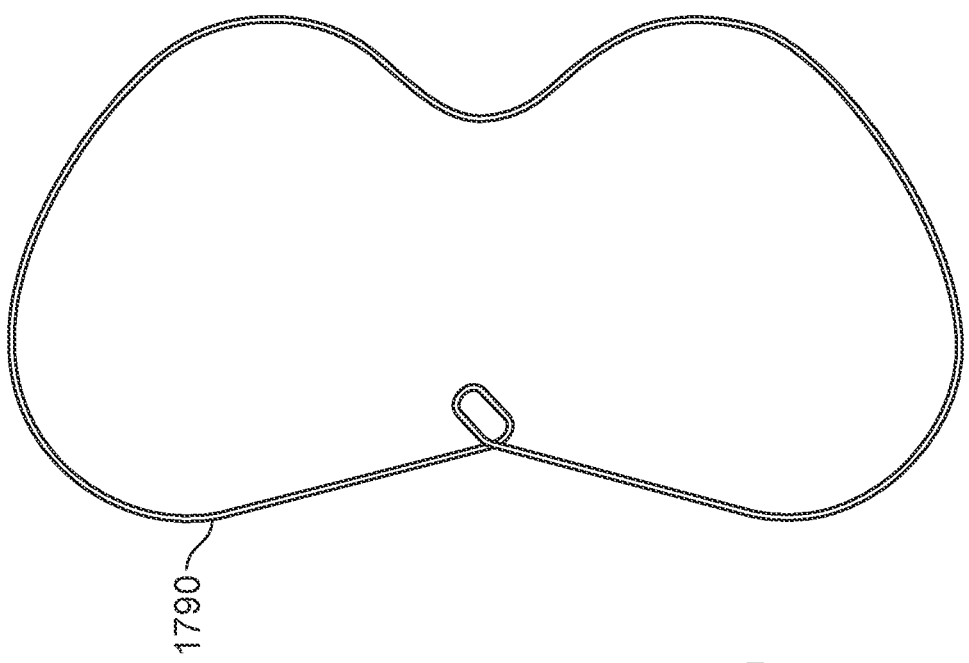
FIG. 41B is an end view of a single wire of the example frame the device of FIG. 39.
Figure 41A:
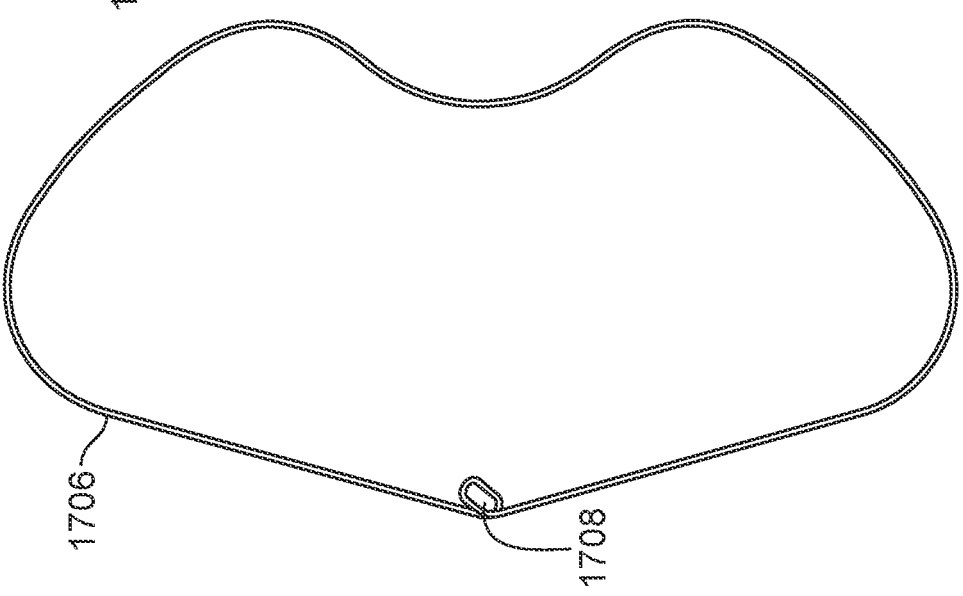
FIG. 41A is an end view of a single wire of the example frame of FIG. 33.

FIG. 41A is an end view of a single wire 1706 of example frame 1700. In this view, the proximal and distal eyelets are aligned longitudinally, so that the distal eyelet is immediately below the labeled proximal eyelet 1708. FIG. 41A shows that an angle defined by the wire's exit from the proximal eyelet 1708 and the wire's entry to the distal eyelet is about 150 degrees, or in some embodiments in a range from about 150 degrees to about 152 degrees. More particularly, for a device sized to occlude a defect with a size of 23-30 mm, the angle defined by the aforementioned wire exit and entry points to the eyelets is about 152 degrees; and for a device sized to occlude a defect with a size of 28-35 mm, the angle defined by the aforementioned wire exit and entry points to the eyelets is about 150 degrees. In general, frame 1700 includes eight wires 1706. In some embodiments, each of the device's wires, when viewed individually, may define one of the aforementioned angles between the respective wire's exit and entry points. For each of the occluding members of the device, adjacent petals formed by the individual wires and corresponding to a particular occluding member will overlap one another.

FIG. 41B is an end view of a single wire 1790 of the frame of example device 1780. FIG. 41B shows that an angle defined by the wire's exit from the proximal eyelet and the wire's entry to the distal eyelet is about 210 degrees, or in some embodiments in a range from about 210 degrees to about 214 degrees. More particularly, for a device sized to occlude a defect with a size of 8-15 mm, the angle defined by the aforementioned wire exit and entry points to the eyelets is about 212 degrees; for a device sized to occlude a defect with a size of 13-mm, the angle defined by the aforementioned wire exit and entry points to the eyelets is about 214 degrees; and for a device sized to occlude a defect with a size of 18-25 mm, the angle defined by the aforementioned wire exit and entry points to the eyelets is about 210 degrees. In general, the frame for device 1780 includes six wires 1790. In some embodiments, each of the device's wires, when viewed individually, may define one of the aforementioned angles between the respective wire's exit and entry points. For each of the occluding members of the device, adjacent petals formed by the individual wires and corresponding to a particular occluding member will overlap one another.

Figure 42:
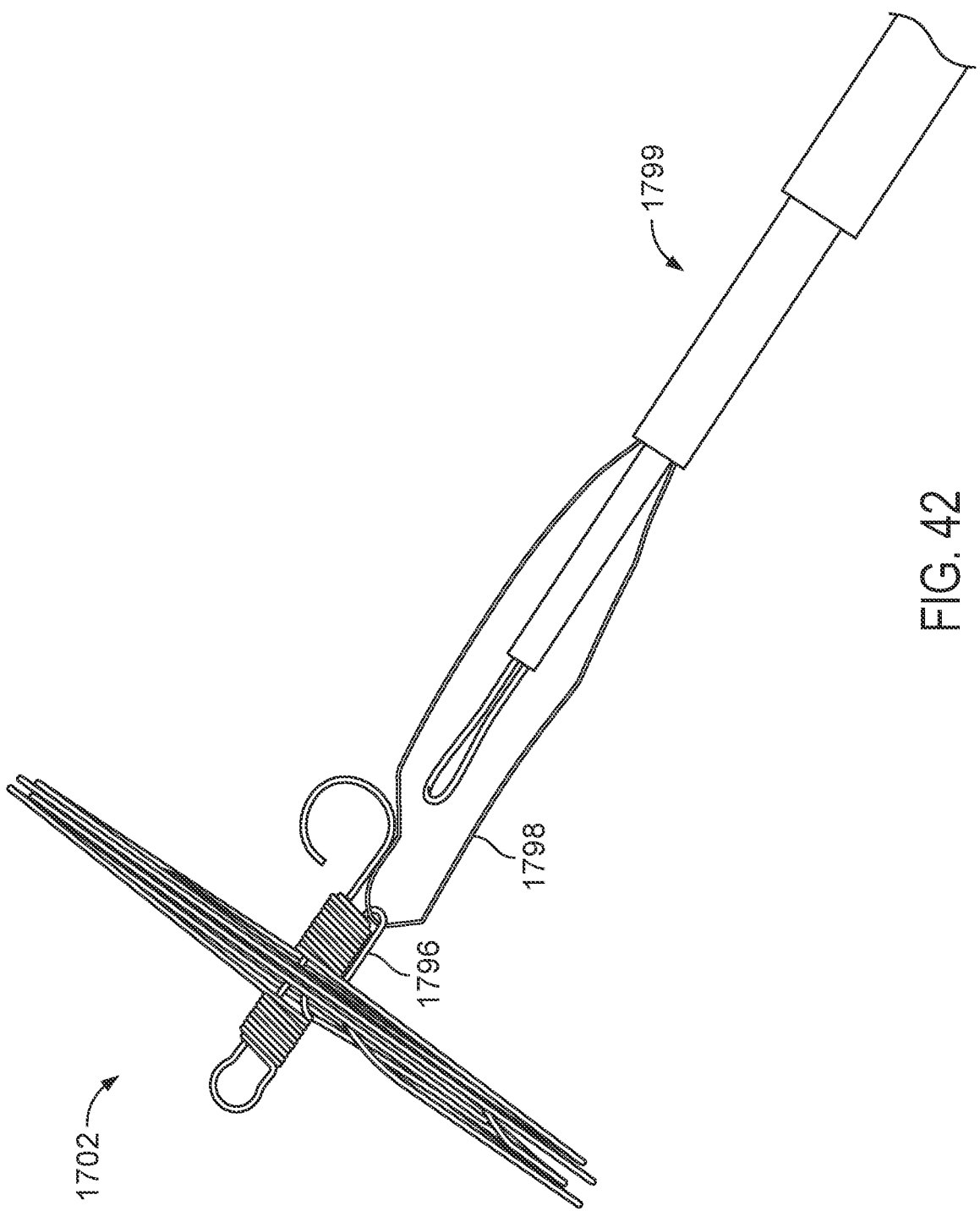
FIG. 42 is a view of an example sealing device and an example delivery apparatus.

FIG. 42 shows the device 1702 in a deployed configuration, where the device 1702 includes a non-metal attachment member 1796. Non-metal attachment member 1796 may be an ePTFE loop attached to an eyelet of the device 1702, for example. A retrieval cord 1798, which may comprise an ePTFE tether, of the delivery apparatus 1799 is looped through the non-metal attachment member 1796. As such, the device 1702 can be fully deployed while remaining coupled to the delivery apparatus 1799, so that an assessment of the deployment under a lower tension or tension-free (as compared to the device being more rigidly secured to the delivery apparatus) may be performed. If the deployment is unsatisfactory, the device 1702 can be recaptured by the delivery apparatus 1799 by drawing the device 1702 into the apparatus using the retrieval cord 1798. In some examples, fraying of the retrieval cord 1798 may be minimized or avoided because of the non-metal-on-non-metal interface of retrieval cord 1798 and non-metal attachment member 1796. In general, non-metal attachment member 1796 and retrieval cord 1798 can comprise any biocompatible material of sufficient strength and flexibility. In some examples, a metal attachment member can be used. In some examples, the retrieval cord 1798 is looped through an eyelet of the device 1702.

Some embodiments include left and right discs interconnected by a defect occupying region. The discs may be soft and conformable, and the nominal diameters of the left and right discs may be substantially equivalent. The device may be preassembled to a delivery system. The devices may include fewer than ten Niti wires. The devices may include a small amount of metal mass. The devices may be versatile. For example, defect size ranges from 8 mm to 35 mm, such as for atrial septal defects, and more specifically for ostium secundum atrial septal defects, may be treated with five device sizes, in some implementations. The devices may be deployed by a handle deployment system with simple push/pull motions for loading and deployment. In some embodiments, the metal frame of the device may not be exposed to the bloodstream. A delivery catheter with both multi-purpose and Hausdorf-type curves may be used. A 10 Fr. (outer diameter) catheter may be used. An 11 Fr. (outer diameter) catheter may be used. A 12 Fr. (outer diameter) catheter may be used.

In general, the sealing devices described herein (including devices 1702, and 1780) may be implanted using a percutaneous, transcatheter procedure. The sealing device may be loaded or attached to a delivery apparatus, for example as described above herein. In some examples, the sealing device may be loaded or attached to a delivery catheter that is controlled by a control handle, for example. The delivery apparatus may be advanced to a location of defect or structure in a heart of a patient, and the sealing device may be deployed at the location of the defect or structure to seal the defect or structure. In some examples, the defect or structure may be an atrial septal defect. I some examples, the defect or structure may be an ostium secundum defect. In some examples the defect or structure may be a patent foramen ovale defect.

In some examples, the sealing device may be attached or loaded to a delivery catheter, which may be advanced over a guidewire across the atrial septum until the tip of the delivery catheter is positioned within the left atrium. The guidewire may be removed. A first action at a handle of a delivery system that is coupled to the delivery catheter may deploy the left occluding member (e.g., left disc) of the sealing device from the catheter. In some examples, the first action may include moving a slider control on the handle in a first direction until the slider control encounters a stop. This action may be performed simultaneously with retracting the delivery catheter a distance. In some examples, the first action may also include moving the slider control in a second direction that is different from the first direction (e.g., perpendicular to the first direction) and then again in the first direction until a tactile cue at the handle is encountered, which may indicate to an operator that the left occluding member has been deployed. The operator may give the handle a gentle tug to bring the left occluding member into contact with the left atrial septum. A second action at the handle may deploy the right occluding member (e.g., right disc). In some examples, the second action may include moving the slider control in the first direction until the slider control encounters a stop, and then moving the slider control in a third direction that is different from the first and second directions (e.g., opposite of the second direction). A third action at the handle may cause the sealing device to be locked into place at the delivery location, as by locking the lock loop of the device.

While several of the example sealing devices discussed herein have generally been described as comprised of elongate elements or wires, in alternative embodiments any of the sealing devices discussed herein may also be formed from a tube, such as laser-cut from a Nitinol tube. For example, a laser may be used to cut a pattern into a hollow tube to create a sealing device that resembles the wire-wound sealing devices discussed herein, where portions of the tube remaining after the pattern has been cut may correspond to the elongate elements or wires of the devices discussed herein. A Nitinol tube having an outer diameter sized to correspond to the eyelet or elongate element aggregation elements discussed herein may be laser-cut in this manner, for example. For additional examples of devices created by laser-cutting a tube of material, see the provisional patent application titled "Space Filling Devices," having inventors Coby C. Larsen, Brandon A. Lurie, Steven J. Masters, Thomas R. McDaniel, and Stanislaw L. Zukowski, filed on 16 Nov. 2012, assigned U.S. Ser. No. 61/727,458, and the provisional patent application titled "Space Filling Devices," having inventors Coby C. Larsen, Brandon A. Lurie, Steven J. Masters, Thomas R. McDaniel, and Stanislaw L. Zukowski, filed on 15 Mar. 2013, the disclosures of which are considered part of and are specifically incorporated by reference in their entirety (including the figures) for all purposes in the present disclosure.

While several of the example sealing devices discussed herein have generally been described as including eyelets or wire aggregation elements at or near the proximal or distal ends of the device, other examples are possible. In some embodiments, one or both eyelets or wire aggregation elements may be oriented toward the center of the device rather than toward the proximal or distal ends of the device. For examples of devices that include eyelets oriented toward the center of the device, or for other styles of wire aggregation elements (which may be used to replaced, e.g., eyelets or wire aggregation elements discussed herein), see the provisional patent application titled "Space Filling Devices," having inventors Coby C. Larsen, Brandon A. Lurie, Steven J. Masters, Thomas R. McDaniel, and Stanislaw L. Zukowski, filed on 16 Nov. 2012, assigned U.S. Ser. No. 61/727,458, and the provisional patent application titled "Space Filling Devices," having inventors Coby C. Larsen, Brandon A. Lurie, Steven J. Masters, Thomas R. McDaniel, and Stanislaw L. Zukowski, filed on 15 Mar. 2013, the disclosures of which are considered part of and are specifically incorporated by reference in their entirety (including the figures) for all purposes in the present disclosure. For additional examples of wire aggregation elements or hub elements (which may be used to replaced, e.g., eyelets or wire aggregation elements discussed herein), see the provisional patent application titled "Joint Assembly for Medical Devices," having inventors Coby C. Larsen, Steven J. Masters, and Thomas R. McDaniel, filed on 16 Nov. 2012, assigned U.S. Ser. No. 61/727,328, and the non-provisional patent application titled "Joint Assembly for Medical Devices," having inventors Coby C. Larsen, Steven J. Masters, and Thomas R. McDaniel, filed on 15 Mar. 2013, the disclosures of which are considered part of and are specifically incorporated by reference in their entirety (including the figures) for all purposes in the present disclosure. For additional examples of delivery system devices, systems, and techniques that can be used to deliver, deploy, reposition, and retrieve the devices discussed herein, see the provisional application titled "Implantable Medical Device Deployment System," having inventors Steven J. Masters and Thomas R. McDaniel, filed on 16 Nov. 2012, assigned U.S. Ser. No. 61/727,328, and the provisional patent application titled "Implantable Medical Device Deployment System," having inventors Steven J. Masters and Thomas R. McDaniel, filed on 15 Mar. 2013, the disclosures of which are considered part of and are specifically incorporated by reference in their entirety (including the figures) for all purposes in the present disclosure.

Figure 26A:
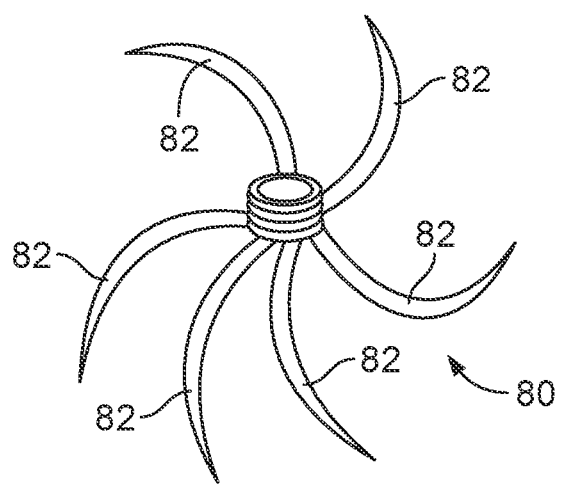
FIGS. 26A-C illustrate an anchor component and method of attaching anchor component to a sealing device.
Figure 30:
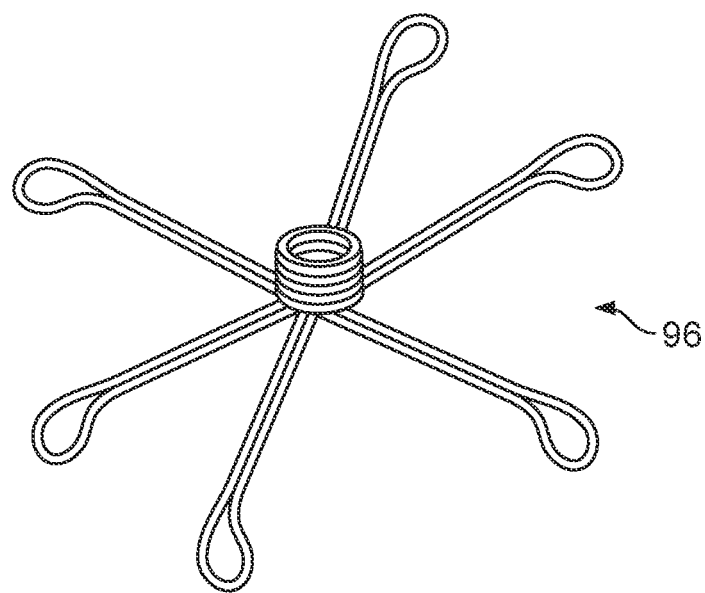
FIG. 30 is a perspective view of an anchor component.

Anchor components or fixation devices may be attached to any of the embodiments. Examples of anchor complements (80 and 96) are shown in FIGS. 26A and 30. FIG. 26A illustrates an anchor component 80 with fixation elements configured to pierce, puncture or protrude into tissue adjacent to the device during or after deployment. Anchor component 96 in FIG. 30 illustrates fixation elements configured with blunt ends designed to grasp or engage the adjacent tissue without substantially protruding into the tissue. Other anchor components may be envisioned, including anchor components configured to possess both piercing and grasping capabilities. Such an anchor component may be similar to that shown in FIG. 30, but instead of having looped wire arm, have a single wire arm with a looped end, the end of which may be crimped or positioned to either be in the same plane as the single wire arm or to protrude from the plane thereby being available to pierce or puncture tissue. Anchor components may be attached at any eyelet of the device. Anchor components may be configured to bend in any direction. Single or multiple anchor components may be affixed to any device or wire frame in any combination. Said anchors can be designed to release the tissue for repositioning and/or retrieval. Further, when the sealing device is in a delivery configuration, the barbs may be collapsed to avoid catching on the catheter components during retrieval of the device.

For additional examples of anchors and sealing devices, see U.S. application Ser. No. 13/291,914, titled "Sealing Device and Delivery Method," the contents of which are hereby incorporated by reference in their entirety for all purposes.

Figure 8:
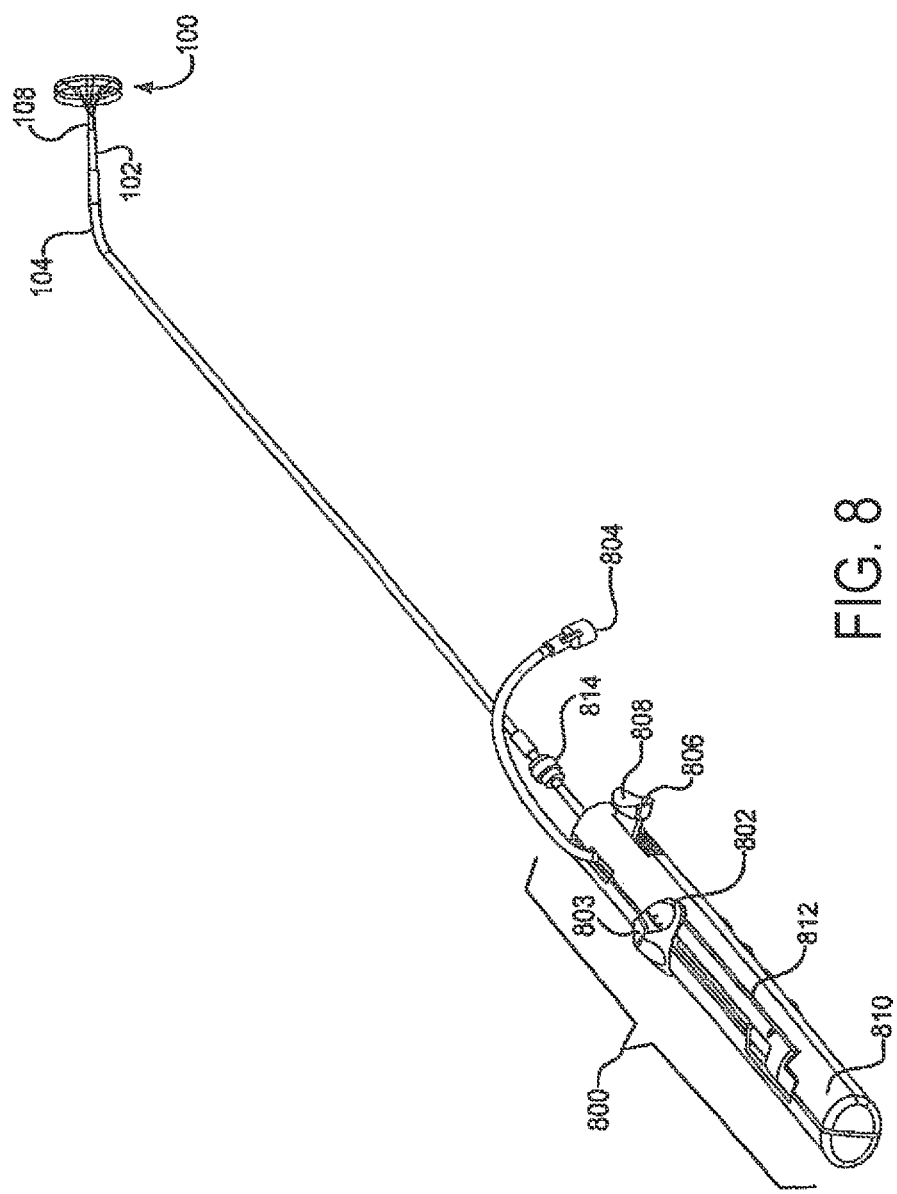
FIG. 8 is a perspective view of a delivery system including a deployment handle and attached sealing device.

FIG. 8 shows a perspective view of sealing device 100 attached to a delivery system including first tube 102, third tube 104, and a handle for deploying a sealing device 100. FIG. 8 further illustrates a first linear actuator 802, a flushing port 804, the second linear actuator 806, lock release actuator 808, a housing 810 and a slot with a length in the housing 812. First linear actuator 802 may have a variety of configurations, which will be discussed further.

Figure 10:
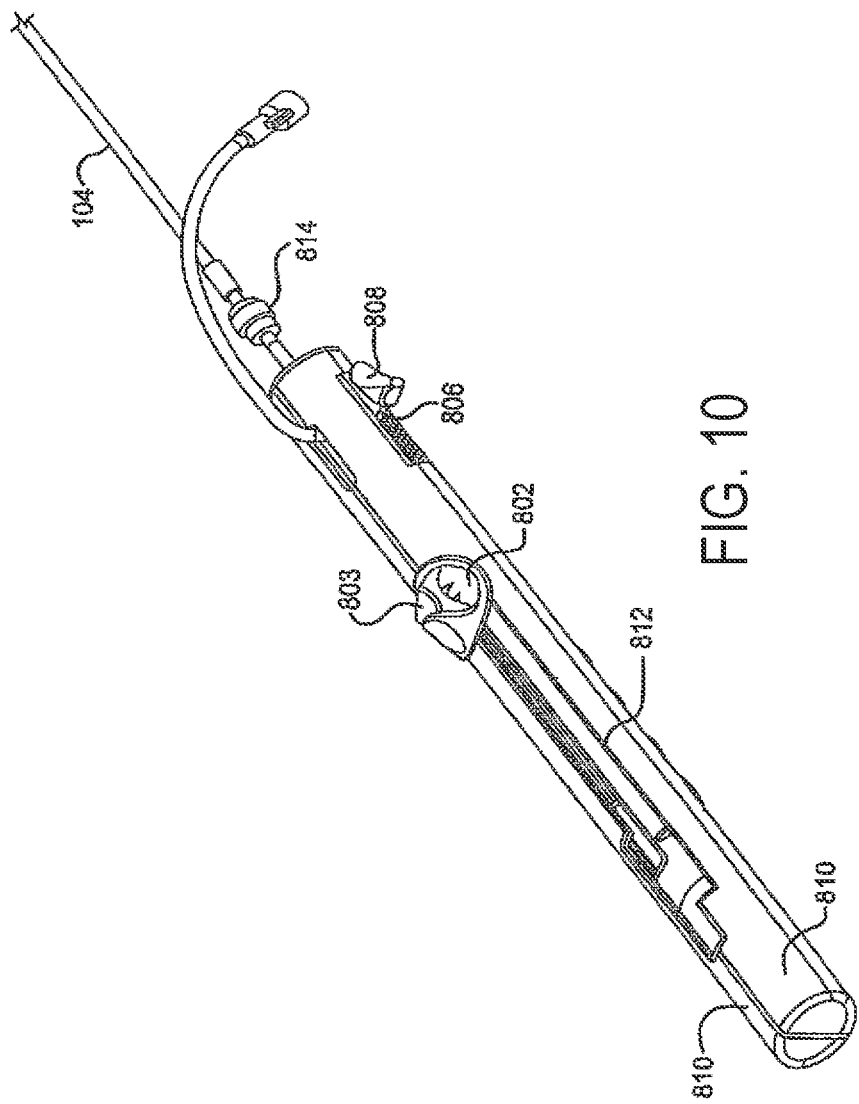
FIG. 10 is a perspective view of a sealing device deployment handle.
Figure 11:
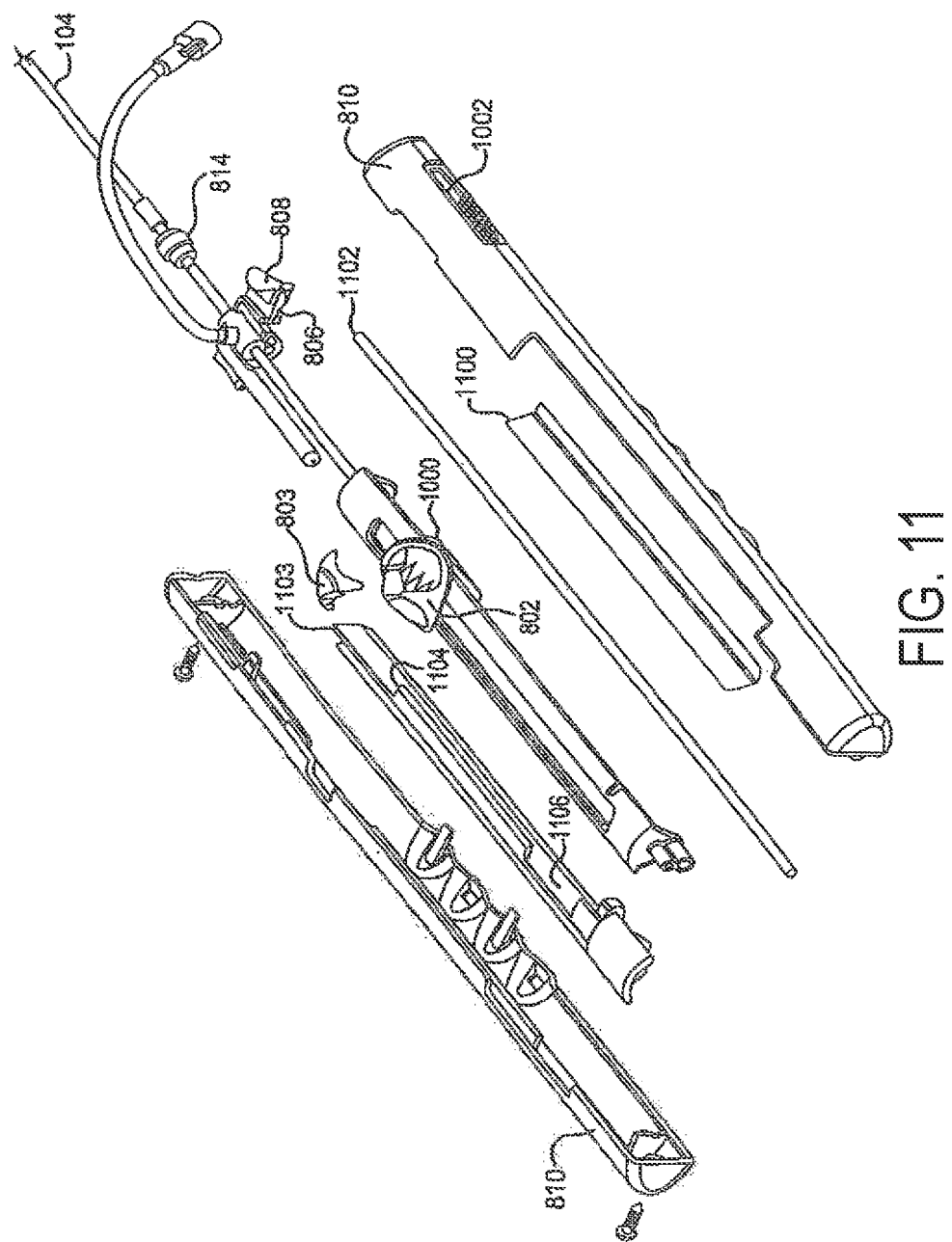
FIG. 11 is a perspective view of an assembly of a sealing device deployment handle.

FIGS. 9A-D are flow charts which describe the movements of the various components of the delivery system and attached sealing device 100 during use. Loading sealing device 100 into the delivery system prior to use is described in FIG. 9A. Components of the delivery system handle are shown in FIGS. 8, 10 and 11. A clinician may flush the delivery system by attaching a syringe or other suitable implement onto flushing port 804 and filling the system with saline or any other appropriate flushing material. The first linear actuator 802 may then be moved in slot 812 in housing 810 against a spring 1100. Spring 1100 may be configured as shown or may be formed as a leaf spring, stepped spring or any form commonly known in the arts. This action rotates the mandrel control lever 1000, shown in FIG. 11, about a slider rod 1102 to the side of housing 810. This same motion moves the first linear actuator 802 free of distal notch 1104 in the sizing insert 1103 and prevents the second tube 108 from translating either proximally or distally. Sizing insert 1103 may be of any material with suitable mechanical properties.

Typical handles, handle components, tools or catheters used to deliver medical devices can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE),Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

A distal notch 1104 and proximal notch 1106 in sizing insert 1103 may be used to aid in the positioning of the first linear actuator 802 in housing slot 812. The distance between the two notches, 1104 and 1106 respectively, may be the length of sealing device 100 when it is elongated over second tube 108 prior to loading onto the delivery system. Sizing insert 1103 may be sized to accommodate a variety of device lengths and is preferably from about 22.28 cm long with a distance between the proximal end of distal notch 1104 and proximal end of proximal notch 1106 from about 6.25-13.32 cm. Notches 1104 and 1106 may be of any shape but are preferably rectangular.

The first linear actuator 802 is then moved to a mid point in slot 812 toward the proximal end of the housing 810. This action causes the first tube 102 to move proximally and the sealing device 100 proximal end to move proximally, thus elongating sealing device 100. First linear actuator 802 may be any shape (e.g., lever, ball) but is preferably shaped to accommodate a clinician's thumb. First linear actuator 802 may be constructed of any material with suitable mechanical properties but is preferably a material similar to that of sizing insert 1103. A feature of the first linear actuator 802 are recessed teeth formed in the top portion of the first linear actuator 802 for securing retrieval cord 110. This feature is preferred but optional. The teeth could be made into any tortuous path or have any shape desired to create resistance for retrieval cord 110 during loading, deployment, or retrieval of sealing device 100. Corresponding protruding teeth (not shown) may be formed in the bottom surface of retrieval cord lock 803. These teeth may fit together and hold the retrieval cord firmly. Other methods commonly known in the art for securing a small diameter cord may also be used and will be discussed in detail in a following section.

The first linear actuator 802 is then moved further proximally until the device is loaded in third tube 104. During this action, spring 1100 pushes the first linear actuator 802 and the mandrel control lever 1000 to the left of slot 812 and into the proximal notch 1106 in sizing insert 1103. The second tube 108 is free to move proximally with sealing device 100 and first tube 102. As the first linear actuator 802 is moved proximally, the second tube 108, sealing device 100 and first tube 102 slide or translate into the third tube 104. After the first linear actuator 802 is in its proximal-most position, the system may again be flushed with saline in the manner described above.

Figure 12A:
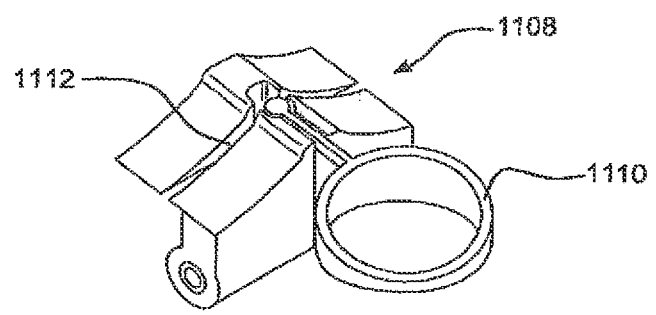
FIG. 12A is a top down view of an embodiment of a first linear actuator.
Figure 12B:
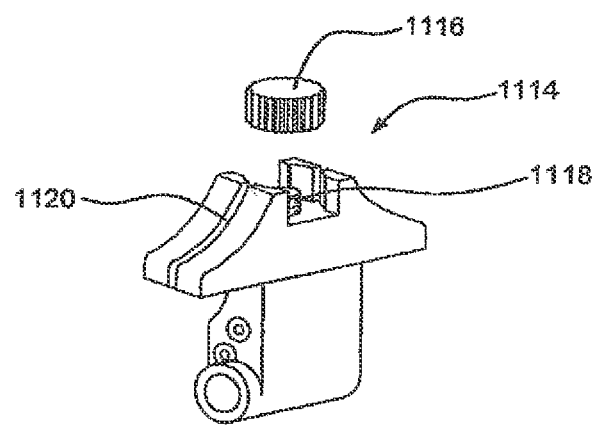
FIG. 12B is a side view of an embodiment of a first linear actuator.
Figure 12C:
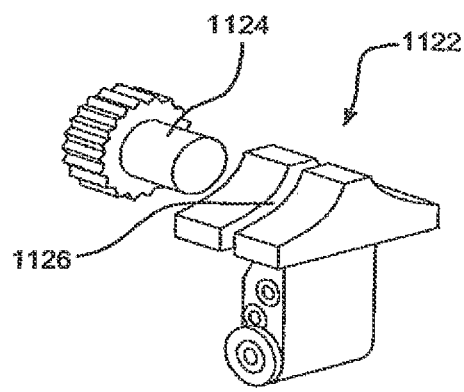
FIG. 12C is a side view of an embodiment of a first linear actuator.
Figure 12D:
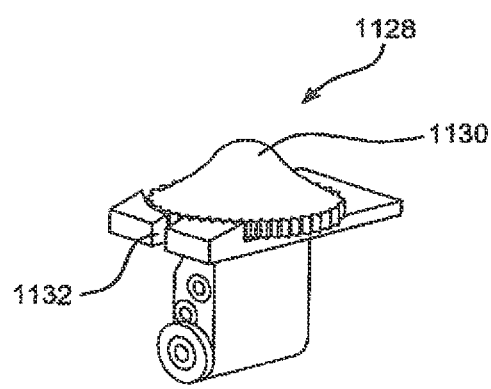
FIG. 12D is a side view of an embodiment of a first linear actuator.

Alternate embodiments of first linear actuator 802 are shown in FIGS. 12A-D. FIG. 12A shows a perspective view of the alternate linear actuator 1108 in the locked retrieval cord position. Linear actuator 1108 is similar in construction to linear actuator 802 but features a retrieval cord locking ring 1110 and retrieval cord groove 1112. FIG. 12B depicts alternate embodiment 1114, which is configured with a thumb wheel 1116 that extends beyond the sides of the linear actuator to facilitate easy manipulation. Thumb wheel 1116 is screwed onto a threaded post 1118 around which the retrieval cord is wound. Embodiment 1114 also contains a retrieval cord groove 1120 through which the retrieval cord is guided prior to securing it around threaded post 1118. FIG. 12C illustrates yet another embodiment 1122 that utilizes a side fitted threaded thumb wheel 1124 around which the retrieval cord is wound and secured to the actuator 1122 by the act of inserting the threaded post 1124 into a threaded aperture (not shown) in the side of the actuator 1122. Prior to threading the retrieval cord around the threaded post 1124, the retrieval cord is inserted through the retrieval cord groove 1126. Yet another embodiment 1128 is shown in FIG. 12D. Embodiment 1128 shows a linear actuator with molded thumb wheel 1130. The thumb wheel 1130 extends slightly beyond the edges of the linear actuator facilitating manipulation of the linear actuator. The retrieval cord is inserted through cord groove 1132 and wound around a threaded post (not shown). The molded thumb wheel 1130 is then secured on the threaded post securing the retrieval cord.

Deploying sealing device 100 into a defect is described in FIG. 9B. The first linear actuator 802 is moved distally until a stop is reached. This movement causes the first tube 102 and second tube 108 to move distally within the third tube 104. The linear actuator 802 must then be moved to the right in slot 812, against spring 1100. When the linear actuator 802 is moved to the right, mandrel control lever 1000 rotates on slider rod 1102. This action causes the linear actuator 802 to be free of the proximal notch 1106 in sizing insert 1103. After this action, the linear actuator 802 is further translated distally. This causes the first tube 102 and proximal eyelet 202 of sealing device 100 to move distally. Also affected by this action is the distal end of sealing device 100, which is prevented from moving. The first tube 102 guides the device out of the third tube 104 to deploy the device in a defect. Moving linear actuator 802 distally to the end of slot 812 results in the entire sealing device being deployed. One skilled in the art would recognize that the steps described above could be halted and reversed at certain points to allow optimal positioning of sealing device 100.

Locking the device is described in the flowchart illustrated in FIG. 9C. The retrieval cord lock 803 would be unsnapped from the first linear actuator 802. A clinician would grasp the second linear actuator 806 by gripping attached lock release actuator 808 and press it toward the middle of housing 810. The second linear actuator 806 may be of any size or shape but is preferably sized to fit within a slot 1002 in the longitudinal surface of housing 810. Linear actuator 806 is fitted with lock release actuator 808 by means of a snap fitting. Any means of attachment would suffice to fasten lock release actuator 808 to linear actuator 806, such as glue or construction as a molded part. Materials appropriate for both the second linear actuator 806 and lock release actuator 808 may be any material of suitable mechanical properties, but are preferably similar to that of the previously mentioned handle components. Lock release actuator 808 is designed to enable a user to grip the device securely. Gripping may be aided by protrusions on the lateral sides of the lock release actuator 808. These protrusions may be made of a similar material as that of the lock release actuator 808, or may be made of a material with a high coefficient of friction or of a material more compliant than that of lock release actuator 808. These protrusions may also be made with grating, a roughening, a raised design, or striations in the surface in conjunction with the material listed above to further aid in the gripping of the device. These features on the surface of lock release actuator 808 may also be used to aid in gripping without the use of gripping protrusions, and may be applied directly to the lateral surface of the second linear actuator 806. Slot 1002 may be configured to have a stop to hold the second linear actuator 806 in a distal most position until lock release of the sealing device. A preferred stop is shown in FIGS. 10 and 11 in the form of a corrugated area, but may also be any manner of mechanical stop. Slot 1002 may be of any length, but preferably has a length sufficient to translate motion proximally about the width of the second linear actuator 806 plus about 3.18 cm. Slot 1002 may be any shape that would accommodate the second linear actuator 806.

Figure 13A:
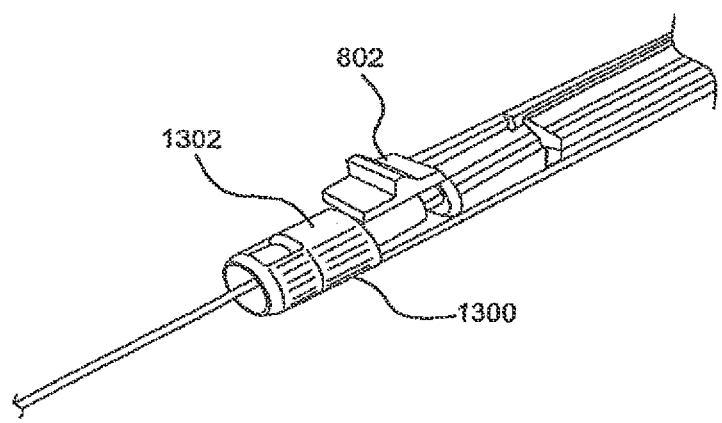
FIG. 13A is a perspective view of an embodiment of a lock release actuator.
Figure 13B:
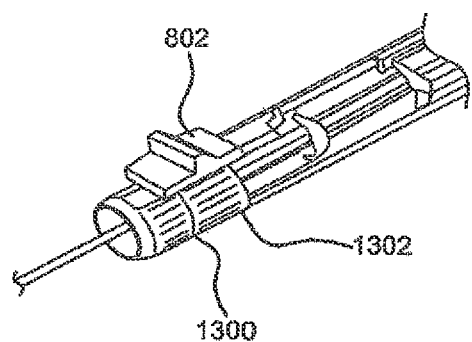
FIG. 13B is a perspective view of an embodiment of a lock release actuator in the activated position.

An alternate embodiment of second linear actuator 806 is shown in FIGS. 13A and 13B. Instead of gripping lock release actuator 808 and activating second linear actuator 806, a rotatable lock release actuator 1300 is gripped and rotated to affect lock release. The rotatable lock release actuator 1300 may contain a window 1302, which would prevent forward movement of the first linear actuator 802. When rotated, lock release actuator 1300 allows the same actions as lock release actuator 806 shown in FIG. 10.

Once the second linear actuator 808 is gripped, a clinician may move the second linear actuator 806 proximally. This action results in proximal movement of third tube 104, mandrel control lever 1000, sizing insert 1103 and second tube 108. Second tube 108 moves proximally from between eyelets of the device. An alternate method of achieving this action would be to provide a twist mechanism to the distal end of the handle instead of a second linear actuator 806. This twist mechanism would be provided with a slot that allows for the same movement of the third tube 104, mandrel control lever 1000, sizing insert 1103 and second tube 108 as the second linear actuator 806.

Once lock release has been achieved, the retrieval cord lock 803 is then twisted to remove it from the first linear actuator 802 and pulled until the retrieval cord 110 is free of the delivery system. Retrieval cord 110 is attached to the retrieval cord lock 803 at one end. Retrieval cord 110 may be constructed of any material with suitable mechanical properties such as Kevlar®, flexible metal wire, polymers and the like. A preferred material for retrieval cord 110 is an ePTFE fiber. Retrieval cord lock 803 may be configured in a variety of shapes and sizes. Possible retrieval cord locks may be designed to provide a slot in the linear actuator 802 through which the retrieval passes. In one configuration, the retrieval cord is secured by passing the cord through a slot or hole in the axis of the thumb wheel disposed in the linear actuator 802 and tightened by twisting the thumb wheel. An alternate configuration would provide a slide lock that binds the retrieval cord between the lock and the linear actuator 802 using friction. A preferred design would be to secure the retrieval cord between teeth formed in the retrieval cord lock as shown in FIG. 11.

Materials suitable for constructing retrieval cord lock 803 are similar to that used to construct housing 810 and other handle components. As mentioned previously, retrieval cord lock 803 preferably has teeth or protrusions that correspond to indentations in linear actuator 802 for the purpose of gripping retrieval cord 110. Retrieval cord lock 803 may be configured in a variety of shapes to enable retrieval cord 110 to be secured. A preferred configuration would include apertures through the retrieval cord lock 803 to allow retrieval cord 110 to be threaded therethrough and knotted. After twisting the retrieval cord lock 803, it is pulled until the retrieval cord 110 is removed from the delivery system.

Figure 14A:
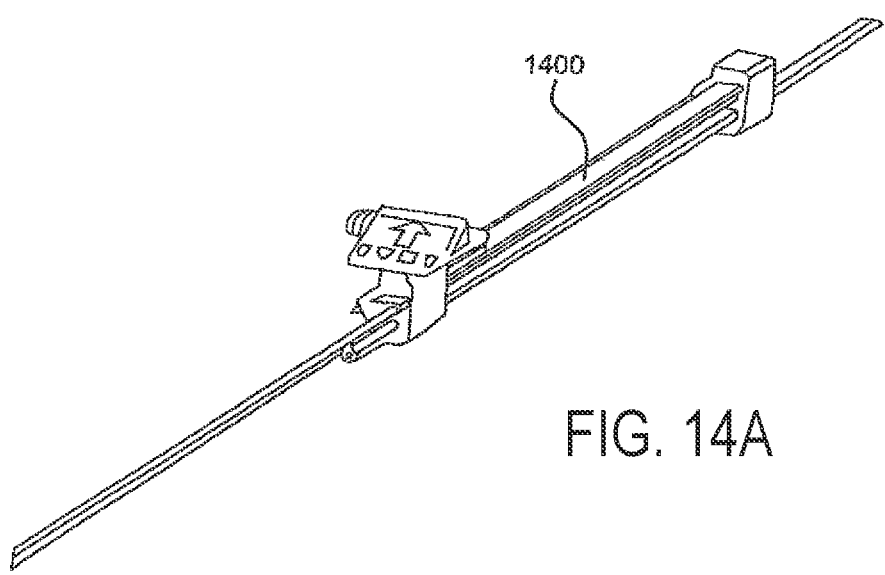
FIG. 14A is a perspective view of an embodiment of a spring.
Figure 14B:
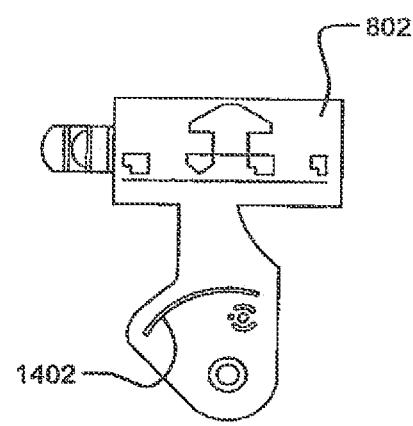
FIG. 14B is an end on view of an embodiment of a first linear actuator.
Figure 15:
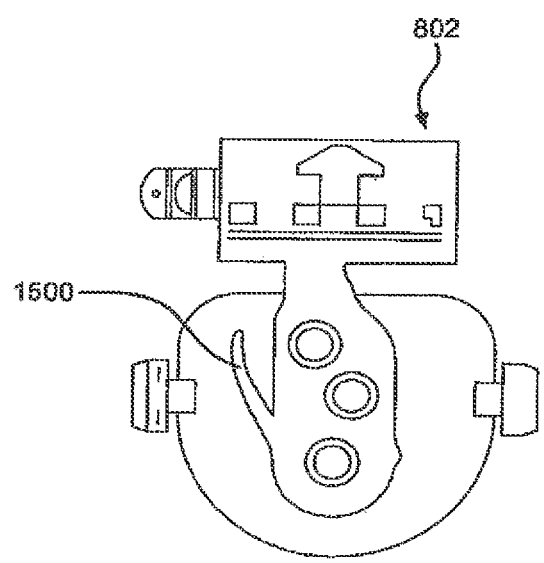
FIG. 15 is an end on view of an embodiment of a first linear actuator with molded spring component.
Figure 16:
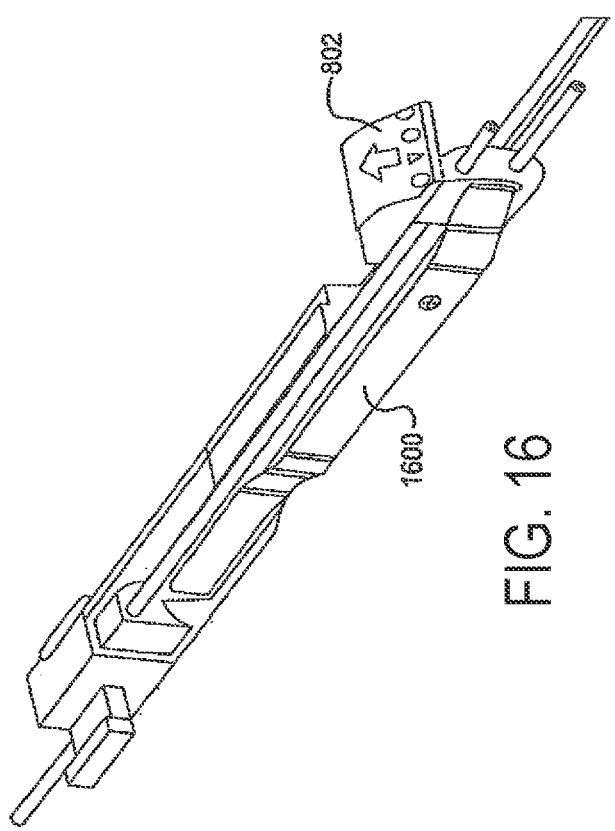
FIG. 16 is a perspective view of a spring component.

Prior to the step four described in FIG. 9C, the sealing device 100 may be retrieved as described in the flowchart illustrated in FIG. 9D. The retrieval cord lock 803 may be snapped into the first linear actuator 802. This serves to lock the retrieval cord 110 in place. The clinician then moves the first linear actuator 802 to the right edge of slot 812. The first linear actuator 802 moves in slot 812 to the right, pressing on spring 1100 while the mandrel control lever 1000 rotates on the slider rod 1102 to the right of the handle. Slider rod 1102 is preferably of a round cross-section but one skilled in the art would recognize that a variety of cross-sectional shapes (e.g., square or triangular) would be acceptable. Slider rod 1102 could also be configured in the shape of a crown spring 1400, as shown in FIGS. 14A and B. The spring could be inserted in a slot 1402 through the linear actuator to allow fore and aft translation of the linear actuator. An alternate embodiment of spring 1100 may be a spring molded as an integral part 1500 of first linear actuator 802, as illustrated by FIG. 15. Another embodiment of spring 1100 is shown in FIG. 16. In this configuration, a spring 1600 is attached to housing 810 and pushes on the first linear actuator 802 in key positions. As stated above, one skilled in the art would recognize the appropriate materials for use as a spring or molded part. The first linear actuator 802 is free of distal notch 1104 and the second tube 108 is prevented from moving. The first linear actuator is moved proximally by the clinician, causing first tube 102 to move proximally. This motion translates the proximal end of sealing device 100 proximally elongating the device 100 and allowing it to be pulled into the third tube 104.

EXAMPLES

Without intending to limit the scope of the invention, the following examples illustrate how various embodiments of the invention may be made and/or used.

Example 1

A sealing device similar to FIG. 1 was manufactured using the following components and assembly process.

An expanded polytetrafluoroethylene material was obtained with the following properties:
  Methanol bubble point of 1 psi
  Mass/area of 2.2 grams/square meter
  Longitudinal maximum load of 1.6 kg/inch
  Thickness of 0.0003 inch
  Longitudinal matrix tensile strength of 92000 psi The following test methods and equipment were used to determine the above-mentioned properties: Methanol bubble point was measured using a custom built machine with a 1 inch diameter foot, a ramp rate of 0.2 psi/second and a liquid media of methanol. Length and width of the material were measured using a metal ruler. Mass/area was measured using a balance (Model GF-400 Top Loader Balance, ANG, San Jose CA.) with a 36×5 inch sample. Longitudinal maximum load was measured using a materials test machine (Model 5564, Instron, Grove City, PA) equipped with a 10 kg load cell. The gauge length was 1 inch and the cross head speed was 25 mm/minute. Sample width was 1 inch. Longitudinal tensile test measurements were taken in the length direction of the material. Thickness was measured using a thickness gauge (Mitutoyo Digital Indicator 547-400) with a foot diameter of ¼ inch. The longitudinal matrix tensile strengths (MTS) were calculated using the following equation: Density was calculated using the formula, density=mass/volume.

$$\text{Matrix Tensile Strength} = \frac{(\sigma_{sample}) * (\rho_{PTFE})}{(\rho_{sample})}$$

where: $\rho_{PTFE} = 2.2$ grams/cc $\sigma_{sample} = $ (Maximum Load/Width)/Thickness $\rho_{sample} = $ (Mass/Area)/Thickness An expanded polytetrafluoroethylene with a thin layer of FEP (fluorinated ethylene propylene) material was obtained with the following properties:
  Mass/area of 36.1 grams/square meter
  Maximum Load, Longitudinal of 12.6 kg/inch
  Maximum Load, Transverse of 0.3 kg/inch
  Thickness of 0.0012 inch The following test methods and equipment were used to determine the above-mentioned properties: Material was weighed using a precision analytical balance (Model GF-400 Top Loader Balance, ANG, San Jose CA.) with a sample area of 36×1 inch sample. Length and width of the material were measured using a metal ruler. Material thickness was measured using a digital thickness gauge (Mitutoyo Digital Indicator 547-400) with a foot diameter of ¼ inch. Maximum transverse load was measured using a materials test machine (Model 5564, Instron, Grove City, PA) equipped with a 10 kg load cell. The sample width was 1 inch, the gauge length was 1 inch and the cross head speed was 25 mm/minute. Maximum longitudinal load was measured using a materials test machine (Model 5564, Instron, Grove City, PA) equipped with a 200 kg load cell. The sample width was 1 inch, the gauge length was 1 inch and the cross head speed was 25 mm/minute. Longitudinal tensile test measurements were taken in the length direction of the material and transverse tensile test measurements were taken in the direction orthogonal to the length direction.

A distal eyelet was formed by first obtaining a length of 10% platinum drawn filled nitinol wire (Fort Wayne Metals, Fort Wayne, IN.) with a diameter of about 0.23 mm. This wire was labeled "first wire". A free end of the first wire was doubled on itself to create an open-ended loop and the open-ended loop was inserted into the button. The button was then inserted onto the keyed center pin. The button was shaped to have an opening through the center to accommodate the keyed center pin and to have features that allow it to rest securely in the winding jig. The keyed center pin (major axis of about 0.51 mm and minor axis of about 0.25 mm and length of about 10.16 mm) was then inserted in the center of a winding jig. The keyed center pin was fabricated from high strength steel (Super Cobalt HSS Tool Bit, MSC #56424278, Seco Fagersta). The steel was tempered per manufacture's instructions at 1475° F. for one hour. The winding jig and button were fabricated in house from corrosion resistant tool steel.

A second length of the same type of drawn filled nitinol wire was obtained and labeled "fifth wire". The first, fifth and an additional three wires were tensioned by attaching weights to the wire ends. The first wire and the fifth wire were then wound around the free end of the first wire one full revolution. The three additional wires were introduced to the winding jig and all five wires were wound around the free end of the first wire to a height of about 1.98 mm.

A distal disk was then formed by separating the five wires and securing them in radial grooves around the circumferential edge of the winding jig. A radius was formed with the dimensions of 15 mm. Each wire formed one petal of the distal disk. The radius on the curvature of the petals was maximized in order to minimize sharp bend angles in the wire.

A center eyelet was formed by grouping the wires together and winding them around the free end of the first wire and the keyed center pin to a height of about 1.98 mm. The wires were then separated and secured in radial grooves around the circumferential edge of the winding jig, creating a proximal disk with a radius of 15 mm.

A proximal eyelet was formed by again grouping the five wires and winding them around the free end of the first wire and the keyed center pin to a height of about 1.98 mm. The five wires were then separated and secured by placing a stainless steel plate on top of the wires and locking down the plate with screws. The free end of the first wire was then wound one revolution around a stainless steel pin with a diameter of about 3.18 mm and secured similarly to the other five wires.

The jig with sealing device was then removed from the stabilizing fixture and placed in an oven (BlueM SPX Electric Forced Air Convection Oven), and the wires were thermally shape set as commonly known in the arts. The device and jig were then water quenched. The secured wires were released from the securing plate, and the device was chilled and removed from the jig and keyed center pin. The device was then placed on a piece of flattened PEEK (polyetherether ketone), and trimmed by hand to the outer diameter of the distal eyelet. The lock loop was trimmed by hand to a point just beyond one complete revolution and pulled through the proximal and center eyelets.

The device was pushed from the PEEK mandrel onto a keyed stainless steel process mandrel with an oval cross section. The mandrel was produced from flattened stainless steel wire (Ft. Wayne Metals, Fort Wayne, IN) with an oval cross-section to have a 45° clockwise twist between the proximal eyelet and the center eyelet and a second 45° clockwise twist between the center eyelet and the distal eyelet.

The process mandrel and device were then placed in a stabilizing fixture, which was placed in a FEP powder coating machine (C-30, Electrostatic Technology, Inc., Bradford, CN) and processed until coated completely. Excess FEP powder was removed from the device. The FEP was vacuumed from the lock loop, process mandrel and bumper. The process mandrel and device were removed from the stabilizing fixture, placed into an oven and baked to set the FEP coating, as commonly known in the arts.

A hollow core film mandrel (35.99 mm O.D. 76.2 cm long stainless steel) was obtained. Expanded polytetrafluoroethylene material with a slit width of 22.22 mm was obtained and loaded onto a spiral wrapping machine. The machine was manufactured in house to wrap PTFE (polytetrafluoroethylene) material at any desired angle, tension and rate. The mandrel was loaded onto the wrapping machine and the material was wrapped three times around the circumference of the hollow core mandrel. The material was then wrapped around the mandrel at an angle of about 8° for the length of the mandrel. The direction of wrapping was reversed and the material over wrapped at the same angle. The third and fourth layers were wrapped in the same manner with the seams offset. The mandrel was removed from the wrapping machine, inserted in an oven and baked at 370° C. for 45 minutes. The wrapped mandrel was removed from the oven and allowed to cool to room temperature. The resulting PTFE tube was removed from the mandrel.

The PTFE tube was then cut to about 140 mm and hand stretched to a desired length of 155 mm. The PTFE tube was then pulled over the frame. The PTFE tube was then crimped onto the center eyelet and then crimped onto the distal and proximal eyelets.

An expanded polytetrafluoroethylene with a thin layer of FEP (fluorinated ethylene propylene) material was then wrapped four times around the eyelets, starting with the center eyelet. The wrapped eyelets were tacked into place using a soldering iron. The PTFE tube was then heat set for 3 minutes at 320° C. and trimmed to the outer most points of the proximal and distal eyelets. The device was removed from the mandrel.

Example 2

Figure 6:
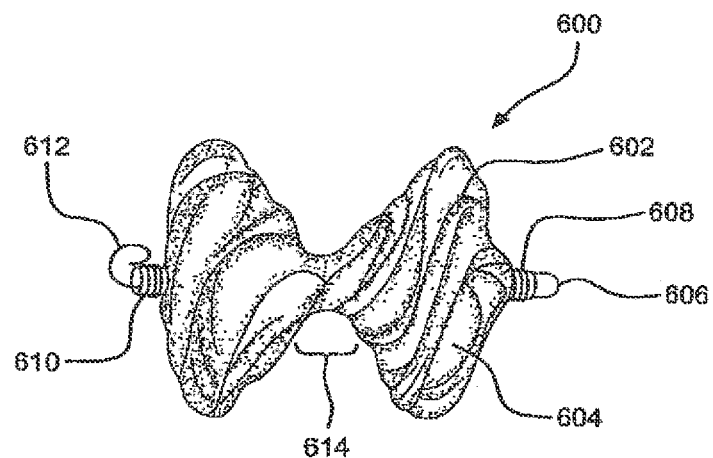
FIG. 6 is a side view of a self-centering embodiment of a sealing device.

A sealing device similar to FIG. 6 was manufactured using the following components and assembly process.

Expanded polytetrafluoroethylene and expanded polytetrafluoroethylene with a thin layer of FEP (fluorinated ethylene propylene) materials similar to that described in Example 1 were obtained.

A distal eyelet was formed by first obtaining a length of 10% platinum drawn filled nitinol wire (Fort Wayne Metals, Fort Wayne, IN.) with a diameter of about 0.23 mm. This wire was labeled "first wire". A free end of the first wire was doubled on itself to create an open-ended loop, and the open-ended loop was inserted into the button. The button was then inserted onto the keyed center pin. The button was shaped to have an opening through the center to accommodate the keyed center pin and to have features that allow it to rest securely in the winding jig. The keyed center pin (major axis of about 5.79 mm and minor axis of about 0.25 mm and length of about 10.16 mm) was inserted in the center of a winding jig. The keyed center pin was fabricated from high strength steel (Super Cobalt HSS Tool Bit, MSC #56424278, Seco Fagersta). The winding jig and button were fabricated in house from corrosion resistant tool steel.

A second length of the same type of drawn filled nitinol wire was obtained and labeled "fifth wire". The first, fifth and an additional three wires were tensioned by attaching weights to the wire ends. The first wire and the fifth wire were then wound around the free end of the first wire one full revolution. The three additional wires were introduced to the winding jig, and all five wires were wound around the free end of the first wire to a height of about 1.98 mm.

A device was then formed by separating the five wires and securing them in radial grooves around the circumferential edge of the winding jig. A radius was formed with the dimensions of 15 mm. Each wire made an entire revolution around the winding jig.

A proximal eyelet was formed by grouping the five wires and winding them around the free end of the first wire and the keyed center pin to a height of about 1.981 mm. The five wires were then separated and secured by placing a stainless steel plate on top of the wires and locking down the plate with screws. The free end of the first wire was then wound one revolution around a stainless steel pin with a diameter of about 3.18 mm and secured similarly to the other five wires.

The jig with sealing device was removed from the stabilizing fixture and placed in an oven (Blue M SPX Electric Forced Air Convection Oven), where the wires were partially thermally shape set as commonly known in the arts. The device and jig were then water quenched. The secured wires were released from the securing plate, and then the device was chilled and removed from the jig and keyed center pin. The lock loop was trimmed by hand to a point just beyond one complete revolution and pulled through the proximal and center eyelets.

The device was pushed from the PEEK mandrel onto a keyed stainless steel transfer mandrel with an oval cross section. The mandrel was produced from flattened stainless steel wire (Ft. Wayne Metals, Fort Wayne, IN) with an oval cross-section. The device was then partially removed from one end of the transfer mandrel. The removed device end was twisted approximately 180° clockwise and repositioned on the transfer mandrel. The device and transfer mandrel were placed in an oven (Blue M SPX Electric Forced Air Convection Oven), where the wires were thermally shape set as commonly known in the arts.

The transfer mandrel and device were then placed in a stabilizing fixture, which was placed in a FEP powder coating machine (C-30, Electrostatic Technology, Inc., Bradford, CN) and processed until coated completely. Excess FEP powder was removed. FEP powder was vacuumed from the lock loop, process mandrel and bumper. The transfer mandrel and device were then removed from the stabilizing fixture, placed into an oven and baked to set the FEP coating, as commonly known in the arts.

A hollow core film mandrel (35.99 mm O.D. 76.2 cm long stainless steel) was obtained. An ePTFE material with a slit width of 22.24 mm was obtained and loaded onto a spiral wrapping machine. The machine was manufactured in house to wrap ePTFE film at any desired angle, tension and rate. The mandrel was loaded onto the wrapping machine and the film was wrapped three times around the circumference of the hollow core mandrel. The ePTFE material was then wrapped around the mandrel at an angle of about 8° for the length of the mandrel. The direction of wrapping was reversed and the material over wrapped at the same angle. The third and fourth layers were wrapped in the same manner with the seams offset. The mandrel was removed from the wrapping machine, inserted in an oven and baked at 370° C. for 45 minutes. The wrapped mandrel was removed from the oven and allowed to cool to room temperature. The resulting ePTFE tube was removed from the mandrel.

The ePTFE tube was then cut to about 140 mm and hand stretched to a desired length of 155 mm. The ePTFE tube was then pulled over the frame. The ePTFE tube was then crimped onto the distal and proximal eyelets. An ePTFE with a thin layer of FEP (fluorinated ethylene propylene) material was then wrapped four times around the eyelets. The wrapped eyelets were tacked into place using a soldering iron. The ePTFE tube was then heat set for 3 minutes at 320° C. and trimmed to the outer most points of the proximal and distal eyelets. The device was then removed from the mandrel.

Example 3

A handle assembly similar to FIG. 8 was manufactured using the following components and assembly process.

Components for the handle assembly were fabricated using an injection molding process. The parts were fabricated by Contour Plastics (Baldwin, WI) using Lustran® 348. This material was suitable for use in medical devices and has an advertised tensile strength of 48.2 MPa and a tensile modulus of 2.62 GPa. Nine parts were fabricated using this injection process and Lustran® 348. The parts included the second linear actuator, flushing gasket retainer, a first linear actuator, retrieval cord lock, mandrel control lever, left body housing, sizing insert, right body housing, and a lock release actuator.

Other materials required for the assembly of the handle were purchased items. A catheter tube formed with a layup process commonly known in the arts was ordered (Teleflex Medical, Jaffrey, NH) with an I.D. of 0.048 mm and an O.D. of 0.33 mm and a platinum iridium marker band placed near the end of the distal tip. The main body of the catheter tube was Pebax® 7233 tube with PTFE liner and stainless steel braid (65 PPI) and the distal most 20.32 mm of the catheter tube was comprised of 6333 Pebax® (0.027 mm I.D. and an 0.033 mm O.D.) and a curve in the distal end (39.98 mm radius). A guidewire port formed by a laser was placed in the catheter tube proximal of the marker band. A flushing gasket or u-cup type gasket made of silicone (22.99 mm depth, I.D. tapered from 2.89 mm to 1.85 mm I.D. tapered from 6.71 mm to 7.75 mm) was procured from Apple Rubber of Lancaster, NY. A flushing port (Merit Medical, South Jordan, UT) having an about six inch flexible pvc (polyvinyl chloride) tube with a 3.18 mm O.D. female luer connector was obtained. A quick set cyanoacrylate adhesive was supplied from in-house stock. Stainless steel hypotubes were ordered from Small Parts, Inc. (1.45 mm O.D., 1.30 mm I.D., length of 30.48 cm.). Slider rods (PTFE coated stainless steel hypotubes, 3.18 mm O.D., 1.65 mm I.D., length of 33.02 cm) were procured from Applied Plastics. Control springs (PTFE-coated stainless steel leaf springs, thickness 0.10 mm, minor flange length 5.33 mm, major flange length 10.11 mm, overall length 15.88 mm) were ordered from Incodema of Ithaca, NY.

The remainder of the components were supplied from in house stock or manufactured in house. All triple lumen tubes were manufactured of Pebax® 7233 with 20% barium sulfate. Both triple lumen tubes had an O.D. (outer diameter) of mm. One triple lumen tube had round lumens with two I.D.s (inner diameters) of 0.035 mm and one I.D. of 0.15 mm. One triple lumen tube had one lumen with an oval cross-section with two I.D.s of 0.036 mm and one I.D of 0.127×0.07 mm. Stainless steel PTFE coated (polytetrafluoroethylene) process mandrels were manufactured in house. One process mandrel had a cross-sectional shape that transitioned from round (O.D. of 0.16 mm) to oval (O.D. of 0.14×0.07 mm). PTFE covered stainless steel wire was procured from in house stock (O.D. 0.03 mm). Standard luer fittings were obtained from in house stock. A PEEK (polyetheretherketone) second tube extrusion was obtained from in house stock with an oval cross-section of 1.27×0.69 mm O.D.

A first tube was made in the following manner. One triple lumen extruded tube with round lumens was obtained. Another triple lumen extruded tube was obtained with one lumen having an oval cross-section. A stainless steel processing mandrel was also obtained having a cross-sectional shape, which transitions from round (O.D. of 1.52 mm), to oval (O.D. of 1.39×0.81 mm). Both extruded tubes were loaded onto the mandrel, with the mandrel being inserted through the larger lumen on both tubes. Two small PTFE covered stainless steel wires were inserted through the smaller lumens of both extruded tubes. The mandrel and tubes were inserted into a RF (radio frequency) die (2.51 mm I.D., 4.45 mm length, fabricated from D2 tool steel). The junction of the two catheters was positioned in the center of the RF die. The RF die and mandrel was placed in the middle of an RF coil on an RF welding machine (Hot Shot I, Ameritherm Inc., Scottsville, NY) and welded as commonly known in the art. When the components had reflowed, pressure was applied to each end of the extruded tubes to meld the junction of the tubes. The die was then sprayed with compressed air to cool the die and to set the Pebax®. The extruded tube and die were removed from the RF machine, and the extruded tube was removed from the die. The process mandrel and wires were removed from the lumens of the extruded tube.

A lubricious coating may be applied to the second tube. A silicone mold release spray (Nix Stix X-9032A, Dwight Products, Inc., Lyndhurst NJ) may be sprayed onto about the distal 30 cm of the second tube and allowed to dry at ambient temperature under a fume hood.

A third tube sub-assembly was made in the following manner. A catheter tube was bisected with a straight razor at approximately 6.35 cm from the proximal end of the catheter tube. A male and female in-line luer connector (Qosina, Edgewood, NY) was obtained and drilled to an I.D. of 3.45 mm. U.V. (ultra-violet) cured adhesive (Loctite 3041) was applied to the bisected ends of the catheter tube and the drilled luer fittings were attached. The adhesive was cured per manufacture's instructions and the luer fittings were screwed together.

The second linear actuator sub-assembly was made in the following manner. The second linear actuator, flushing port, flushing gasket retainer and silicone flushing gasket were obtained. The flushing gasket was inserted into the back of the second linear actuator with the u portion of the flushing gasket facing distally. The flushing gasket retainer was fitted over the top inside the second linear actuator. Cyanoacrylate glue was applied around the gasket retainer to hold the gasket retainer in place. The flushing port was placed into an aperture in the second linear actuator and an U.V. cure adhesive was applied and cured according to manufactures instructions.

A first tube was obtained and cyanoacrylate was applied to the outside surface of the round I.D. section of the catheter in a 2.54 cm band from the end. The catheter was then inserted into the distal end of the control shuttle until the catheter became flush with the back of the control shuttle. The catheter was oriented so that the two small lumens were horizontal and on the top portion of the round lumen. The retrieval cord lock was snapped onto the control shuttle.

The second tube sub-assembly was manufactured in the following manner. A four inch piece of 0.033 mm diameter nitinol wire was inserted into the second tube extrusion. The second tube extrusion with wire insert was inserted into a hypotube. The distal end of the hypotube was crimped by hand three times.

The distal end of the first tube was threaded through the top of the mandrel control lever and through the top aperture on the distal end of the mandrel control lever. The distal end of the second tube was threaded into the proximal end of the control catheter. The second tube was pushed into the first tube until about 4 in. of hypotube were protruding from the end of the control catheter. A cyanoacrylate adhesive was applied to the proximal end of the hypotube over about a 12.7 mm section. This section was inserted into the top aperture in the proximal end of the mandrel control lever until flush with the back of the mandrel control lever. The distal end of the first tube was then threaded into the proximal end of the second linear actuator. The second linear actuator was moved to the back most position on the control catheter.

A sizing insert was then fitted into a left body shell. The sizing insert was oriented so that the groove in the sizing insert fit over the ridge in the left shell. The catheter sub assembly was placed into the left body shell so that the mandrel control lever fit into the sizing insert and the second linear actuator fit into the slot in the distal end of the left body shell. A slider rod was inserted through the openings in the sizing insert, mandrel control lever, control shuttle and the second linear actuator. The slider rod was made to rest on two supports in the left body shell. The control spring was inserted into the right body shell so that it fit into the opposing teeth. The right body shell was then placed onto the left body shell and the two were snapped together. Two screws (#4-24×½ in. thread-forming Pan Head) were inserted into the available apertures on the left body shell and tightened. The lock release actuator was snapped into place on the right tab of the second linear actuator with a drop of cyanoacrylate adhesive to ensure that it remained attached.

The second linear actuator, control shuttle, and the mandrel control lever were moved to their forward most positions. The second linear actuator was pulled back and then returned to its forward position. The distal end of the first tube was trimmed by hand with a razor blade to 1.27 mm measured from the tip of the third tube. The sizing insert was pushed forward. The second tube was trimmed by hand using a razor blade to a length of about 0.76 mm measured from the distal most end of the control catheter. An about 4 inch long piece of nitinol wire (0.30 mm diameter) was obtained. A cyanoacrylate adhesive was applied into the tip of the second tube with an elongated applicator tip. The nitinol wire was inserted into the tip of the locking and another piece of wire was used to insert the nitinol wire about 2 mm into the second tube. The cyanoacrylate adhesive was allowed to cure.

The second linear actuator was pulled back and a slot was punched out of the control catheter. The slot had a width that was about the same width as the small axis of the oval lumen of the catheter. A razor was used to skive the slot to a final length of about 19.05 mm. The second linear actuator and the sizing insert were then moved to a forward position.

A retrieval cord approximately 3.05 m long (PTFE fiber with a 0.25 mm O.D.) and a 1.52 m (0.15 mm O.D.) nitinol wire were obtained. The nitinol wire was inserted into one of the 0.04 mm lumens in the first tube and pushed through until it came out into the handle. Tweezers were used to grasp the wire and pull it out of the slot in the handle. About 76.2 mm of wire were made to protrude from the distal end of the control catheter. A loop was formed in the wire by inserting the loose end into the same lumen at the distal end of the control catheter. About 76.2 mm of retrieval cord was then threaded through the resulting loop. The nitinol wire was pulled through the catheter until the retrieval cord protruded into the handle.

A sealing device was obtained. A needle of a type commonly used for sewing was threaded with the retrieval cord and the needle was inserted through the PTFE bag opposite the lock loop and through the lumen of the proximal eyelet of the sealing device. The nitinol wire was then threaded through the remaining unoccupied 0.04 mm lumen in the first tube with the loop end of the wire pointing distally. The needle was removed from the retrieval cord and the cord was threaded through the loop on the nitinol wire. The retrieval cord was then pulled through the catheter in the manner described previously.

The control shuttle was retracted approximately 12.7 mm. The second tube was then threaded through the eyelets of the device. Tweezers were used to grasp the retrieval cord and pull in to the outside of the handle. A loop was formed in a portion of small diameter nitinol wire. The loop was inserted through an aperture in the distal portion of the top of the control shuttle. The retrieval cord was threaded through this loop and pulled through the aperture in the distal portion of the control shuttle. The retrieval cord lock was removed from the control shuttle and one free end of the retrieval cord was inserted through the aperture in the retrieval cord lock from the bottom. Four over hand knots were tied in the cord. Excess cord was trimmed by hand and the retrieval cord lock was returned to the control shuttle.

The remaining free retrieval cord was pulled until all slack was gone. The remaining free end of the retrieval cord was inserted into an aperture in the front of the top of the control shuttle. The retrieval cord was pulled until taught and the retrieval cord lock was snapped closed. The cord was trimmed by hand to about 20.32 cm.

The second tube was flared by obtaining a soldering iron with a sharp tip and heating it to about 500° F. The tip of the iron was inserted into the second tube until a flare was created that was approximately 1.39 mm in diameter. The locking loop on the device was chilled.

Example 4 (Tear Drop)

A length of 0.23 mm diameter nitinol wire (Fort Wayne Metals, Fort Wayne, IN.) was obtained. The specific length of the wire was not measured, it is only necessary that the wire be long enough to double through the feed holes described in the following paragraph. The wire was obtained having been electro polished.

Figure 17:
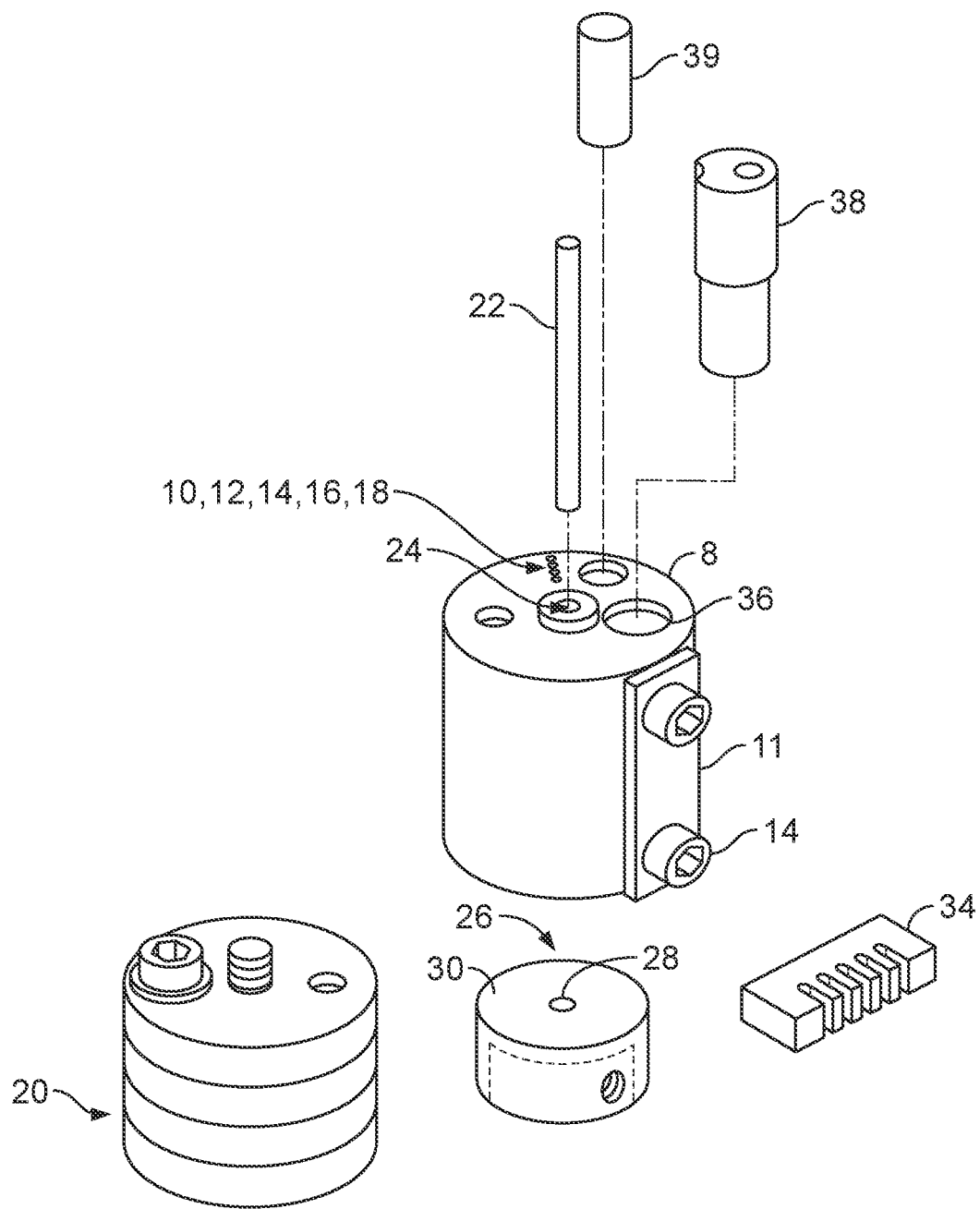
FIG. 17 is a schematic of a base jig assembly including winding jig, wire weight and wire guide.

A base jig 8 as described in FIG. 17 was obtained. The base jig was secured in a chuck of a lathe and center pin 22 was inserted into center pin hole 24 far enough to securely seat it. A knot was tied into one end of one length of a length of nitinol wire and the unknotted end was fed through a wire feed hole 10. Two additional lengths of nitinol wire were folded in half and the free ends were fed through the remaining four feed holes 12, 14, 16, 18. Weights 20 were attached to the free ends of the five wires to hold the wires taut and in place.

The other end of center pin 22 was located inside the center hole 28 of tail stock support 26, which was chucked into the tail stock, wherein the closed face of the tail stock support 26 faced the base jig 8. The base jig 8 and tail stock support 26 were positioned about 5 cm apart. A wire guide 34 was used to prevent the wires from crossing. The base jig 8 was positioned so that the wire feed holes 12, 14, 16, 18 were oriented vertically above the center pin 22 and the wires were positioned on the trailing side of the center pin 22. The wires were wrapped twice around the center pin 22 and left to hang parallel to the wire feed holes.

The petal jig hole 36 was rotated 720°. The petal jig 38 was inserted into the petal jig hole 36. Without crossing the wires, the wires were wrapped counter clockwise around the petal jig 38 past the tear drop pin 39 and around the circumference of the tear drop pin 39. The wires were wrapped around the outer circumference of the petal jig 38 to bring the wire between the petal jig 38 and the center pin 22. They were then wrapped around the center pin 22 twice.

The wires were placed under anchor plate 11. The anchor plate 11 was secured with Allen head screws 14. The wires were cut on the weight 20 side of the anchor plate 11.

With the weights 20, the tail stock support 26, and the wire guide 34 removed, the assembly was placed in a convection oven set to 475° C. for 14 minutes. The assembly was removed from the oven and quenched in water. The jigs were disassembled and the article was removed.

The wire ends were trimmed to the eyelets and the petals were fanned in the same direction as the helical winding, such that each petal was oriented 72° relative to the adjacent petal.

The article was powder coated with FEP powder (obtained from in house stock) in the following manner. A 2 mm outer diameter steel hollow mandrel was obtained of sufficient length to hold the article and have remaining length to extend into the commercial blender. The mandrel was inserted into the center hole of the article. One end the mandrel was grounded. A commercial blender (Variable Speed Lab Blender, Waring, Torrington, CT) was obtained and a quantity of FEP powder was added, leaving the tip of the blender blades exposed. The article and mandrel were suspended in the center of the blender, the lid was replaced, and the blender was turned on to the highest setting for about 5 seconds. The article and mandrel were removed, the mandrel was tapped to achieve a more uniform powder coating, the powder coating was vacuumed from the mandrel and the article and mandrel were then hung inside a convection oven set to 320° C. for 3 minutes. The article and mandrel were removed from the oven, allowed to cool, and excess FEP was removed from the article, the mandrel was removed.

In a separate process, a lock loop 43 (illustrated in FIG. 18A) was manufactured. The lock loop 43 was inserted through a hypotube 45 (smaller than the ID of the eyelets) with the looped end 47 of the lock loop 43 straightened. The hypotube 45 was inserted through the eyelets from the distal end until lock loop eyelet 49 is situated over the distal eyelet 608 of the device. The hypotube was removed.

Figure 18C:
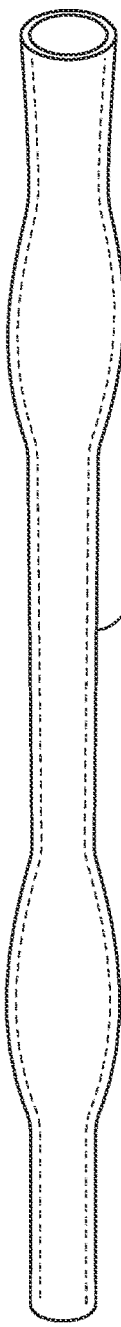

A crimped mandrel 41 (shown in FIGS. 18B and 18C) was inserted into the article through the eyelets with the lock loop 43 along the outer length of the mandrel 41. The article was extended in length on the mandrel by grasping the proximal and center eyelets with tweezers. The eyelets were fixed in place by positioning them beyond the crimps in the mandrel.

Next, a porous ePTFE film having the following properties was obtained:
Methanol bubble point of 0.7 psi
Mass/area of 2.43 grams/square meter
Longitudinal matrix tensile strength of 96000 psi
Matrix tensile strength in the orthogonal direction of 1433 psi
Longitudinal maximum load of 1.6 kg/inch
Thickness of 0.00889 mm Methanol bubble point is measured using a custom built machine with a 1 inch diameter foot, a ramp rate of 0.2 psi/second and a liquid media of methanol. Length and width of the material are measured using a metal ruler. Mass/area is measured using a balance (Model GF-400 Top Loader Balance, ANG, San Jose CA.) with a 36×5 inch sample. Longitudinal maximum load is measured using a materials test machine (Model 5564, Instron, Grove City, PA) equipped with a 10 kg load cell. The gauge length is 2.54 cm and the cross head speed is 25 mm/minute. Sample width is 2.54 cm. Longitudinal tensile test measurements are taken in the length direction of the material. Thickness is measured using a thickness gauge (Mitutoyo Digital Indicator 547-400) with a foot diameter of ¼ inch. The longitudinal matrix tensile strengths (MTS) are calculated using the following equation: Density is calculated using the formula, density=mass/volume as described in a previous example.

A 30 mm film tube is constructed from the ePTFE material in the following manner. For a 25 mm diameter device, a film with a slit width of about 1.905 cm is wound on a 30 mm OD mandrel. The amount of film overlap is not critical but no overlap of the edges is unacceptable. The film tube is then removed from the mandrel and stretched to make the ID of the tube to be about 25 mm. The film tube was slipped over the tensioned article and using ePTFE film, the ends of the tube were cinched around the center of the device then the eyelets.

Another porous ePTFE film, having a layer of FEP, was obtained having the following properties:
Mass/area of 36.1 grams/square meter
Maximum Load, Longitudinal of 12.6 kg/inch
Maximum Load, Transverse of 0.3 kg/inch
Thickness of 0.030 mm Test methods for the above tests are described previously. The FEP thickness in the film is about 62.5%. FEP thickness (%) is calculated as ratio of the FEP thickness and the film thickness. The reported value represents the average measurements for five samples. FEP thickness and film thickness is measured from scanning electron microscope images of cross sections of the ePTFE/FEP laminate material in the following manner. The magnification is chosen to enable the viewing of the entire film thickness. Five lines perpendicular to the horizontal edge of the image are randomly drawn across the full thickness of the film. Thickness is determined by measuring the thickness of the FEP and the thickness of the film.

A 2 mm wide strip of this FEP-coated ePTFE film, with the FEP side down, was wrapped four times around the cinched portions and heated with a soldering iron to bond the film layers together.

The article and mandrel were placed inside a convection oven set to 320° C. for 3 minutes and then removed and allowed to cool. The excess ePTFE material was trimmed and the article removed from the mandrel.

Example 5 (Long 5 Wire)

An article was constructed in the same manner as example 1 with the following exceptions:
Instead of using petal jig 38, self centering petal jig 39 (FIG. 19) was used wherein jig 39 was placed over the center pin 22 and tail stock support 26 was introduced prior to wrapping the first eyelet. After wrapping the first eyelet, self centering petal jig 39 was inserted into petal jig hole 36. The wire was wrapped around the perimeter of petal jig 39 to form petals, and wrapping was continued around center pin 22 to create a second eyelet. A fully extended final article of this example is shown in FIGS. 20A and B.

Example 6 (Long 10 Wire)

An additional article 32 shown in FIG. 21 was constructed using two intermediate (i.e., not powder coated) articles (one inner and one outer) of example 5, wherein the intermediate articles were wrapped in opposite directions. Additionally the inner intermediate article was manufactured such that the eyelets of the inner intermediate article would fit within the eyelets of the outer intermediate article. Prior to FEP coat, the inner and outer intermediate articles were nested using the following method:

In order to achieve nesting of the two intermediate articles, the distal eyelets and the proximal eyelets must be nested. Inner intermediate article was positioned at the end of a straight, circular mandrel. One eyelet of the outer intermediate article was positioned over an eyelet of the inner intermediate article and both intermediate articles were repositioned to the other end of the mandrel. The remaining eyelet of the outer intermediate article was positioned over the remaining eyelet of the inner intermediate article. They were arranged such that the overlapping wires were equally spaced (about 72° apart) thereby creating a frame. The frame was subsequently FEP coated and covered with an ePTFE bag in order to create the final article.

Example 7 (Short 6 Wire)

Figure 22B:
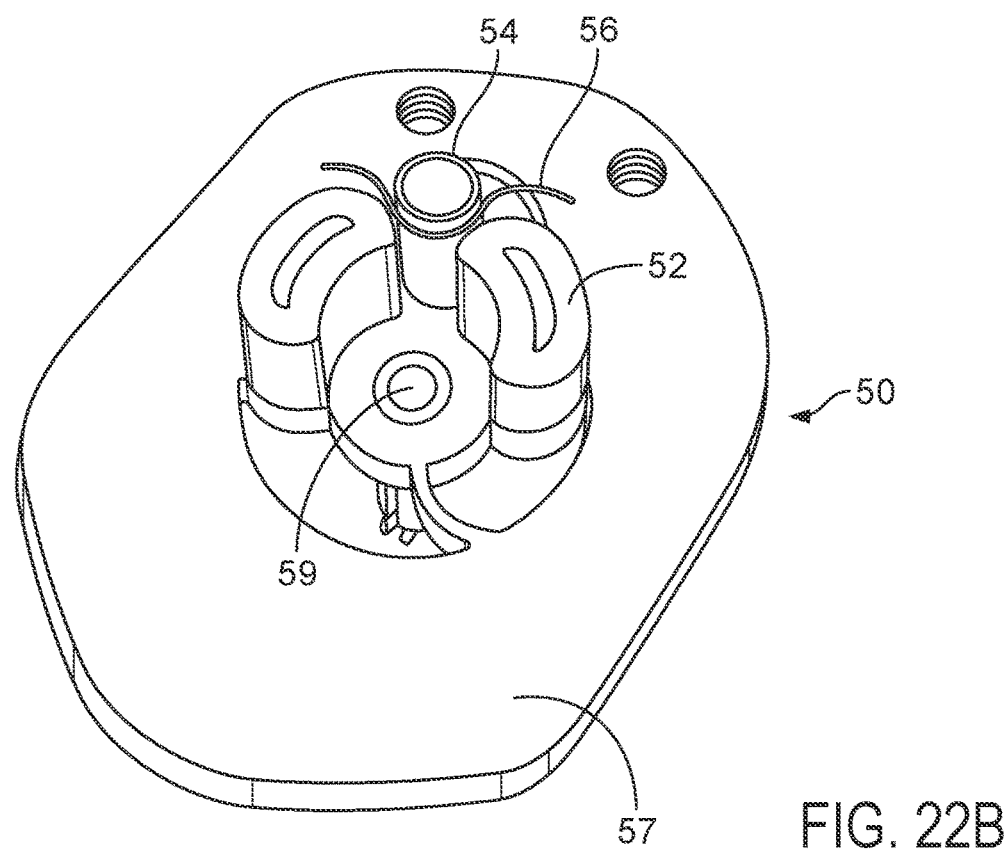
FIG. 22B is an illustration of an embodiment of a base jig.

With the following exceptions, an article similar to that as described in example 1 was created: A similar jig 50 illustrated in FIG. 22B as previously described in example 1 was obtained. The petal jigs 52 and waist jig 54 were positioned as shown in FIG. 22B. The wire wrapping process is shown in the wire path 56 depicted in FIG. 22B, wherein the wire starts at anchor points 57 and ends at eyelet pin 58 (not shown) that is inserted into eyelet pin hole 59. The wire is wrapped 720° around the eyelet pin at the start of the device wrapping and at the finish of the device wrapping. The fully extended final article 51 of this example is shown in FIG. 22A.

Example 8 (Short 12 Wire)

Figure 23B:
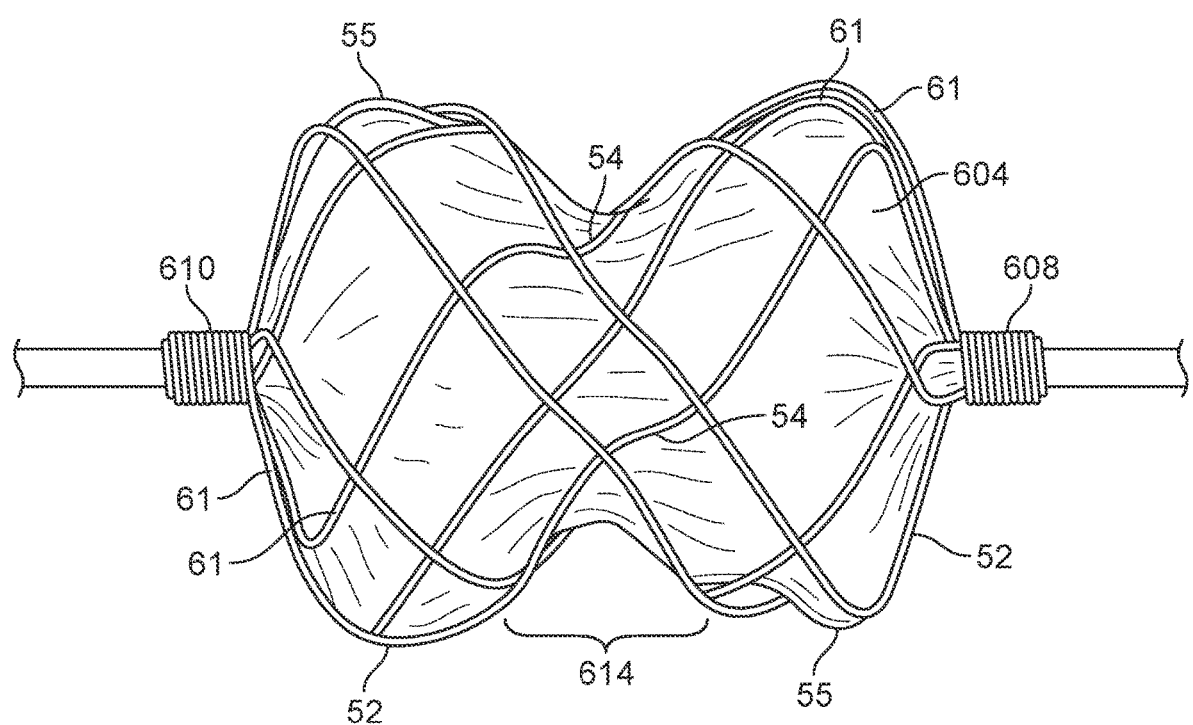
FIG. 23B is a side view of the sealing device of FIG. 23A in an elongated configuration on a mandrel.

An additional article (FIGS. 23A and 23B) was constructed using two intermediate (i.e., not powder coated) articles (one inner and one outer) of example 7 wherein, the intermediate articles were wrapped in opposite directions. Additionally the inner intermediate article was manufactured such that the eyelets of the inner intermediate article would fit within the eyelets of the outer intermediate article.

Prior to FEP coat, the inner and outer intermediate articles were nested using the following method:

In order to achieve nesting of the two intermediate articles, the distal eyelets and the proximal eyelets must be nested. Inner intermediate article was positioned at the end of a straight, circular mandrel. One eyelet of the outer intermediate article was positioned over an eyelet of the inner intermediate article and both intermediate articles were repositioned to the other end of the mandrel. The remaining eyelet of the outer intermediate article was positioned over the remaining eyelet of the inner intermediate article. They were arranged such that the overlapping wires were equally spaced (about 72° apart) thereby creating a frame. The frame was subsequently FEP coated and covered with an ePTFE bag in order to create the final article.

Example 9 (Lock Loop Build)

Figure 24A:
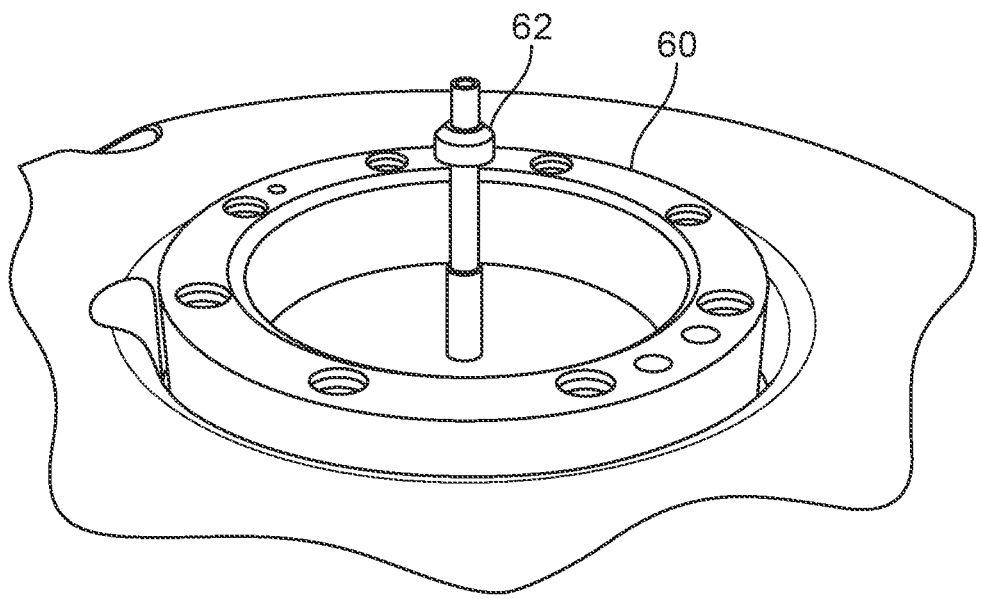
FIG. 24A is a perspective view of a base jig.
Figure 24B:
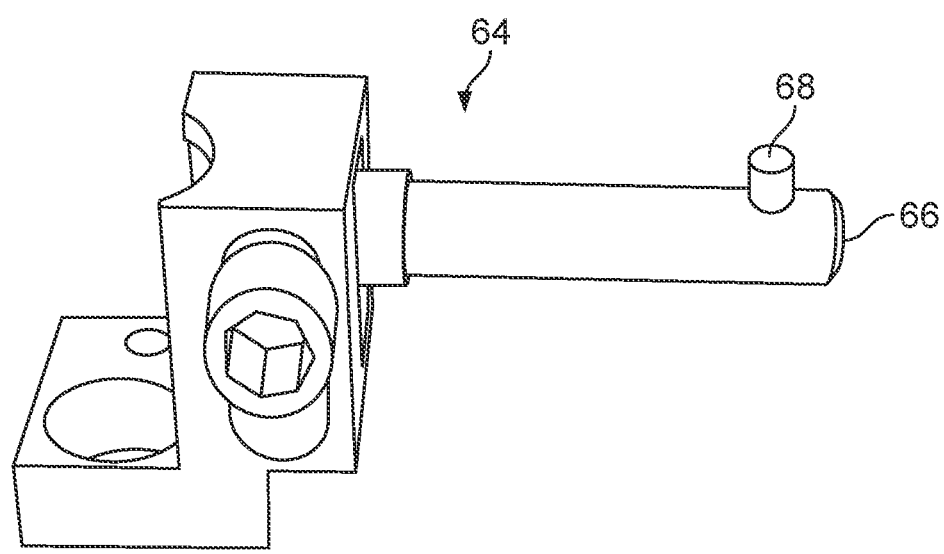
FIG. 24B is a side view of a lock loop forming tool.

Wire was obtained as described in the previous examples. A lock loop base jig 60 (FIG. 24A) with center pin 22 was placed in custom stand as a manufacturing aid. A button component 62 configured such that the inner lumen is not round but is keyed to keep from rotating on center pin was obtained. The wire was formed into a loop and the loop was inserted through the lumen of the button 62. The button with wire loop was threaded onto center pin 22 with loop toward the opposite side of center pin as the keyed portion of the inner lumen of the button component. The keyed portion of the button component 62 was situated to the right of the lock loop base jig 60. A wire was chosen and bent toward the builder then wrapped 360° around the button component 62, then wrapped around the center pin 22 for a minimum of four revolutions and tied off after the fourth revolution. The wire wraps should be spaced apart approximately 1 mm. Loop forming tool 64 (FIG. 24B) was inserted in lock loop base jig 200 against the center pin 22. The free wire was wound about 370° around shaft 66 of loop forming tool 64 and then wrapped around the pin 68 on the loop forming tool 64 and anchored onto the lock loop base jig 60. The base jig 60 and loop forming tool 64 were removed from the stand and placed in an oven. The entire assembly was heated in an oven such as described previously for 14 min. at 475° C. The lock loop was removed from the jig 60 and loop forming tool 64 and the excess wire was trimmed.

Example 10 (Space Filling Device)

The following embodiments teach a heat set for the device described in Example 7 prior to the application of the cover, hereinafter called the frame of Example 7.

The frame of Example 7 was placed over about a 2 mm mandrel. The mandrel 72 was crimped on both sides if the article in order to secure it from moving. The frame was then placed on the tubular cylinder 70 described in FIG. 25A, such that the frame outer perimeter rested on the upper edge of cylinder 70. Cap 74 was then placed over the frame and cylinder 70 as shown in FIG. 25B and secured in place via set screw 76. The entire assembly was then placed in a forced air oven set to 475° C. for 14 minutes. The assembly was removed from the oven and quenched in room temperature water. The frame 78 was subsequently FEP powder coated as described in Example 2.

Example 11 (Space Filling Anchors)

The following embodiments teach an anchor means for the device described Example 10.

Figure 26B:
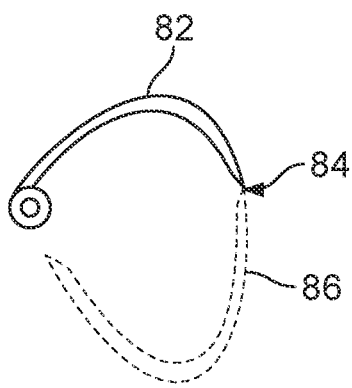
Figure 26C:
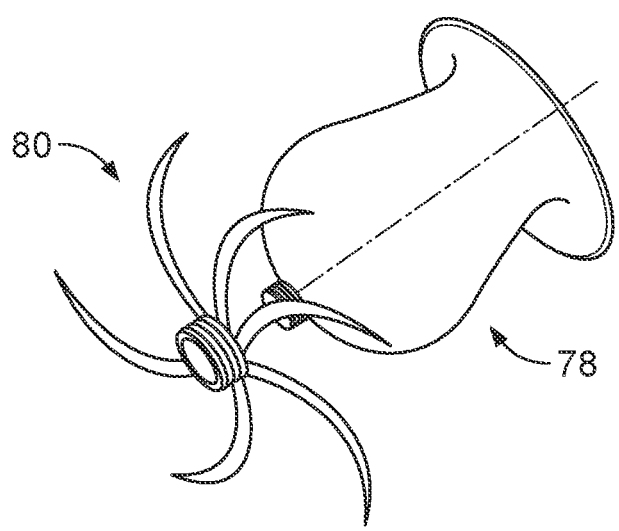
Figure 27:
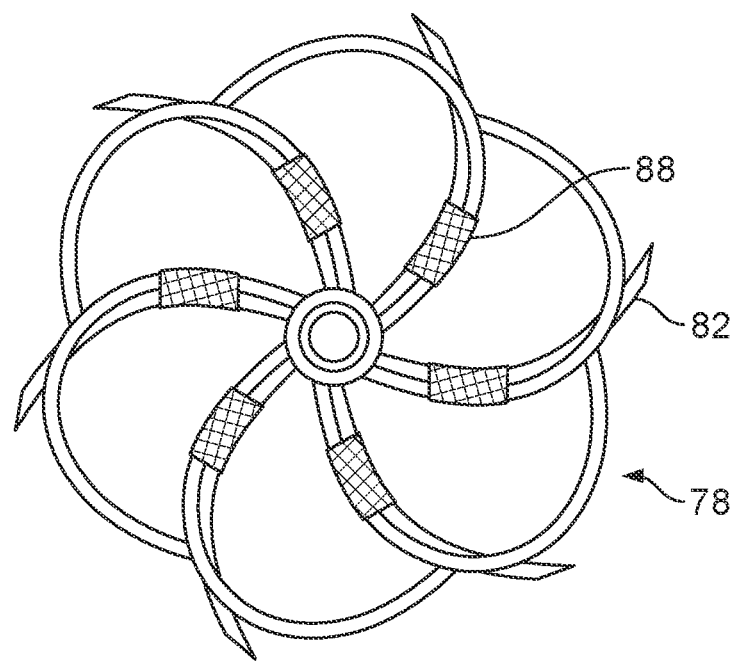
FIG. 27 is an end view of a sealing device wire frame with an anchor component attached.

(a) An anchor component 80 as shown in FIG. 26A was created by the method as generally shown in FIG. 26B. The wire 82 of each of the petals was cut at location 84 thereby eliminating the remainder 86 of the length of the loop, resulting in anchor 80. Anchor component 80 was next affixed to frame 78 as generally shown in FIG. 26C. The spokes 82 of anchor 80 were aligned with the wires of frame 78. A tape made from ePTFE film with a thin layer of FEP was wrapped 88 around the wires 82 and the wires of frame 78 and then heated to bond the wires together as shown in FIG. 27.

Figure 28:
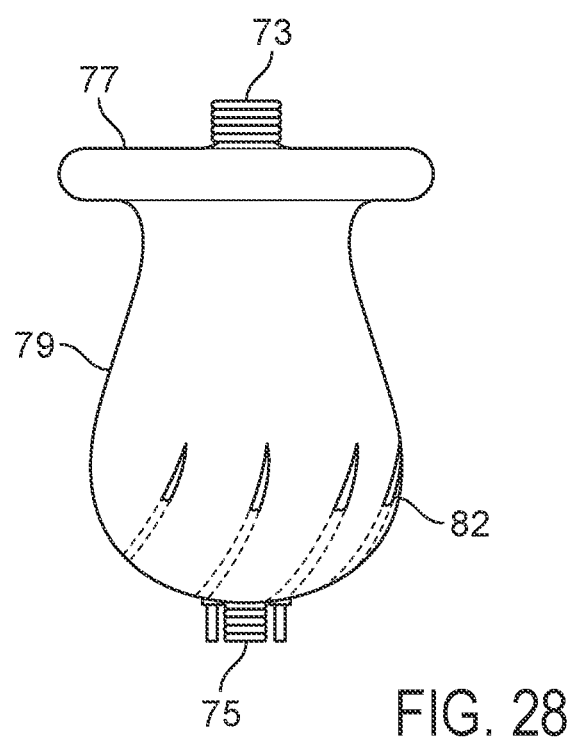
FIG. 28 is a side view of a covered sealing device with anchor component attached.

The article was powder coated with FEP powder as previously described. The frame 78 was covered as previously described, after which wires 82 were individually manipulated to protrude through the sealing member 106 as shown in FIG. 28.

Figure 29A:
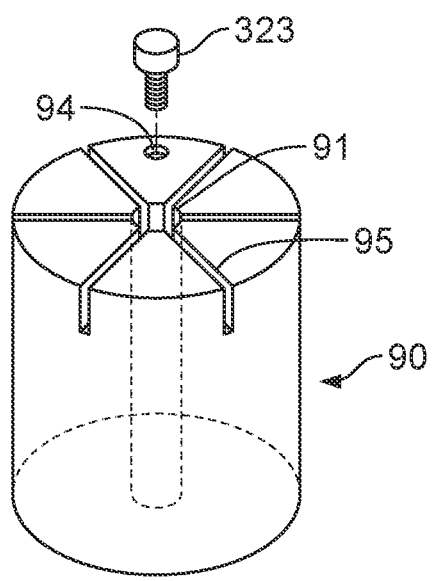
FIGS. 29A-C are illustrations of anchor component forming tools.
Figure 29B:
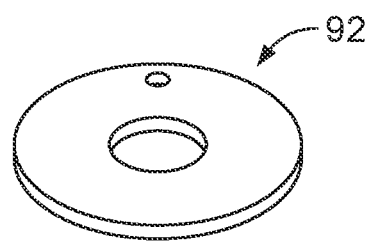
Figure 29C:
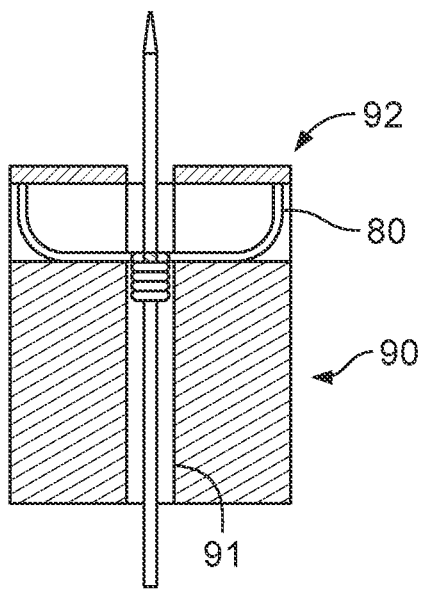

(b) In another embodiment, the anchor component 80 of Example 11 (a) was further modified as follows. Jig 90 and washer 92, as shown in FIGS. 29A and 29B, respectively, were obtained. The anchor component 80 was inserted, eyelet down, into jig 90, such that eyelet of 80 was located inside hole 91 and the wires 82 were located inside grooves 95 of jig 90. Washer 92 was placed on top of anchor component 80 to hold it in place and the washer 92 was secured with screw 323 in hole 94, as shown in FIGS. 29A-29C, which caused the points of the wire 82 to orient toward the face of the washer.

(c) In another embodiment, the anchor component 80 (shown in FIG. 30) is manufactured as follows:

An about 1 meter length of 10% platinum drawn filled nitinol wire (Fort Wayne Metals, Fort Wayne, IN.) with a diameter of about 0.23 mm is obtained. The specific length of the wire is not measured, it is only necessary that the wire be long enough to complete the winding pattern as described in the following paragraph. The wire is obtained having been electropolished. Electropolishing nitinol wire imparts certain well known properties, such as spontaneously forming a titanium dioxide layer on the surface, selectively reducing the amount of nickel on the surface of the wire, and removing some of the stresses in the wire, thus improving fatigue.

A base jig 8 as described in FIG. 17 is obtained. A knot is tied into one end of one length of an about 0.5 meter long wire and the unknotted end is fed through a wire feed hole 10. Two additional lengths of wire (about 1 meter each) are folded in half and the free ends are fed through the remaining four feed holes 12, 14, 16, 18, with the wire entering the holes at funnel-shaped opening 19 (not shown) with the small feed holes at the bottom of opening 19. The wires then exit through holes 10, 12, 14, 16 and 18 at the flat end surface of jig 8. Weights 20 are attached to the free ends of the five wires to hold the wires taut and in place. The base jig is secured in a chuck of a lathe and center pin 22 is inserted into center pin hole 24 far enough to securely seat it.

The other end of center pin 22 is located inside the center hole 28 of tail stock support 26 which is chucked into the tail stock, wherein the closed face 30 of the tail stock support 26 faces the base jig 8. The base jig 8 and tail stock support 26 are positioned about 5 cm apart. A wire guide 34 is used to prevent the wires from crossing. The base jig 8 is positioned so that the wire feed holes 10, 12, 14, 16, 18 are oriented vertically above the center pin 22 and the wires are positioned on the trailing side of the center pin 22.

The petal jig hole 36 is rotated 720°. The petal jig 38 is inserted into the petal jig hole 36. Without crossing the wires, the wires are placed on top of the petal jig 38. The base jig 8 is rotated 360° to create the petals of the device. The base jig 8 is rotated another 720° with the wires placed on top of the center pin 22.

With the weights 20, the tail stock support 26, and the wire guide 34 removed, the assembly is placed in a convection oven set to 475° C. for 14 minutes. The assembly is removed from the oven and quenched in water. The jigs are disassembled and the article is removed. The wire ends are trimmed to the eyelets and the anchor loops are fanned in the same direction as the helical winding, such that each anchor loop is oriented 72° offset relative to the adjacent anchor loops. The anchor loops are crimped at the center by hand and heat set again as previously described.

Figure 31:
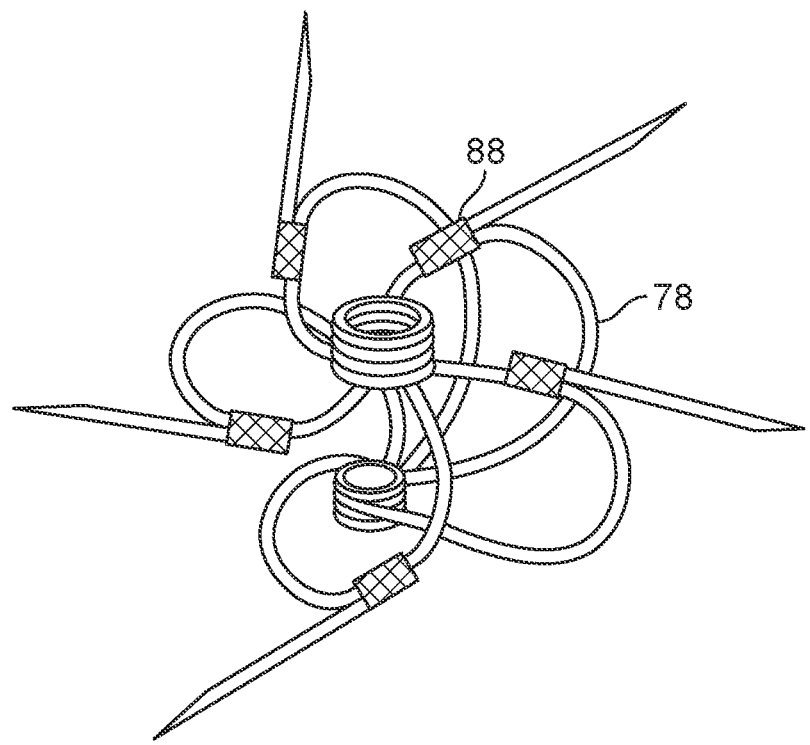
FIG. 31 is a perspective view of a wire frame with anchor components attached.
Figure 32:
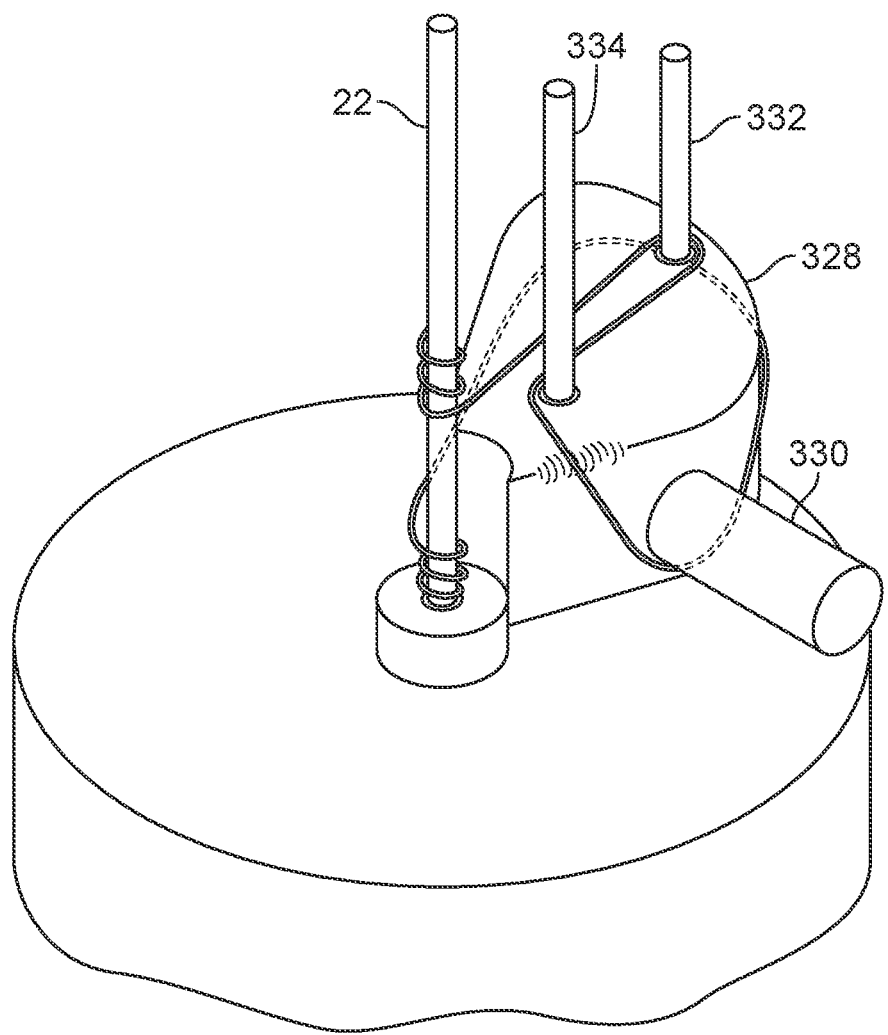
FIG. 32 is a perspective view of a winding path and jig for winding a sealing device with elongated waist area.

(d) In another embodiment, anchor components are manufactured by clipping about 2 cm straight lengths of nitinol wire 71. A tape made from ePTFE film with a thin layer of FEP is wrapped 88 around the wires 71 and the wires of frame 78 and then heated to bond the wires together as shown in FIG. 31.

Example 12 (Space Filler with 2 Planes of Anchoring)

A device as previously described in Example 10 with anchors as described in example 11(d) is manufactured by attaching the anchors at multiple locations along the wires of frame 78.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device for sealing a defect or structure in a heart, the medical device comprising:
    a wire frame that includes a plurality of wound wires that each extend from a proximal end of the wire frame to a distal end of the wire frame, the wires forming:
    a first occluding member;
    a second occluding; and
    a defect-occupying portion disposed between the first occluding member and the second occluding member, wherein the defect-occupying portion is adapted to substantially fill a range of defect sizes from a largest defect size to a smallest defect size, the range being at least about 7 mm; and
    a sealing member in contact with the frame.

2. The device of claim 1, wherein the plurality of wound wires comprises six wound wires.

3. The device of claim 1, wherein the plurality of wound wires comprises eight wound wires.

4. The device of claim 1, further comprising a first eyelet near the proximal end of the wire frame and a second eyelet near the distal end of the wire frame, the first eyelet formed from first end portions of each wire of the six wound wires, and the second eyelet formed from second end portions of each wire of the six wound wires.

5. The device of claim 1, further comprising a non-metal attachment member adapted to couple with one or more components of a delivery system.

6. The device of claim 1, wherein the first occluding member is adapted to conform to a geometry of a first tissue surface and the second occluding member is adapted to conform to a geometry of a second tissue surface.

7. The device of claim 6, wherein the first occluding member and the second occluding member maintain a generally flat profile when the defect-occupying portion deflects to an outer diameter that is less than about 60% of the nominal outer diameter of the defect-occupying portion.

8. A medical device for sealing a defect or structure in tissue, comprising: a frame that includes:
    a first occluding member that is adapted to conform to a geometry of a first tissue surface and to provide an apposition force against the first tissue surface,
    a second occluding member that is adapted to conform to a geometry of a second tissue surface and to provide an apposition force against the second tissue surface, and
    a defect-occupying member disposed between the first occluding member and the second occluding member and adapted to not provide substantial apposition force against tissue around an aperture of the defect, and
    a sealing member in contact with the frame, wherein the frame is defined by a plurality of wound elongate members that each extends from a proximal end of the frame to a distal end of the frame, wherein each elongate member includes:
    a first portion that defines a petal of the first occluding member;
    a second portion that defines a petal of the second occluding member; and
    a third portion, disposed between the first portion and the second portion, defining an inflection region of the defect occupying member.

9. The device of claim 8, wherein the plurality of wound elongate members comprises six elongate members.

10. The device of claim 8, wherein the plurality of wound elongate members comprise eight elongate members.

11. The device of claim 10, further comprising a non-metal attachment member adapted to couple with one or more components of a delivery system.

12. The device of claim 11, wherein the first occluding member and the second occluding member maintain a generally flat profile when the defect-occupying portion deflects to an outer diameter that is less than about 60% of the nominal outer diameter of the defect-occupying portion.

13. The device of claim 12, wherein the petal of the first occluding member is adapted to bear a load associated with the first tissue surface without imparting a substantial force to the other elongate members of the plurality of elongate members, and wherein the petal of the second occluding member is adapted to bear a load associated with the second tissue surface without imparting a substantial force to the other elongate members of the plurality of elongate members.

14. The device of claim 13, wherein the plurality of elongate members are lasercut from a Nitinol tube.

15. The device of claim 14, wherein the elongate members are wires.

* * * * *